(12) United States Patent
Yarema et al.

(10) Patent No.: US 8,916,544 B2
(45) Date of Patent: Dec. 23, 2014

(54) HYBRID SCFA-HYDROXYL-DERIVATIZED MONOSACCHARIDES, METHODS OF SYNTHESIS, AND METHODS OF TREATING DISORDERS

(75) Inventors: Kevin J. Yarema, Woodstock, MD (US); Udayanath Aich, Cambridge, MA (US); Christopher Thomas Campbell, Baltimore, MD (US); Srinivasa-Gopalan Sampathkumar, New Delhi (IN); Sean S. Choi, Columbia, MD (US); Michael Adam Meledeo, San Antonio, TX (US); Christopher Weier, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 1160 days.

(21) Appl. No.: 12/671,994

(22) PCT Filed: Aug. 7, 2008

(86) PCT No.: PCT/US2008/009490
§ 371 (c)(1),
(2), (4) Date: May 13, 2011

(87) PCT Pub. No.: WO2009/020641
PCT Pub. Date: Feb. 12, 2009

(65) Prior Publication Data
US 2011/0206734 A1 Aug. 25, 2011

Related U.S. Application Data

(60) Provisional application No. 60/963,966, filed on Aug. 8, 2007.

(51) Int. Cl.
*A61K 31/70* (2006.01)
*C08B 37/00* (2006.01)
*C07H 7/027* (2006.01)
*C07H 5/06* (2006.01)
*C07H 13/04* (2006.01)

(52) U.S. Cl.
CPC ............... *C07H 13/04* (2013.01); *C07H 7/027* (2013.01); *C07H 5/06* (2013.01)
USPC .............................................. 514/62; 536/53

(58) Field of Classification Search
None
See application file for complete search history.

(56) References Cited

U.S. PATENT DOCUMENTS

2006/0127977 A1 6/2006 Zoller et al.

FOREIGN PATENT DOCUMENTS

| WO | WO2006/127977 | * | 11/2006 |
| WO | WO 2006127977 A1 | | 11/2006 |

OTHER PUBLICATIONS

Ferse et al., Tetrahedron, 1999 (55) pp. 3749-3776.*
Sinou et al., Journal of Carbohydrate Chemistry, vol. 21, No. (6), pp. 545-558, 2002.*
Form PCT/ISA220, WO, Nov. 3, 2008, International Search Report.
Form PCT/ISA/237, WO, Nov. 3, 2008, Written Opinion of the Interntl Searching Auth.
Campbell et al., "Metabolic Oligosaccharides Engineering Perspectives, Applications, and Future Directions", Molecular Biosystems, vol. 3, pp. 187-194, p. 189, Fig. 1; p. 190, Table 1; p. 193, col. 1 (Mar. 2007).

* cited by examiner

*Primary Examiner* — Traviss C McIntosh, III
(74) *Attorney, Agent, or Firm* — Edwards Wildman Palmer LLP; Peter F. Corless; Richard B. Emmons

(57) ABSTRACT

Described herein are fatty acid carbohydrate-hydroxyl-hybrid compounds and derivatives thereof, and methods of treating or preventing disease and disease symptoms using the compounds and compositions thereof.

8 Claims, 14 Drawing Sheets

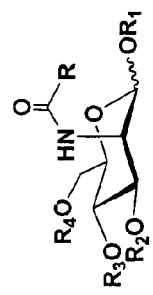

ManNAc scaffold (based on Formula II)

Finding: Based on experiments shown in Drawings 5 & 6, unique biological activities result when:
(1) at least one of $R_1$, $R_2$, $R_3$, or $R_4$ is a hydroxyl group, and
(2) at least one of $R_1$, $R_2$, $R_3$, or $R_4$ is a SCFA

B

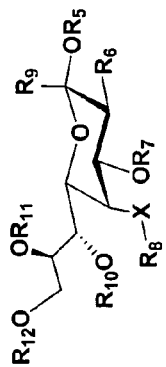

GlcNAc scaffold
(based on Formula III)

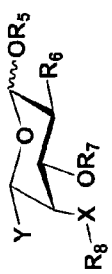

GalNAc scaffold
(based on Formula IV)

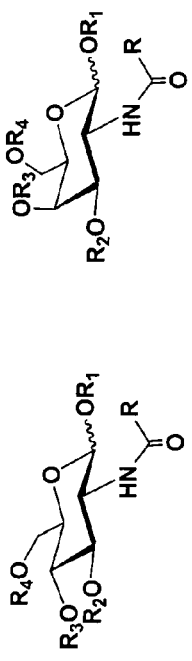

Fucose scaffold
(based on Formula VI)

Sialic acid scaffold
(based on Formula VII)

(1) at least one of $R_1$, $R_2$, $R_3$, $R_4$, $R_5$, $R_7$, $R_{10}$, $R_{11}$ or $R_{12}$ is a hydroxyl group, and
(2) at least one of $R_1$, $R_2$, $R_3$, $R_4$, $R_5$, $R_7$, $R_{10}$, $R_{11}$ or $R_{12}$ is a SCFA, and
(3) $R_1$, $R_2$, $R_3$, $R_4$, $R_5$, $R_7$, $R_{10}$, $R_{11}$ or $R_{12}$ can be any or all of $COCH_3$, $COCH_2CH_3$, $CO(CH_2)_2CH_3$, $CO(CH_2)_3CH_3$, and
(4) R, $R_6$, $R_8$, $R_9$, X and Y can be any of the functional groups listed in the text.

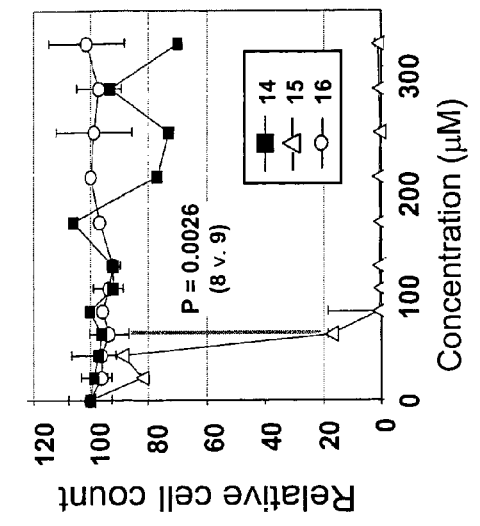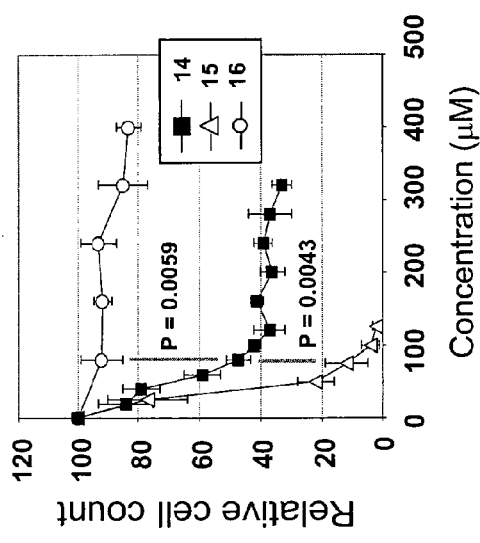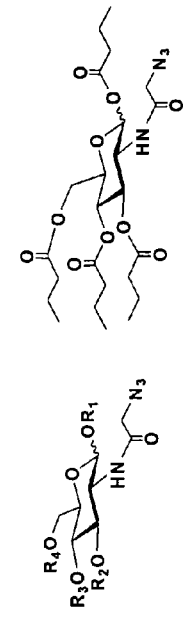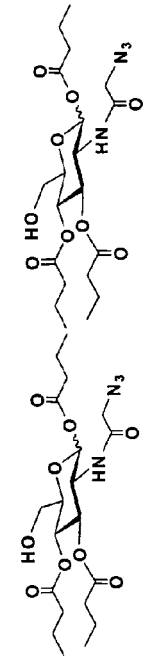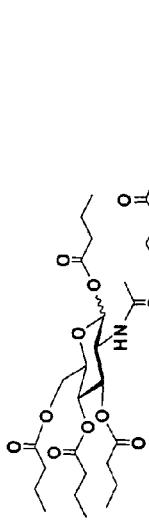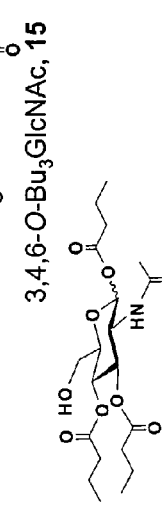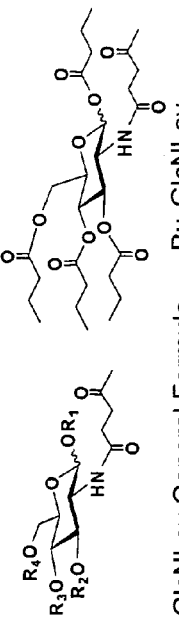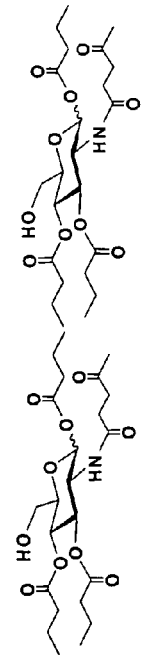
Figure 10

Figure 13

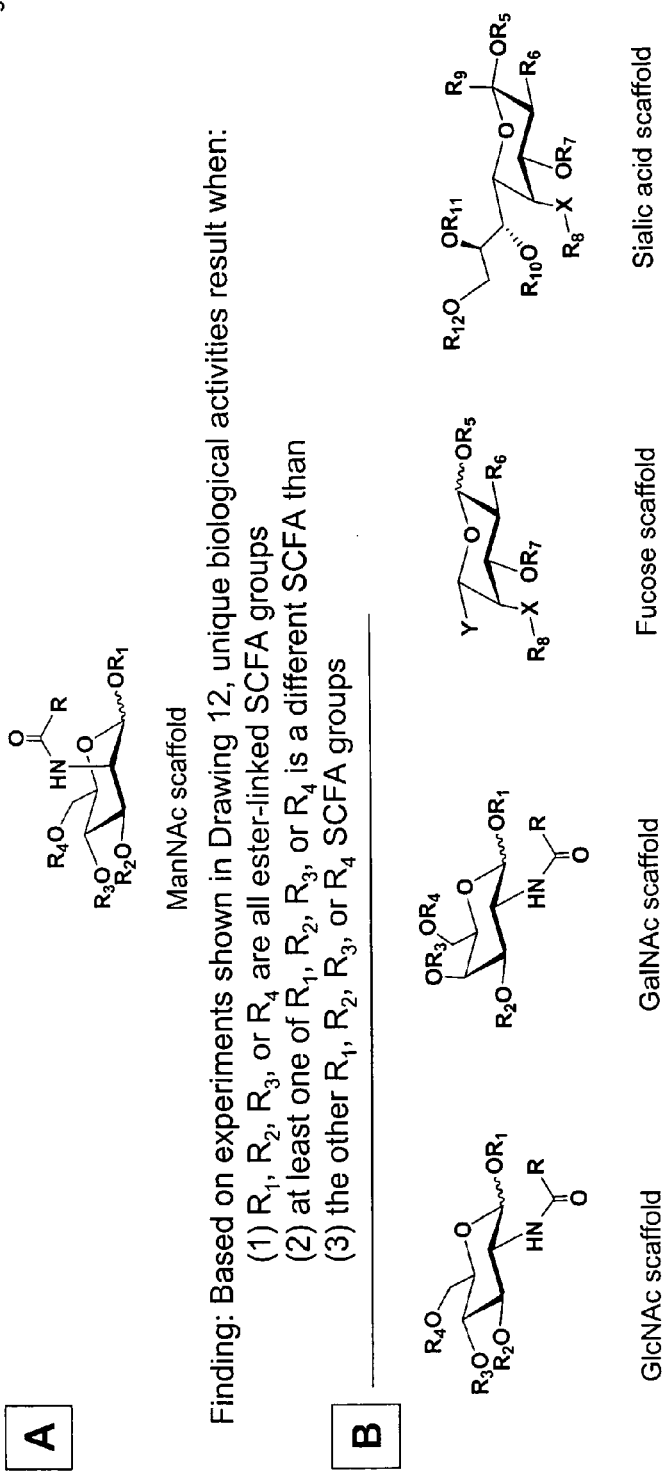

ManNAc scaffold

Finding: Based on experiments shown in Drawing 12, unique biological activities result when:
(1) $R_1$, $R_2$, $R_3$, or $R_4$ are all ester-linked SCFA groups
(2) at least one of $R_1$, $R_2$, $R_3$, or $R_4$ is a different SCFA than
(3) the other $R_1$, $R_2$, $R_3$, or $R_4$ SCFA groups GlcNAc scaffold GalNAc scaffold Fucose scaffold Sialic acid scaffold (1) $R_1$, $R_2$, $R_3$, $R_4$, $R_5$, $R_7$, $R_{10}$, $R_{11}$ or $R_{12}$ are all ester-linked SCFA groups
(2) at least one of $R_1$, $R_2$, $R_3$, $R_4$, $R_5$, $R_7$, $R_{10}$, $R_{11}$ or $R_{12}$ is a different SCFA than
(3) the other $R_1$, $R_2$, $R_3$, $R_4$, $R_5$, $R_7$, $R_{10}$, $R_{11}$ or $R_{12}$ SCFA groups
(4) $R_1$, $R_2$, $R_3$, $R_4$, $R_5$, $R_7$, $R_{10}$, $R_{11}$ or $R_{12}$ can be any or all of $COCH_3$, $COCH_2CH_3$, $CO(CH_2)_2CH_3$, $CO(CH_2)_3CH_3$, and
(5) R, $R_6$, $R_8$, $R_9$, X and Y can be any of the functional groups listed in the text
(6) $R_4$ is a non-hydrolyzable conformer of ester-linked SCFAs

HYBRID SCFA-HYDROXYL-DERIVATIZED MONOSACCHARIDES, METHODS OF SYNTHESIS, AND METHODS OF TREATING DISORDERS

CROSS-REFERENCE TO RELATED APPLICATIONS

This application is the U.S. National Phase Application, pursuant to 35 U.S.C. §371, of PCT International Application Serial No. PCT/US08/009,490, filed Aug. 7, 2008, designating the United States and published in English on Feb. 12, 2009 as publication WO 2009/020641, which claims benefit of U.S. Application Ser. No. 60/963,966, filed Aug. 8, 2007. The entire disclosures of each of the aforementioned patent applications are incorporated by reference in its entirety.

STATEMENT REGARDING FEDERALLY SPONSORED RESEARCH OR DEVELOPMENT

Research supporting this application was carried out in part under funding from the NIH/NCI (5R01CA112314-03). The government of the United States may have rights in the inventions.

BACKGROUND OF THE INVENTION

Uncontrolled cell proliferation characteristic of transformed cells is, at least in part, epigenetic in origin and results from cancer-specific anomalies in chromatin structure. Chromatin consists of DNA, histones, and accessory proteins such as histone deacetylase (HDAC) and histone acetyltransferase (HAT). Together, HDAC and HAT remodel chromatin to provide a "code" that is recognized by the non-histone proteins that regulate gene expression. Not surprisingly, there is growing interest in the precise mechanisms that regulate chromatin remodeling with the bulk of these efforts focused on the inhibition of histone deacetylase (HDAC) activities. In recent years, the ability of HDAC inhibitors (HDACi) to disrupt the cell cycle or selectively induce apoptosis via de-repression of genes such as P21 and BAX in cancer cells, has made HDAC inhibition an attractive avenue for drug development and intense efforts are underway to develop clinically-relevant HDACi for cancer therapy.

In addition to epigenetic modifications, tumorigenesis frequently involves abnormal glycosylation that alters cell surface properties. These changes to the cell surface underlie altered cell adhesion and trigger abnormal inter- and intracellular signaling that simulate cell proliferation and metastasis. Examples of altered cell adhesion which contribute to metastasis include an initial decrease in adhesion that allows a malignant cell to break free of the primary tumor and a later increase in adhesion that allows a circulating cell to adhere to the vessel and extravasate into another tissue. Glycosylation, in particular sialylation, influence the changing adhesive properties of metastatic cells. Abnormal glycosylation also alters the interaction of cell-surface signaling molecules and produces abnormal inter- and intra-cellular signaling. For example, altered glycosylation of integrin influences its associations with other cell surface molecules. Therapies that disrupt the abnormal glycosylation of cancer cells might inhibit cell proliferation and metastasis.

n-Butyrate, a naturally-occurring HDACi belonging to the class of compounds known as short chain fatty acids (SCFAs) has the attractive property of inducing cell cycle arrest and apoptosis in transformed cells while leaving healthy cells unharmed by reactivating cell cycle check point proteins such as $p21^{WAF1}$, a cyclin-dependent kinase inhibitor. Efforts to exploit n-butyrate for clinical treatment of cancer, however, have been stymied by its poor pharmacological properties and the high levels (up to 50 mM) needed for bioactivity. One approach to avoid the pharmacokinetic limitations of butyrate has been to use traditional enzyme-substrate screening assays to discover "drug-like" small molecule HDACi such as trichostatin (TSA), suberoyl hydroxamic acid (SAHA), and MS-275 among others. These compounds inhibit cell growth, induce terminal differentiation, and prevent tumor formation in animal models. Despite these attractive anti-cancer properties and nanomolar binding affinities to HDAC when tested against purified enzyme, the majority of current HDACi clinical candidates require unrealistically high (up to millimolar) concentrations to be effective against cells.

In the area of functionalized N-acyl derivatives of mannosamine, patents exist for the ketone-carrying monosaccharides such as ManLev and FucLev (U.S. Pat. No. 6,936,701 (2005); U.S. Pat. No. 6,458,937 (2002); U.S. Pat. No. 6,075, 134 (2000)) by the Bertozzi group, albeit referring only to the free monosaccharide forms. In the case of azide carrying monosaccharides, Bertozzi group has patents for the in vivo and in vitro applications, including the modified Staudinger ligation process (U.S. Pat. No. 7,122,703 (2006); U.S. Pat. No. 6,570,040 (2003)).

Another patent by Schnaar and coworkers on the N-glycolylmannosamine derivatives employs peracetylation to enhance cellular uptake, in order to abrogate the binding of MAG (myelin associated glycoprotein) via the expression of N-glycolylneuraminic acid moieties (U.S. Pat. No. 6,274,568 (2001)). Although this patent claims two or more acyl groups on the 'O-' moieties, it is mainly restricted to 'acetyl' derivatives and N-glycolyl, N-acetyl, and N-porpanoyl modifications.

Another patent by Esko et al exploits peracetylation for rapid cellular uptake of disaccharides (U.S. Pat. No. 5,639, 734 (1997)) that act as 'molecular decoys' for sialyl transferases.

In the field of short chain fatty acid (SCFA) based drug development, mostly prodrugs containing multivalent SCFAs on innocuous carriers such as lactic acid, triose (glycerol), tetraose (threitol), pentitol, hexose (galactose, glucose) (U.S. Pat. No. 5,830,872 (1998)) have been patented. But none of these patents utilize an active carrier or make any connections to hexosamine as a possible carrier.

The above mentioned patents exploit peracetylation merely to mask the hydrophilicity and poor membrane permeability of monosaccharide derivatives and largely ignore the 'side-effects' or in the case of this report 'critical effects' of the intracellular release of SCFAs, either complete or partial, due to hydrolysis by non-specific esterases and consequent effects on gene expression of oncogenic genes such as $p21^{WAF1/Cip1}$, MUC1 and CXCR4. Additionally, the biomedical applications of MOE covered so far has been in neurite outgrowth, diagnostics and imaging and not particularly pertaining to the development of carbohydrate-based small molecules as anti-cancer drugs.

The goal of the invention is to demonstrate SCFA-hexosamine hybrids, titrating the number of acyl groups on monosaccharides to tailor to Lipinski's rule of five (RO5) to achieve drug-like properties, mixing and matching acyl groups of varying lengths on the monosaccharides, regioselective activity in vitro in mammalian cell cultures, and their isosteric molecules as small-molecule carbohydrate based anti-cancer drugs and as inhibitor of MUC1 expression in particular.

SUMMARY OF THE INVENTION

The compounds of the invention were designed to incorporate a monosaccharide core with a mixture of SCFA substitutions and hydroxyl groups, which deviates from the previous approach of using fully SCFA-derivatized sugar analogs by selectively placing SCFA groups at defined positions on the monosaccharide scaffold to mimic the partially acylated hydrolysis products generated from the per-acylated compounds. Such a strategy is herein referred to as a "mix-and-match" approach. In one embodiment, specific hydroxyl groups are left underivatized. In another embodiment, the mix-and-match approach allows more than one type of SCFA to be attached to the same sugar scaffold. In both cases, unique biological responses are obtained cannot be reproduced with a combination of the separate constituent molecules.

The invention includes, but is not limited to ManNAc-based molecules, and extends to other monosaccharides including GlcNAc-based compounds. The extent of this invention therefore broadly covers any mono- and di-saccharides.

By using the approaches outlined in the previous paragraph, toxicity can be both enhanced (which is beneficial for cancer drug development) or avoided (which is beneficial for a host of applications where MOE is not intended to kill the target cells). Consequently, this invention opens the door to a significant number of MOE applications.

Described herein are compounds, and compositions and methods of generating the compounds thereof, methods of treating disease and disease symptoms, and compounds useful for modulating biological processes for treating disease and disease symptoms.

In one aspect, the invention provides a compound of formula I, or pharmaceutically acceptable salt thereof:

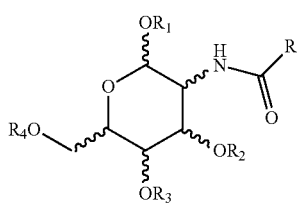

Formula (I)

wherein, each of $R_1$, $R_2$, $R_3$, and $R_4$ is independently H, —C(O)alkyl or —C(O)(CH$_2$)$_n$CH$_3$;

wherein at least one $R_1$, $R_2$, $R_3$, and $R_4$ is H and at least one $R_1$, $R_2$, $R_3$, and $R_4$ is —C(O)alkyl or —C(O)(CH$_2$)$_n$CH$_3$;

each n is independently an integer from 0-18; and

R is alkyl or alkenyl, each of which is optionally substituted with 1-4 substituents selected from acyl, oxo, azido, aryl, halogen, —OC(O)alkyl, or —SC(O)alkyl.

In certain embodiments, the invention provides a compound of formula II, or pharmaceutically acceptable salt thereof:

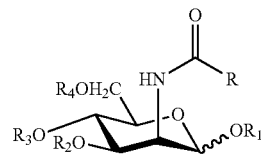

Formula (II)

wherein, each of $R_1$, $R_2$, $R_3$, and $R_4$ is independently H, —C(O)alkyl or —C(O)(CH$_2$)$_n$CH$_3$;

wherein at least one $R_1$, $R_2$, $R_3$, and $R_4$ is H and at least one $R_1$, $R_2$, $R_3$, and $R_4$ is —C(O)alkyl or —C(O)(CH$_2$)$_n$CH$_3$;

each n is independently an integer from 0-18; and

R is alkyl or alkenyl, each of which is optionally substituted with 1-4 substituents selected from acyl, oxo, azido, aryl, halogen, —OC(O)alkyl, or —SC(O)alkyl.

In one embodiment, at least two of $R_1$, $R_2$, $R_3$, and $R_4$ are —C(O)alkyl or —C(O)(CH$_2$)$_n$CH$_3$. In another embodiment, at least three of $R_1$, $R_2$, $R_3$, and $R_4$ are —C(O)alkyl or —C(O)(CH$_2$)$_n$CH$_3$.

In other embodiments, R is alkyl or a substituted alkyl which may be substituted by oxo, azido, aryl, halogen, —OC(O)alkyl, or —SC(O)alkyl.

In other embodiments, R is alkyl or a substituted alkyl which may be substituted by oxo, azido, aryl, halogen, —OC(O)alkyl, or —SC(O)alkyl, $R_1$ is H, and $R_2$, $R_3$, and $R_4$ are each independently —C(O)(CH$_2$)$_n$CH$_3$.

In another embodiment, R is alkyl or a substituted alkyl which may be substituted by oxo, azido, aryl, halogen, —OC(O)alkyl, or —SC(O)alkyl, $R_2$ is H, and $R_1$, $R_3$, and $R_4$ are each independently —C(O)(CH$_2$)$_n$CH$_3$.

In one embodiment, R is alkyl or a substituted alkyl which may be substituted by oxo, azido, aryl, halogen, —OC(O)alkyl, or —SC(O)alkyl, $R_3$ is H, and $R_1$, $R_2$, and $R_4$ are each independently —C(O)(CH$_2$)$_n$CH$_3$.

In another embodiment, R is alkyl or a substituted alkyl which may be substituted by oxo, azido, aryl, halogen, —OC(O)alkyl, or —SC(O)alkyl, $R_4$ is H, and $R_1$, $R_2$, and $R_3$ are each independently —C(O)(CH$_2$)$_n$CH$_3$.

In certain embodiments, R is alkyl or a substituted alkyl which may be substituted by oxo, azido, aryl, halogen, —OC(O)alkyl, or —SC(O)alkyl, $R_3$ and $R_4$ are H, and $R_1$ and $R_2$ are each independently —C(O)(CH$_2$)$_n$CH$_3$.

In still another embodiment, R is alkyl or a substituted alkyl which may be substituted by oxo, azido, aryl, halogen, —OC(O)alkyl, or —SC(O)alkyl, $R_2$ and $R_4$ are H, and $R_1$ and $R_3$ are each independently —C(O)(CH$_2$)$_n$CH$_3$.

In yet another embodiment, R is alkyl or a substituted alkyl which may be substituted by oxo, azido, aryl, halogen, —OC(O)alkyl, or —SC(O)alkyl, $R_1$ and $R_4$ are H, and $R_2$ and $R_3$ are each independently —C(O)(CH$_2$)$_n$CH$_3$.

In other embodiments, R is alkyl or a substituted alkyl which may be substituted by oxo, azido, aryl, halogen, —OC(O)alkyl, or —SC(O)alkyl, $R_2$ and $R_3$ are H, and $R_1$ and $R_4$ are each independently —C(O)(CH$_2$)$_n$CH$_3$.

In another embodiment, R is alkyl or a substituted alkyl which may be substituted by oxo, azido, aryl, halogen, —OC(O)alkyl, or —SC(O)alkyl, $R_1$ and $R_3$ are H, and $R_2$ and $R_4$ are each independently —C(O)(CH$_2$)$_n$CH$_3$.

In yet another embodiment, R is alkyl or a substituted alkyl which may be substituted by oxo, azido, aryl, halogen, —OC(O)alkyl, or —SC(O)alkyl, $R_1$ and $R_2$ are H, and $R_3$ and $R_4$ are each independently —C(O)(CH$_2$)$_n$CH$_3$.

In other embodiments, R is alkyl or a substituted alkyl which may be substituted by oxo, azido, aryl, halogen, —OC(O)alkyl, or —SC(O)alkyl, $R_2$, $R_3$, and $R_4$ are H, and $R_1$ is —C(O)(CH$_2$)$_n$CH$_3$.

In one embodiment, R is alkyl or a substituted alkyl which may be substituted by oxo, azido, aryl, halogen, —OC(O)alkyl, or —SC(O)alkyl, $R_1$, $R_3$, and $R_4$ are H, and $R_2$ is —C(O)(CH$_2$)$_n$CH$_3$.

In still other embodiments, R is alkyl or a substituted alkyl which may be substituted by oxo, azido, aryl, halogen, —OC(O)alkyl, or —SC(O)alkyl, $R_1$, $R_2$, and $R_4$ are H, and $R_3$ is —C(O)(CH$_2$)$_n$CH$_3$.

In certain embodiments, R is alkyl, or a substituted alkyl which may be substituted by oxo, azido, aryl, halogen, —OC(O)alkyl, or —SC(O)alkyl, $R_1$, $R_2$, and $R_3$ are H, and $R_4$ is —C(O)(CH$_2$)$_n$CH$_3$.

In one embodiment, R is alkyl, $R_1$ is C(O)(CH$_2$)$_n$CH$_3$, and $R_2$, $R_3$, and $R_4$ are each independently —COCH$_3$.

In another embodiment, R is alkyl, $R_4$ is C(O)(CH$_2$)$_n$CH$_3$, and $R_1$, $R_2$, and $R_3$ are each independently —COCH$_3$.

In certain embodiments, the invention provides a compound as described above wherein each n is independently 0. In certain embodiments, the invention provides a compound as described above wherein each n is independently 1. In certain embodiments, the invention provides a compound as described above wherein each n is independently 2. In certain embodiments, the invention provides a compound as described above wherein each n is independently 3.

In another embodiment, the invention provides a compound of formula III, or pharmaceutically acceptable salt thereof:

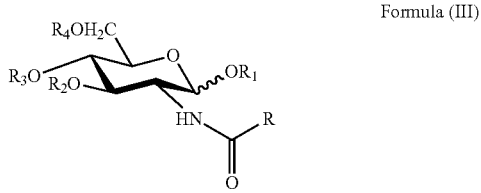

Formula (III)

wherein,
each of $R_1$, $R_2$, $R_3$, and $R_4$ is independently H, —C(O)alkyl or —C(O)(CH$_2$)$_n$CH$_3$;
wherein at least one $R_1$, $R_2$, $R_3$, and $R_4$ is H and at least one $R_1$, $R_2$, $R_3$, and $R_4$ is —C(O)alkyl or —C(O)(CH$_2$)$_n$CH$_3$;
each n is independently an integer from 0-18; and
R is alkyl or alkenyl, each of which is optionally substituted with 1-4 substituents selected from acyl, oxo, azido, aryl, halogen, —OC(O)alkyl, or —SC(O)alkyl.

In certain embodiments, R is alkyl or substituted alkyl substituted by azido, oxo, —OC(O)alkyl, or —SC(O)alkyl, $R_1$ is H, and $R_2$, $R_3$, and $R_4$ are each independently —C(O)(CH$_2$)$_n$CH$_3$.

In another embodiment, R is alkyl or substituted alkyl substituted by azido, oxo, —OC(O)alkyl, or —SC(O)alkyl, $R_2$ is H, and $R_1$, $R_3$, and $R_4$ are each independently —C(O)(CH$_2$)$_n$CH$_3$.

In still other embodiments, R is alkyl or substituted alkyl substituted by azido, oxo, —OC(O)alkyl, or —SC(O)alkyl, $R_3$ is H, and $R_1$, $R_2$, and $R_4$ are each independently —C(O)(CH$_2$)$_n$CH$_3$.

In another embodiment, R is alkyl or substituted alkyl substituted by azido, oxo, —OC(O)alkyl, or —SC(O)alkyl, $R_4$ is H, and $R_1$, $R_2$, and $R_3$ are each independently —C(O)(CH$_2$)$_n$CH$_3$.

In one embodiment, the invention provides a compound of formula IV, or pharmaceutically acceptable salt thereof:

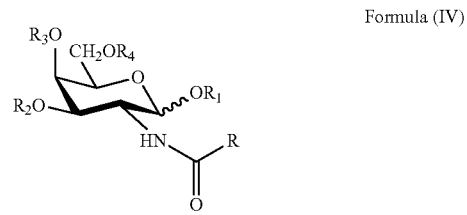

Formula (IV)

wherein,
each of $R_1$, $R_2$, $R_3$, and $R_4$ is independently H, —C(O)alkyl or —C(O)(CH$_2$)$_n$CH$_3$;
wherein at least one $R_1$, $R_2$, $R_3$, and $R_4$ is H and at least one $R_1$, $R_2$, $R_3$, and $R_4$ is —C(O)alkyl or —C(O)(CH$_2$)$_n$CH$_3$;
each n is independently an integer from 0-18; and
R is alkyl or alkenyl, each of which is optionally substituted with 1-4 substituents selected from acyl, oxo, azido, aryl, halogen, —OC(O)alkyl, or —SC(O)alkyl.

In one embodiment, R is alkyl, and $R_1$, $R_2$, $R_3$, and $R_4$ are each independently —C(O)(CH$_2$)$_n$CH$_3$.

In another embodiment, R is alkyl, $R_1$ is H, and $R_2$, $R_3$, and $R_4$ are each independently —C(O)(CH$_2$)$_n$CH$_3$.

In other embodiment, R is alkyl, $R_2$ is H, and $R_1$, $R_3$, and $R_4$ are each independently —C(O)(CH$_2$)$_n$CH$_3$.

In another embodiment, R is alkyl, $R_3$ is H, and $R_1$, $R_2$, and $R_4$ are each independently —C(O)(CH$_2$)$_n$CH$_3$.

In still another embodiment, R is alkyl, $R_4$ is H, and $R_1$, $R_2$, and $R_3$ are each independently —C(O)(CH$_2$)$_n$CH$_3$.

In a further embodiment, R is alkyl or a substituted alkyl substituted with azido, oxo, —OC(O)alkyl, or SC(O)alkyl, $R_1$ is H, and $R_2$, $R_3$, and $R_4$ are each independently —C(O)(CH$_2$)$_n$CH$_3$.

In another embodiment, R is alkyl or a substituted alkyl substituted with azido, oxo, —OC(O)alkyl, or SC(O)alkyl, $R_4$ is H, and $R_1$, $R_2$, and $R_3$ are each independently —C(O)(CH$_2$)$_n$CH$_3$.

In another aspect, the invention provides a compound of formula V:

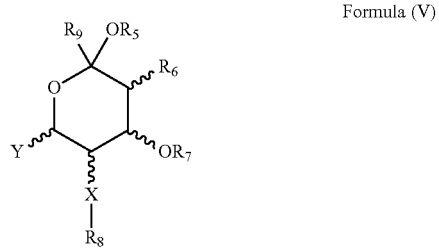

Formula (V)

wherein,
Y is alkyl, alkenyl, alkynyl, aryl, heteroaryl, cycloalkyl, heterocycloalkyl, aralkyl, or heteroaralkyl; each of which may be optionally substituted by 1-3 groups selected from alkyl, alkoxy, aryl, heteroaryl, aralkyl, heteroaralkyl, hal, nitro, cyano, and acyl;
X is O, NH, or NR$_4$;
each of $R_5$ and $R_7$ is independently H, —C(O)alkyl or —C(O)(CH$_2$)$_n$CH$_3$;
$R_6$ is OH, —OC(O)alkyl or —OC(O)(CH$_2$)$_n$CH$_3$;
$R_8$ is H, —C(O)alkyl or —C(O)(CH$_2$)$_n$CH$_3$;

$R_9$ is H, alkyl, C(O)$R_A$, C(O)O$R_A$, or C(O)N$R_A R_A$; and
$R_A$ is H or alkyl.

In one embodiment, the invention provides a compound of formula VI:

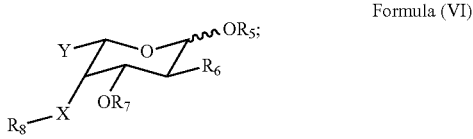

Formula (VI)

wherein,
Y is alkyl, alkenyl, alkynyl, aryl, heteroaryl, cycloalkyl, heterocycloalkyl, aralkyl, or heteroaralkyl; each of which may be optionally substituted by 1-3 groups selected from alkyl, alkoxy, aryl, heteroaryl, aralkyl, heteroaralkyl, hal, nitro, cyano, and acyl;
X is O;
each of $R_5$ and $R_7$ is independently H, —C(O)alkyl or —C(O)(CH$_2$)$_n$CH$_3$;
$R_6$ is OH, —OC(O)alkyl or —OC(O)(CH$_2$)$_n$CH$_3$; and
$R_8$ is —C(O)alkyl or —C(O)(CH$_2$)$_n$CH$_3$.

In another embodiment, the invention provides a compound of formula VII:

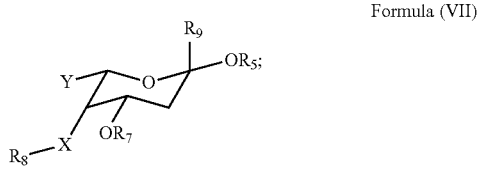

Formula (VII)

wherein,
Y is alkyl, aryl, heteroaryl, cycloalkyl, heterocycloalkyl, aralkyl, or heteroaralkyl; each of which may be optionally substituted by 1-3 groups selected from alkyl, alkoxy, aryl, heteroaryl, aralkyl, heteroaralkyl, hal, nitro, cyano, and acyl;
X is NH or N$R_A$;
each of $R_5$ and $R_7$ is independently H, —C(O)alkyl or —C(O)(CH$_2$)$_n$CH$_3$;
$R_8$ is —C(O)alkyl or —C(O)(CH$_2$)$_n$CH$_3$;
$R_9$ is alkyl, C(O)$R_A$, C(O)O$R_A$, or C(O)N$R_A R_A$; and
$R_A$ is H or alkyl.

In certain embodiments, Y is alkyl, substituted by 1-3 groups selected from alkyl, alkoxy, aryl, heteroaryl, aralkyl, heteroaralkyl, hal, nitro, cyano, or acyl.

In certain embodiments, the invention provides for a compound of formula

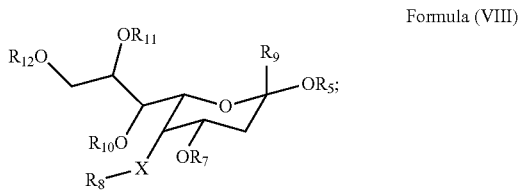

Formula (VIII)

wherein,
each of $R_{11}$, $R_{12}$ and $R_{13}$ are independently H, —C(O)alkyl or —C(O)(CH$_2$)$_n$CH$_3$;
wherein at least one $R_{11}$, $R_{12}$ and $R_{13}$ is H and at least one $R_{11}$, $R_{12}$ and $R_{13}$ is —C(O)alkyl or —C(O)(CH$_2$)$_n$CH$_3$;

wherein X, $R_5$, $R_7$, $R_8$, $R_9$ and $R_A$ have been previously described.

In another aspect, the invention provides a pharmaceutical composition comprising a compound of formula I or formula V, and a pharmaceutically acceptable carrier.

In one embodiment, the pharmaceutical composition further comprises an additional therapeutic agent.

In a further embodiment, the additional therapeutic agent is an anticancer agent.

In another embodiment, the invention provides a compound which is a potential pharmaceutical target for cancer diseases.

In other embodiments, the invention provides a compound which comprises mix-match substitution.

In another embodiment, the compound is utilized in metabolic labeling of proteins.

In another embodiment, the compound is utilized in stem cell differentiation.

In one aspect, the invention provides a method of treating or preventing a subject suffering from or susceptible to a disease or disorder, the method comprising the step of administering to the subject a therapeutic amount of a compound of formula I or formula V, sufficient to treat the disease or disorder or symptoms thereof under conditions such that the disease or disorder is treated.

In another aspect, the invention provides a method of treating or preventing a subject suffering from or susceptible to a disease or disorder, the method comprising the steps of: (i) identifying the patient as in need of administration of a MUC1, MMP9, CXCR4, or NF-κB inhibitor compound; and (ii) administering to the subject a therapeutic amount of a compound of formula I or formula V sufficient to treat or prevent the disease or disorder or symptoms thereof.

In one embodiment, the subject is a human.

In other embodiments, the invention provides a method, further comprising administering an additional therapeutic agent.

In certain embodiments, the additional agent is an anticancer agent.

In one embodiment, the additional agent is an antiangiogenesis agent, selective estrogen-receptor modulator (SERM), aromatase inhibitor, biologic response modifiers, hormonal therapies agent, anthracycline, taxane, alkylating agent, taxol, cis-platin, arabinofuranosyl cytosine (ara-C), 5-fluorouracil (5-FU), altretamine, busulfan, chlorambucil, cyclophosphamide, ifosfamide, mechlorethamine, melphalan, thiotepa, cladribine, fluorouracil, floxuridine, gemcitabine, thioguanine, pentostatin, methotrexate, 6-mercaptopurine, cytarabine, carmustine, lomustine, streptozotocin, carboplatin, oxaliplatin, iproplatin, tetraplatin, lobaplatin, JM216, JM335, fludarabine, aminoglutethimide, flutamide, goserelin, leuprolide, megestrol acetate, cyproterone acetate, tamoxifen, anastrozole, bicalutamide, dexamethasone, diethylstilbestrol, prednisone, bleomycin, dactinomycin, daunorubicin, doxirubicin, idarubicin, mitoxantrone, losoxantrone, mitomycin-c, plicamycin, paclitaxel, docetaxel, CPI-11, epothilones, topotecan, irinotecan, 9-amino camptothecan, 9-nitro camptothecan, GS-211, etoposide, teniposide, vinblastine, vincristine, vinorelbine, procarbazine, asparaginase, pegaspargase, methoxtrexate, octreotide, estramustine, hydroxyurea, tamoxifen, raloxifene, toremifene, exemestane, letrozole, anastrozole, megestrol, trastuzumab, goserelin acetate, fulvestrant, doxorubicin, epirubicin, or cyclophosphonamide.

In one embodiment, the subject is suffering from a cell proliferation disease or disorder.

One aspect is a method of treating a subject suffering from or susceptible to a disease or disorder, or symptom thereof, or preventing a disease or disorder, or symptom thereof, in a subject susceptible to a disease or disorder, or symptom thereof, or reducing the risk of development in a subject of a disease or disorder, or symptom thereof. The method includes the step of administering to the subject a therapeutic amount of a compound herein sufficient to treat the disease or disorder or symptom thereof under conditions such that the disease or disorder or symptom thereof is treated. In certain embodiments, the disease or disorder is a cancer or proliferative disease or disorder. In certain embodiments, the subject is a human. In certain embodiments, the subject is identified as being in need of such treatment. In certain embodiments, the subject is not suffering from a cancer. In certain embodiments, the subject is "at risk" of developing cancer. In certain embodiments, the method includes administration of an additional therapeutic agent. In certain embodiments, the step of administering comprises administering the compound orally, intravenously or intramuscularly.

As noted, diseases, disorders or symptoms thereof of specific interest include cancer, those wherein proliferation may be implicated. Specifically, cancers or proliferative disorders include breast, prostate, lung, colon, liver, solid tumor, myeloma, leukemia, bladder, stomach, and the like; diseases, disorders or symptoms thereof, or diseases, disorders or symptoms thereof wherein targets and/or substrates associated with the diseases, disorders or symptoms thereof are mediated by cell cycle inhibition (e.g., HDAC inhibition) and/or abnormal glycosylation modulation (e.g., sialic acid biosynthesis).

In another embodiment, the subject is administered the compound of formula I or formula V orally, topically, parentally, intravenously or intramuscularly.

In another embodiment, the step of administering the compound comprises administering the compound in a dosage of between about 0.001 and 300 mg/kg/day.

In other embodiments, the disease, disorder, or symptom thereof is cancer.

In one aspect, the invention provides a method of sensitizing a cancer cell in a subject to anticancer agents, the method comprising the steps of identifying a subject as in need thereof and administering to the subject a therapeutic amount of a compound of formula I or formula V, sufficient to sensitizing a cancer cell in a subject to anticancer agents.

In another aspect, the invention provides a method of treating or preventing cancer in a subject, the method comprising the step of administering to the subject a therapeutic amount of a compound of formula I or formula V.

In certain embodiments, the cancer is brain tumor, leukemia, lymphoma, colon cancer, breast cancer, lung cancer, prostate cancer, cervical cancer, bladder cancer, or thyroid cancer.

In another aspect, the invention provides a method of treating or preventing cancer in a subject, with reduced toxicity, the method comprising the steps of administering to the subject a therapeutic amount of a compound of formula I or formula V.

In certain embodiments, the toxicity of the compound of formula (I) is ranges from nanomolar (nM) to micromolar (µM) concentration of the compounds of the invention.

Other aspects include applications related to the compounds of the formulae herein used to treat neural or neurodegenerative or psychotic disorders. Other aspects include applications related to the compounds of the formulae herein (e.g., Bu$_4$GlcNAc) used as a control for ManNAc-sialic acid effects. The sugar GlcNAc is known to be pro-survival under stress conditions and Bu4GlcNAc has potential applications for enhanced delivery of GlcNAc—a C-2 epimer of ManNAc—along with concomitant effects on cell cycle arrest or tumor growth arrest.

The methods include administration of the compound or composition thereof to a subject in need (e.g., identified as in need) of such treatment Another aspect is a method to extend the lifetime of a subject who is refractory to current anti-cancer chemotherapy and to improve the quality of life for those subjects. Such method includes the steps of identifying a subject as in need thereof and administering to the subject a therapeutic amount of a compound of the formulae herein sufficient to prevent, reduce or ameliorate metastasis of cancer.

A method of treating or preventing a subject suffering from or susceptible to a disease or disorder, the method comprising the steps of: (i) identifying the patient as one who may benefit from cell cycle inhibition (e.g., HDAC inhibition) and/or abnormal glycosylation modulation (e.g., sialic acid biosynthesis); and (ii) administering to the subject a therapeutic amount of a compound of the formulae herein sufficient to treat or prevent the disease or disorder or symptoms thereof under conditions such that the disease or disorder is treated or prevented or prevented from further progression.

In another aspect, the invention provides a method of a incorporating a compound of formula I or formula V in a glycan cell surface or in a glycosylation pathway, wherein toxicity is reduced.

In another aspect, the invention provides a method of a incorporating a compound of formula I or formula V in a glycan cell surface or in a glycosylation pathway, wherein toxicity is absent.

In one aspect, the invention provides a method of stimulating an immune system in a subject suffering from or susceptible to cancer, the method comprising the step of administering to the subject an effective amount of a compound of formula I or formula V, such that the immune system is stimulated.

In one aspect, the invention provides a kit comprising an effective amount of a compound of formula I or formula V in unit dosage form, together with instructions for administering the compound to a subject suffering from or susceptible to a cancer disease or disorder or symptoms thereof.

In another aspect, the invention provides a method of treating or preventing a disease or disorder selected from multiple sclerosis, Crohn's disease, rheumatoid arthritis, fibrosis, myocardial infarction, osteoid arthritis, Kaposi's sarcoma-associated herpes virus, Parkinson's disease, Huntington's disease, spinal muscular atrophy (increase survival motor neuron protein), cystic fibrosis, ulcerative colitis, antibiotic-associated diarrhea, stem cell fate and regenerative medicine, immune disorders, congenital abnormalities, infectious diseases and related diseases in a subject, the method comprising the steps of identifying a subject as in need thereof and administering to the subject a therapeutic amount of a compound of formula I or formula V sufficient to treat or prevent the disease or disorder.

Another aspect of the invention is the use of a compound of the invention in the manufacture of a medicament for treatment or prevention in a subject of a disease, disorder or symptom thereof delineated herein.

In another aspect, the invention provides a method of inducing apoptosis in a subject, the method comprising the steps of identifying a subject as in need thereof and administering to the subject a therapeutic amount of a compound of formula I or formula V capable of inducing apoptosis.

In another aspect, the invention provides a method of inducing apoptosis in a subject, the method comprising the steps of identifying a subject as in need thereof and administering to the subject a therapeutic amount of a compound of formula I or formula V capable of inducing apoptosis and activating sialic acid biosynthesis.

In another aspect, the invention provides a method of modulating gene expression (e.g., p21WAF1/Cip1) in a subject, the method comprising the steps of identifying a subject as in need thereof and administering to the subject a therapeutic amount of a compound of formula I or formula V sufficient to modulate the protein (e.g., p21WAF1/Cip1).

In other aspects, the invention provides a method of modulating sialyltransferase activity in a subject, the method comprising the steps of identifying a subject as in need thereof and administering to the subject a therapeutic amount of a compound of formula I or formula V sufficient to modulate the sialyltransferase activity.

The invention provides a method of increasing the flux through the sialic acid biosynthetic pathway and increasing the biological production of sialic acid or its non-natural epitopes in sialic acid deficiency diseases (HIBM, stem cell development—genetic diseases) in a subject, the method comprising the steps of identifying a subject as in need thereof and administering to the subject a therapeutic amount of a compound herein sufficient to increasing the flux through the sialic acid biosynthetic pathway and increasing the biological production of sialic acid or its non-natural epitopes in sialic acid deficiency diseases.

The invention provides a method by which to diagnose cytochemically or histochemically or histopathologically or immunocyto or immuno-histochemically, the modifications consequent to the expression of thiols on sialic acids; comprising the steps of assessing modulation of a target or process delineated herein.

In one embodiment, the modulation is up regulation.

In one aspect, the invention provides a method of modulating a target, including a cell cycle checkpoint protein, programmed cell death substrate, or a kinase identified herein, in a cell comprising contacting a compound of formula I or formula V with a target (e.g., in a subject, in a cell, in vitro) such that the target is modulated.

In another aspect, the invention provides a method of drug delivery, gene delivery or MRI delivery, comprising the step of contacting a compound of formula I or formula V to a delivery location in vivo.

In certain embodiments, the method further includes the step of determining a level of a marker in the subject. In certain embodiments, the step of determining of the level of Marker is performed prior to administration of the compound of the formulae hereinto the subject. In certain embodiments, the determining of the level of Marker is performed subsequent to administration of the compound of the formulae hereinto the subject. In certain embodiments, the determining of the level of Marker is performed prior to and subsequent to administration of the compound of the formulae hereinto the subject. In certain embodiments, the levels of Marker performed prior to and subsequent to administration of the compound of the formulae hereinto the subject are compared. In certain embodiments, the comparison of Marker levels is reported by a clinic, laboratory, or hospital agent to a health care professional. In certain embodiments, when the level of Marker performed prior to administration of the compound of the formulae hereinto the subject is lower or higher (depending on the Marker) than the level of Marker performed subsequent to administration of the compound of the formulae hereinto the subject, then the amount of compound administered to the subject is an effective amount. The Marker can be any characteristic or identifier, including for example, a chemical, a fluid, a protein, gene, promoter, enzyme, protein, labeled molecule, tagged molecule, antibody, and the like (e.g., HDAC, p21, glycosylation, BAX, sialyltransferase, sialidase, phosphorylation of a kinase, polysialic acid, sialyl Lewis X, gangliosides, chemical epitopes such as thiols, ketones and azides; the expression of genes, including the following, —MUC1, MUC18, galectin 3, galectin 12, galectin-related inhibitor of proliferation isoform b, chondroitin 6-sulfo T, MUC1-transmembrane, COG7, interferon induced transmembrane protein 1 (9-27), anaphase promoting complex subunit 5 (ANAPC5), sperm associated antigen 7 (SPAG7), proteasome activator subunit 1 (pA28 alpha), heparanase, melanoma cell adhesion molecule (short transcript), serglycin, syndecan 4 (ryudocan), ppGalNAc T11, xylosyltransferase II 9XT-II) [GAG enzyme], similar to glucosamine-phosphate N-acetyltransferase (short), gp130-RAPS, erythropoietin receptor, insulin-like GF 2 receptor, insulin-like GF 3, TGF, beta receptor III and follistatin isoform FST317 precursor.

In certain method embodiments, a level of Marker or Marker activity in a subject is determined at least once. Comparison of Marker levels, e.g., to another measurement of Marker level obtained previously or subsequently from the same patient, another patient, or a normal subject, may be useful in determining whether therapy according to the invention is having the desired effect, and thereby permitting adjustment of dosage levels as appropriate. Determination of Marker levels may be performed using any suitable sampling/expression assay method known in the art or described herein. Preferably, a tissue or fluid sample is first removed from a subject. Examples of suitable samples include blood, mouth or cheek cells, and hair samples containing roots. Other suitable samples would be known to the person skilled in the art. Determination of protein levels, glycolipid (gangliosides) levels (by HPTLC) and/or mRNA levels (e.g., Marker levels) in the sample can be performed using any suitable technique known in the art, including, but not limited to, enzyme immunoassay, ELISA, radiolabelling/assay techniques, blotting/chemiluminescence methods, real-time PCR, and the like.

In one embodiment, the invention provides a method of monitoring treatment progress. The method includes the step of determining a level of diagnostic marker (Marker) (e.g., any target delineated herein modulated by a compound herein) or diagnostic measurement (e.g., screen, assay) in a subject suffering from or susceptible to a disorder or symptoms thereof associated with disease (e.g., cancer or other disease herein), in which the subject has been administered a therapeutic amount of a compound herein sufficient to treat the disease or symptoms thereof. The level of Marker determined in the method can be compared to known levels of Marker in either healthy normal controls or in other afflicted patients to establish the subject's disease status. In preferred embodiments, a second level of Marker in the subject is determined at a time point later than the determination of the first level, and the two levels are compared to monitor the course of disease or the efficacy of the therapy. In certain preferred embodiments, a pre-treatment level of Marker in the subject is determined prior to beginning treatment according to this invention; this pre-treatment level of Marker can then be compared to the level of Marker in the subject after the treatment commences, to determine the efficacy of the treatment. The comparison of marker levels is reported by a clinic, laboratory, or hospital agent to a health care professional.

When the level of marker prior to administration of the compound to the subject is lower (or higher depending on the function being assessed) than the level of marker subsequent to administration of the compound to the subject, then the amount of compound administered to the subject is an effective amount.

In other method embodiments, the levels of metabolites from the inhibitor compounds can be assessed. For example, the methods can further include assessment of levels of inhibitors or inhibitor derivatives (or metabolites thereof) resulting from the inhibitor compounds or inhibitor derivative compounds, including those of the formulae herein. Parameters such as the subject identification or selection for the treatment regimen, treatment efficacy, treatment protocol status or dosage range can be determined using these measurements.

Another aspect is a method of impairing abnormal remodeling of the extracellular matrix by diseased or injured cells (fibroblasts) in a subject, the method comprising the steps of identifying a subject as in need thereof and administering to the subject a therapeutic amount of a compound of the formulae herein sufficient to impair abnormal remodeling of the extracellular matrix by diseased or injured cells. Such method is relevant as a method to treat myocardial infarction, osteoid and rheumatoid arthritis, and fibrosis.

Another aspect is a method of impairing invasiveness and motility of abnormal cells that infiltrate diseased tissue (e.g., cancer cells or autoreactive immune cells) in a subject, the method comprising the steps of identifying a subject as in need thereof and administering to the subject a therapeutic amount of a compound of the formulae herein sufficient to impair invasiveness and motility of abnormal cells that infiltrate diseased tissue. Such method is relevant as a method to treat or prevent metastatic cancer, rheumatoid arthritis, Crohn's disease, and multiple sclerosis.

Another aspect is a method of sensitizing a cancer cell in a subject to an anticancer agent or DNA targeted agent (e.g., chemotherapeutic), the method comprising the steps of identifying a subject as in need thereof and administering to the subject a therapeutic amount of a compound of the formulae herein sufficient to sensitizing a cancer cell in a subject to an anticancer agent or DNA targeted agent.

Another aspect is a method of modulating a protein or gene capable of expressing such protein (e.g., HDAC, p21, BAX, MMPs (matrix metalloproteinases), NF-κB, AP-1, β-catenin, phosphatidyl serine, MUC1, MUC18, galectin 3, galectin 12, galectin-related inhibitor of proliferation isoform b, chondroitin 6-sulfo T, MUC1-transmembrane, COG7, interferon induced transmembrane protein 1 (9-27), anaphase promoting complex subunit 5 (ANAPC5), sperm associated antigen 7 (SPAG7), proteasome activator subunit 1 (pA28 alpha), heparanase, melanoma cell adhesion molecule (short transcript), serglycin, syndecan 4 (ryudocan), ppGalNAc T11, xylosyltransferase II 9XT-II) [GAG enzyme], similar to glucosamine-phosphate N-acetyltransferase (short), gp130-RAPS, erythropoietin receptor, insulin-like GF 2 receptor, insulin-like GF 3, TGF, beta receptor III and follistatin isoform FST317 precursor.) in a subject, the method comprising the steps of identifying a subject as in need thereof and administering to the subject a therapeutic amount of a compound of the formulae herein sufficient to modulate the protein or gene capable of expressing such protein (e.g., HDAC, p21, BAX, MMPs (matrix metalloproteinases), NF-κB, AP-1, β-catenin, phosphatidyl serine, MUC1, MUC18, galectin 3, galectin 12, galectin-related inhibitor of proliferation isoform b, chondroitin 6-sulfo T, MUC1-transmembrane, COG7, interferon induced transmembrane protein 1 (9-27), anaphase promoting complex subunit 5 (ANAPC5), sperm associated antigen 7 (SPAG7), proteasome activator subunit 1 (pA28 alpha), heparanase, melanoma cell adhesion molecule (short transcript), serglycin, syndecan 4 (ryudocan), ppGalNAc T11, xylosyltransferase II 9XT-II) [GAG enzyme], similar to glucosamine-phosphate N-acetyltransferase (short), gp130-RAPS, erythropoietin receptor, insulin-like GF 2 receptor, insulin-like GF 3, TGF, beta receptor III and follistatin isoform FST317 precursor).

Another aspect is a method of modulating HDAC and/or glycosylation in a subject, the method comprising the steps of identifying a subject as in need thereof and administering to the subject a therapeutic amount of a compound of any of the formulae herein sufficient to modulate HDAC and/or glycosylation under conditions such that the HDAC and/or glycosylation is modulated. In one aspect, the modulation is down regulation of HDAC. In another aspect, the modulation is up regulation of biosynthesis of sialic acids.

Another aspect is a method of modulating a target, including a cell cycle checkpoint protein, programmed cell death substrate, or a kinase identified herein, in a cell comprising contacting a compound of any of the formulae herein with a target (e.g., in a subject, in a cell, in vitro) such that the target is modulated. The method can also include modulating the target in a subject by administering the compound to the subject.

BRIEF DESCRIPTION OF THE DRAWINGS

FIG. 9. Partially-acylated SCFA-Monosaccharide Hybrid Molecules. (A) A ManNAc scaffold providing substitution patterns of compounds of the invention; (B) Additional monosaccharide scaffolds comprising substitution patterns of the compounds of the invention.

FIG. 10. Biological responses determined by the SAR of partially SCFA-derivatized and partially hydroxyl-substituted ManNAc extend to other hexosamine "scaffolds" as demonstrated by GlcNAc analogs. (A) Structures of analogs 13, 14, and 15. (B) Growth inhibition after 3 days and (C) cytotoxicity after 15 days shows a pattern where C6-OH substitution with a SCFA is required for toxicity in a manner set by the ManNAc analogs (a similar response is observed for GalNAc-based analogs, data not shown). (D) Extending the SAR to non-natural "R" groups is shown with the ketone group of "Lev" analogs and (E) the azide group of "Az" analogs.

FIG. 13. SCFA-Monosaccharide Hybrid Molecules with More Than One Type of ester-linked SCFA group. (A) compounds of the invention having distinct substitution groups based on the ManNAc formula or (B) structure-activity relationships for attaching different SCFAs to another monosaccharide 'scaffold' to generate novel biological activity (as shown by the data presented in FIG. 12).

DETAILED DESCRIPTION OF THE INVENTION

Figure 1:
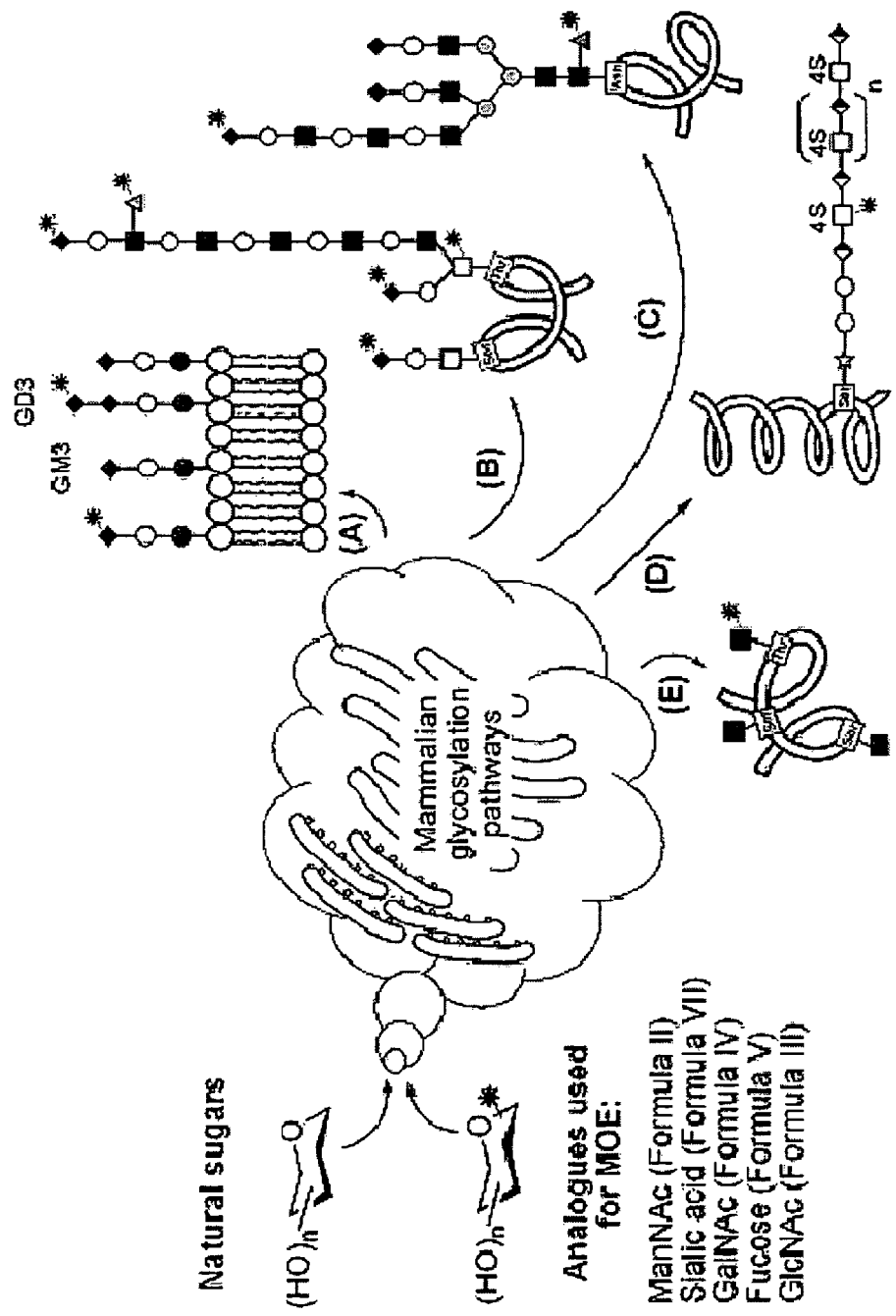
FIG. 1. Overview of Metabolic Oligosaccharide Engineering (MOE). Non-natural chemical analogs of monosaccharides intercept glycosylation pathways in the place of the corresponding natural sugars and are biosynthetically incorporated into various classes of complex carbohydrate macromolecules including (A) glycosphingolipids, (B) O-linked glycoproteins, (C) N-linked glycoproteins, (D) glycosoaminoglycans, and (E) O-GlcNAc-modified nuclear and cytosolic proteins. Non-natural sugars are schematically represented by a starburst symbol. To date, analogs of ManNAc, sialic acid, GalNAc, fucose, and GlcNAc have proved suitable for use in MOE experiments, the structural variants of these analogs are shown in Formula I through VII in the text and Drawings 9 and 13.

This invention solves two problems inherent with the use of SCFA-monosaccharide hybrid molecules to modulate cellular activity. The first problem is the toxicity of former versions of these compounds; the current invention uses structure activity relationships as it has been discovered to either enhance or avoid toxicity (depending on the intended application). A second problem is that these compounds have a diverse set of biological activities; the current invention allows specific activities to be deconvoluted and selectively controlled; as a consequence better control can be gained over the biological responses elicited by these compounds. Two such applications described herein are control of stem cell differentiation and reduced invasiveness of cancer cells, e.g., metastatic breast cancer cells.

This invention elaborates the installation of appended short chain fatty acids (SCFAs) to monosaccharide analogs in 'metabolic oligosaccharide engineering' (MOE) to create SCFA-sugar hybrid molecules. The original compounds were fully derivatized with acetate, the smallest SCFA, with the intent to increase membrane permeability and cellular uptake.

A problem with previous work was the toxicity of these compounds that restricted certain applications (such as tissue engineering and regenerative medicine where high cell viability is important).

Because of the toxicity of certain SCFA-monosaccharide hybrid molecules, it was postulated that these compounds might comprise a novel set of cancer drugs; however the toxicity was relatively mild (i.e., in the micromolar, instead of the nanomolar, range) compared to that of most cancer drugs. Therefore instead of using acetate, a weakly active SCFA, a butyrate was appended, a highly active SCFA, to hexosamines and demonstrated improved effectiveness against cancer cells.

The current strategy deviates from the previous approach of using fully SCFA-derivatized sugar analogs to selective placement of SCFA groups on the monosaccharide scaffold. This approach takes two directions. First, specific hydroxyl groups of the carbohydrate are left underivatized with a SCFA (i.e., they remain as a hydroxyl group). Second, a 'mix-and-match' approach has been used where more than one type of SCFA is attached to the same sugar scaffold. In both cases, unique biological responses are obtained not seen with the unattached constituent molecules (even when they are used in combination) or the uniformly-derivatized SCFA-monosaccharides previously reported.

By using this approach, toxicity can be both enhanced (which is beneficial for cancer drug development) or avoided (which is beneficial for a host of applications where MOE is not intended to kill the target cells). Consequently, this invention opens the door to a significant number of MOE applications where toxicity (1) is either not required or (2) is overtly deleterious. We have now demonstrated an example of each situation by (1) showing that butyrate-ManNAc hybrid molecules inhibit invasion at subtoxic doses thereby establishing that these compounds may serve as anti-metastatic cancer drugs (in addition to previous efforts to kill cancer cells) and (2) showing that 'Ac$_5$ManNTGc' can control the fate of stem cells.

ManNAc has several attractive features that led us to select it as an hexosamine for use in butyrate-sugar hybrid drug development. First, it is a committed precursor for the sialic acid biosynthetic pathway and has no other known metabolic roles, thereby allowing a specific and unique biochemical pathway to be targeted. Second, uptake of exogenous ManNAc alters flux through the sialic acid biosynthetic pathway and changes sialyltransferase and sialidase activity thereby altering the display of sialic acid on cell surface glycoproteins and glycolipids. Because these sialoglycans modulate apoptosis, it was hypothesized that an n-butyrate prodrug with ManNAc as an active carrier would both "arrest" and "execute" cancer cells via SCFA-mediated cell cycle inhibition and ManNAc-augmented apoptosis, respectively. The results verified this hypothesis by demonstrating that butyrate gains a unique ability to induce apoptosis when presented to cells as the hybrid molecule "Bu$_4$ManNAc." It is also confirmed that this molecule has characteristic SCFA activity and activates sialic acid biosynthesis, as expected of each of its functional moieties. In concurrent control experiments, delivery of n-butyrate via other carbohydrate scaffolds only achieved transient inhibition of cell growth and thereby illustrated the necessity of targeting a specific glycosylation pathway—sialic acid biosynthesis—to achieve synergistic toxicity against cancer cells not seen with either the SCFA or sugar functionality alone.

The invention relates to short chain fatty acid (SCFA)-hexosamine hybrid molecules that target both histone deacetylation and glycosylation pathways to achieve synergistic killing modalities against human cancer cells. Specifically, n-butyrate esters of N-acetyl-D-mannosamine (Bu$_4$ManNAc) efficiently induced apoptosis. These findings establish that n-butyrate, when delivered to cells via any carbohydrate scaffold, can function as a histone deacetylase inhibitor (HDACi), up-regulate p21$^{WAF1/Cip1}$-driven gene expression, and inhibit proliferation. However only Bu$_4$ManNAc, a compound that primes sialic acid biosynthesis in addition to functioning as an HDACi, ultimately killed the cells thereby demonstrating that the core sugar moiety plays a key role in augmenting the bioactivity of butyrate. Post translational O-GlcNAc modification of proteins at serine/threonine side chains.

The cytoplasmic and nuclear proteins are modified post-translationally by phosphorylation and glycosylation at the amino acid side chains which act as triggers of signal transduction. The O-GlcNAc (N-acetyl-D-glucosamine) modification is found on the same serine residue under certain conditions that are also modified by phosphorylation at other conditions, known as the 'ying-yang' hypothesis (ref: Zachara, N. E., Hart, G. W., Chem. Rev. 102, 431-438 (2002). The emerging significance of O-GlcNAc in cellular regulation; 2. Slawson, C., Housley, M. P., Hart, G. W., J. Cell Biochem. 97, 71-83 (2006). O-GlcNAc cycling: how a single sugar post-translational modification is changing our understanding about signaling networks.

Protein phosphorylation is a key event in many signaling events. O-GlcNAc attachment can prevent or compete with protein phosphorylation and hence regulate signaling networks. Cellular O-GlcNAc modification level is up regulated under stress conditions (heat, toxic metal, oxidative stress) and is generally considered as a pro-survival mechanism of cells.

External delivery of GlcNAc can increase levels of protein O-GlcNAc modification, but, the intracellular delivery of the hydrophilic free monosaccharide GlcNAc is inefficient, usually requiring millimolar quantities. The novel hydrophobic analog 'Bu$_4$GlcNAc' reported here can enhance cellular uptake and act as an efficient prodrug for GlcNAc, requiring only micromolar levels.

Compounds

The compounds of the invention provided high sialic acid flux having both natural and unnatural cell surface glycan, and is of great interest in diseases like Hereditary Inclusion Body Myopathy (HIBM) because this disease occurs due to less sialic acid on their surface due to mutation.

Additionally, the compounds of the invention are valuable targets for the development of carbohydrate based vaccine for cancer, influenza or HIV on the concept of glycoengineering and immunology Additional compounds of the invention are applicable in the study of glycosylation of nuclear or cytosolic proteins, which contribute towards the design of drugs or vaccines for deadly disease like diabetes, or Parkinsons or Alzheimer's.

The compounds of the invention may have a divergent impact on transcription, and are linked to the interplay between the HDACi and NF-κB activity, which was selectively down regulated by these compounds Another aspect is a radio labeled compound of any of the formulae delineated herein. Such compounds have one or more radioactive atoms or heavy atom isotopes (e.g., $^3$H, $^2$H, $^{14}$C, $^{13}$C, $^{35}$S, $^{125}$I, $^{131}$I, $^{18}$O, $^{17}$O, $^{19}$F for PET applications) introduced into the compound. Such compounds are useful for drug metabolism studies and diagnostics.

As used herein, the term "alkyl" refers to a straight-chained or branched hydrocarbon group containing 1 to 18 (e.g., C1-C-18, inclusive; and any sub-range thereof) carbon atoms.

The term "lower alkyl" refers to a C1-C6 alkyl chain. Examples of alkyl groups include methyl, ethyl, n-propyl, isopropyl, n-butyl, sec-butyl, tert-butyl, pentyl (n-, sec-, tert-), and pivaloyl. Alkyl groups may be optionally substituted with one or more substituents.

The term "alkenyl" refers to an unsaturated hydrocarbon chain that may be a straight chain or branched chain, containing 2 to 12 carbon atoms and at least one carbon-carbon double bond. Alkenyl groups may be optionally substituted with one or more substituents.

The term "alkynyl" refers to an unsaturated hydrocarbon chain that may be a straight chain or branched chain, containing the 2 to 12 carbon atoms and at least one carbon-carbon triple bond. Alkynyl groups may be optionally substituted with one or more substituents.

The $sp^2$ or sp carbons of an alkenyl group and an alkynyl group, respectively, may optionally be the point of attachment of the alkenyl or alkynyl groups.

The term "alkoxy" refers to an —O-alkyl substituent group. The term "ester" refers to a —C(O)O—R, wherein R is as defined herein. An "amido" is an —C(O)NH$_2$, and an "N-alkyl-substituted amido" is of the formula C(O)NHR, wherein R is as defined herein.

The term "mercapto" refers to a —SH group.

As used herein, the term "halogen" or "halo" means —F, —Cl, —Br or —I.

As used herein, the term "haloalkyl" means and alkyl group in which one or more (including all) the hydrogen radicals are replaced by a halo group, wherein each halo group is independently selected from —F, —Cl, —Br, and —I. The term "halomethyl" means a methyl in which one to three hydrogen radical(s) have been replaced by a halo group. Representative haloalkyl groups include trifluoromethyl, difluoromethyl, bromomethyl, 1,2-dichloroethyl, 4-iodobutyl, 2-fluoropentyl, and the like. The term "perhaloalkyl" refers to a alkyl group in which all hydrogen atoms are replaced by a halo group (e.g., trifluoromethyl, pentafluoroethyl).

The term "cycloalkyl" refers to a hydrocarbon 3-8 membered monocyclic or 7-14 membered bicyclic ring system having at least one non-aromatic ring. Cycloalkyl groups may be optionally substituted with one or more substituents. In one embodiment, 0, 1, 2, 3, or 4 atoms of each ring of a cycloalkyl group may be substituted by a substituent. Representative examples of cycloalkyl group include cyclopropyl, cyclopentyl, cyclohexyl, cyclobutyl, cycloheptyl, cyclooctyl, cyclononyl, and cyclodecyl.

The term "cycloalkenyl" refers to a hydrocarbon 3-8 membered monocyclic or 7-14 membered bicyclic ring system having at least one non-aromatic ring, wherein the non-aromatic ring has some degree of unsaturation. Cycloalkenyl groups may be optionally substituted with one or more substituents. In one embodiment, 0, 1, 2, 3, or 4 atoms of each ring of a cycloalkenyl group may be substituted by a substituent. Examples of cycloalkenyl groups include cyclohexenyl, bicyclo[2.2.1]hept-2-enyl, dihydronaphthalenyl, benzocyclopentyl, cyclopentenyl, cyclopentadienyl, cyclohexenyl, cyclohexadienyl, cycloheptenyl, cycloheptadienyl, cycloheptatrienyl, cyclooctenyl, cyclooctadienyl, cyclooctatrienyl, cyclooctatetraenyl, cyclononenyl, cyclononadienyl, cyclodecenyl, cyclodecadienyl and the like.

The term "aryl" refers to a hydrocarbon monocyclic, bicyclic or tricyclic aromatic ring system. Aryl groups may be optionally substituted with one or more substituents. In one embodiment, 0, 1, 2, 3, 4, 5 or 6 atoms of each ring of an aryl group may be substituted by a substituent. Examples of aryl groups include phenyl, naphthyl, anthracenyl, fluorenyl, indenyl, azulenyl, and the like.

As used herein, the term "arylalkyl" means an aryl group that is attached to another group by a $(C_1-C_6)$alkylene group. Arylalkyl groups may be optionally substituted, either on the aryl portion of the arylalkyl group or on the alkylene portion of the arylalkyl group, with one or more substituent. Representative arylalkyl groups include benzyl, 2-phenyl-ethyl, naphth-3-yl-methyl and the like.

As used herein, the term "alkylene" refers to an alkyl group that has two points of attachment. The term "$(C_1-C_6)$alkylene" refers to an alkylene group that has from one to six carbon atoms. Non-limiting examples of alkylene groups include methylene (—CH$_2$—), ethylene (—CH$_2$CH$_2$—), n-propylene (—CH$_2$CH$_2$CH$_2$—), isopropylene (—CH$_2$CH (CH$_3$)—), and the like.

The term "arylalkoxy" refers to an alkoxy substituted with aryl.

The term "heteroaryl" refers to an aromatic monocyclic, bicyclic, or tricyclic ring system having 1-4 ring heteroatoms if monocyclic, 1-6 heteroatoms if bicyclic, or 1-9 heteroatoms if tricyclic, said heteroatoms selected from O, N, or S, and the remainder ring atoms being carbon (with appropriate hydrogen atoms unless otherwise indicated). Heteroaryl groups may be optionally substituted with one or more substituents. In one embodiment, 0, 1, 2, 3, or 4 atoms of each ring of a heteroaryl group may be substituted by a substituent. Examples of heteroaryl groups include pyridyl, 1-oxo-pyridyl, furanyl, benzo[1,3]dioxolyl, benzo[1,4]dioxinyl, thienyl, pyrrolyl, oxazolyl, oxadiazolyl, imidazolyl thiazolyl, isoxazolyl, quinolinyl, pyrazolyl, isothiazolyl, pyridazinyl, pyrimidinyl, pyrazinyl, triazinyl, triazolyl, thiadiazolyl, isoquinolinyl, indazolyl, benzoxazolyl, benzofuryl, indolizinyl, imidazopyridyl, tetrazolyl, benzimidazolyl, benzothiazolyl, benzothiadiazolyl, benzoxadiazolyl, indolyl, tetrahydroindolyl, azaindolyl, imidazopyridyl, quinazolinyl, purinyl, pyrrolo[2,3]pyrimidinyl, pyrazolo[3,4]pyrimidinyl, and benzo (b)thienyl, 3H-thiazolo[2,3-c][1,2,4]thiadiazolyl, imidazo[1,2-d]-1,2,4-thiadiazolyl, imidazo[2,1-b]-1,3,4-thiadiazolyl, 1H,2H-furo[3,4-d]-1,2,3-thiadiazolyl, 1H-pyrazolo[5,1-c]-1,2,4-triazolyl, pyrrolo[3,4-d]-1,2,3-triazolyl, cyclopentatriazolyl, 3H-pyrrolo[3,4-c]isoxazolyl, 1H,3H-pyrrolo[1,2-c]oxazolyl, pyrrolo[2,1b]oxazolyl, and the like.

As used herein, the term "heteroaralkyl" or "heteroarylalkyl" means a heteroaryl group that is attached to another group by a $(C_1-C_6)$alkane or alkene. Heteroarylalkyl groups may be optionally substituted, either on the heteroaryl portion of the heteroaralkyl group or on the alkyl portion of the heteroarylalkyl group, with one or more substituents. Representative heteroaralkyl groups include 2-(pyridin-4-yl)-propyl, 2-(thien-3-yl)-ethyl, imidazol-4-yl-methyl and the like.

The term "heterocycloalkyl" refers to a nonaromatic 5-8 membered monocyclic, 8-12 membered bicyclic, or 11-14 membered tricyclic ring system comprising 1-3 heteroatoms if monocyclic, 1-6 heteroatoms if bicyclic, or 1-9 heteroatoms if tricyclic, said heteroatoms selected from O, N, S, B, P or Si. Heterocycloalkyl groups may be optionally substituted with one or more substituents. In one embodiment, 0, 1, 2, 3, or 4 atoms of each ring of a heterocycloalkyl group may be substituted by a substituent. Representative heterocycloalkyl groups include piperidinyl, piperazinyl, 2-oxopiperazinyl, 2-oxopiperidinyl, 2-oxopyrrolidinyl, 4-piperidonyl, tetrahydropyranyl, tetrahydrothiopyranyl, tetrahydrothiopyranyl sulfone, morpholinyl, thiomorpholinyl, thiomorpholinyl sulfoxide, thiomorpholinyl sulfone, 1,3-dioxolane, tetrahydropyranyl, tetrahydrothienyl, thiirene.

The term "heterocycloalkenyl" refers to a nonaromatic 5-8 membered monocyclic, 8-12 membered bicyclic, or 11-14 membered tricyclic ring system comprising 1-3 heteroatoms if monocyclic, 1-6 heteroatoms if bicyclic, or 1-9 heteroatoms if tricyclic, said heteroatoms selected from O, N, S, B, P or Si, wherein the nonaromatic ring system has some degree of unsaturation. Heterocyclyl groups may be optionally substituted with one or more substituents. In one embodiment, 0, 1, 2, 3, or 4 atoms of each ring of a heterocyclyl group may be substituted by a substituent. Examples of these groups include 2-pyrrolinyl, 3-pyrrolinyl, 4H-pyranyl, 2-pyrazolinyl, dihydrofuranyl, dihydrothiophenyl, 2-imidazolinyl, indolinyl and the like.

The term "alkylamino" refers to an amino substituent which is further substituted with one or two alkyl groups. The term "aminoalkyl" refers to an alkyl substituent which is further substituted with one or more amino groups. The term "mercaptoalkyl" refers to an alkyl substituent which is further substituted with one or more mercapto groups. The term "hydroxyalkyl" refers to an alkyl substituent which is further substituted with one or more hydroxyl groups. The term "sulfonylalkyl" refers to an alkyl substituent which is further substituted with one or more sulfonyl groups. The term "sulfonylaryl" refers to an aryl substituent which is further substituted with one or more sulfonyl groups. The term alkylcarbonyl refers to an —C(O)-alkyl. The term "mercaptoalkoxy" refers to an alkoxy substituent which is further substituted with one or more mercapto groups.

The term "alkylcarbonylalkyl" refers to an alkyl substituent which is further substituted with —C(O)-alkyl. The alkyl or aryl portion of alkylamino, aminoalkyl, mercaptoalkyl, hydroxyalkyl, mercaptoalkoxy, sulfonylalkyl, sulfonylaryl, alkylcarbonyl, and alkylcarbonylalkyl may be optionally substituted with one or more substituents.

As used herein the term "substituent" or "substituted" means that a hydrogen radical on a compound or group (such as, for example, alkyl, alkenyl, alkynyl, alkylene, aryl, aralkyl, heteroaryl, heteroaralkyl, cycloalkyl, cyclyl, heterocycloalkyl, or heterocyclyl group) is replaced with any desired group that does not substantially adversely affect the stability of the compound. In one embodiment, desired substituents are those which do not adversely affect the activity of a compound. The term "substituted" refers to one or more substituents (which may be the same or different), each replacing a hydrogen atom. Examples of substituents include, but are not limited to, halogen (F, Cl, Br, or I), hydroxyl, amino, alkylamino, arylamino, dialkylamino, diarylamino, cyano, nitro, mercapto, oxo (i.e., carbonyl), thio, imino, formyl, carbamido, carbamyl, carboxyl, thioureido, thiocyanato, sulfoamido, sulfonylalkyl, sulfonylaryl, alkyl, alkenyl, alkoxy, mercaptoalkoxy, aryl, heteroaryl, cyclyl, heterocyclyl, wherein alkyl, alkenyl, alkyloxy, aryl, heteroaryl, cyclyl, and heterocyclyl are optionally substituted with alkyl, aryl, heteroaryl, halogen, hydroxyl, amino, mercapto, cyano, nitro, oxo (═O), thioxo (═S), or imino (═NR), wherein R is as defined herein.

In other embodiments, substituents on any group (such as, for example, alkyl, alkenyl, alkynyl, aryl, arylalkyl, heteroaryl, heteroaralkyl, cycloalkyl, cycloalkenyl, heterocycloalkyl, and heterocycloalkenyl) can be at any atom of that group, wherein any group that can be substituted (such as, for example, alkyl, alkenyl, alkynyl, aryl, aralkyl, heteroaryl, heteroaralkyl, cycloalkyl, cyclyl, heterocycloalkyl, and heterocyclyl) can be optionally substituted with one or more substituents (which may be the same or different), each replacing a hydrogen atom. Examples of suitable substituents include, but not limited to alkyl, alkenyl, alkynyl, cyclyl, cycloalkyl, heterocycloalkenyl, heterocycloalkyl, arylalkyl, heteroarylalkyl, aryl, heteroaryl, halogen, haloalkyl, cyano, nitro, alkoxy, aryloxy, hydroxyl, hydroxylalkyl, oxo (i.e., carbonyl), carboxyl, formyl, alkylcarbonyl, alkylcarbonylalkyl, alkoxycarbonyl, alkylcarbonyloxy, aryloxycarbonyl, heteroaryloxy, heteroaryloxycarbonyl, thio, mercapto, mercaptoalkyl, arylsulfonyl, amino, aminoalkyl, dialkylamino, alkylcarbonylamino, alkylaminocarbonyl, or alkoxycarbonylamino; alkylamino, arylamino, diarylamino, alkylcarbonyl, or arylamino-substituted aryl; arylalkylamino, aralkylaminocarbonyl, amido, alkylaminosulfonyl, arylaminosulfonyl, dialkylaminosulfonyl, alkylsulfonylamino, arylsulfonylamino, imino, carbamido, carbamyl, thioureido, thiocyanato, sulfoamido, sulfonylalkyl, sulfonylaryl, or mercaptoalkoxy.

Additional suitable substituents on alkyl, alkenyl, alkynyl, aryl, aralkyl, heteroaryl, heteroaralkyl, cycloalkyl, cyclyl, heterocycloalkyl, and heterocyclyl include, without limitation halogen, CN, $NO_2$, $OR^{15}$, $SR^{15}$, $S(O)_2OR^{15}$, $NR^{15}R^{16}$, $C_1$-$C_2$ perfluoroalkyl, $C_1$-$C_2$ perfluoroalkoxy, 1,2-methylenedioxy, (═O), (═S), (═$NR^{15}$), $C(O)OR^{15}$, $C(O)NR^{15}R^{16}$, $OC(O)NR^{15}R^{16}$, $NR^{15}C(O)NR^{15}R^{16}$, $C(NR^{16})NR^{15}R^{16}$, $NR^{15}C(NR^{16})NR^{15}R^{16}$, $S(O)_2NR^{15}R^{16}$, $R^{17}$, $C(O)H$, $C(O)R^{17}$, $NR^{15}C(O)R^{17}$, $Si(R^{15})_3$, $OSi(R^{15})_3$, $Si(OH)_2R^{15}$, $P(O)(OR^{15})_2$, $S(O)R^{17}$, or $S(O)_2R^{17}$. Each $R^{15}$ is independently hydrogen, $C_1$-$C_6$ alkyl optionally substituted with cycloalkyl, aryl, heterocyclyl, or heteroaryl. Each $R^{16}$ is independently hydrogen, $C_3$-$C_6$ cycloalkyl, aryl, heterocyclyl, heteroaryl, $C_1$-$C_4$ alkyl or $C_1$-$C_4$ alkyl substituted with $C_3$-$C_6$ cycloalkyl, aryl, heterocyclyl or heteroaryl. Each $R^{17}$ is independently $C_3$-$C_6$ cycloalkyl, aryl, heterocyclyl, heteroaryl, $C_1$-$C_4$ alkyl or $C_1$-$C_4$ alkyl substituted with $C_3$-$C_6$ cycloalkyl, aryl, heterocyclyl or heteroaryl. Each $C_3$-$C_6$ cycloalkyl, aryl, heterocyclyl, heteroaryl and $C_1$-$C_4$ alkyl in each $R^{15}$, $R^{16}$ and $R^{17}$ can optionally be substituted with halogen, CN, $C_1$-$C_4$ alkyl, OH, $C_1$-$C_4$ alkoxy, COOH, $C(O)OC_1$-$C_4$ alkyl, $NH_2$, $C_1$-$C_4$ alkylamino, or $C_1$-$C_4$ dialkylamino.

As used herein, the term "lower" refers to a group having up to six atoms. For example, a "lower alkyl" refers to an alkyl radical having from 1 to 6 carbon atoms, and a "lower alkenyl" or "lower alkynyl" refers to an alkenyl or alkynyl radical having from 2 to 6 carbon atoms, respectively.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., formulation into therapeutic products, intermediates for use in production of therapeutic compounds, isolatable or storable intermediate compounds, treating diseases, disorders, or symptoms thereof, including those delineated herein). The compounds produced by the methods herein can be incorporated into compositions, including solutions, capsules, crèmes, or ointments for administration to a subject (e.g., human, animal). Such compositions (e.g., pharmaceuticals) are useful for providing to the subject desirable health or other physiological benefits that are associated with such compounds.

The compounds of the formulae herein are available from commercial sources or may be synthesized using reagents and techniques known in the art, including those delineated herein. The chemicals used in the synthetic routes may include, for example, solvents, reagents, catalysts, and protecting group and deprotecting group reagents. The methods described above may also additionally include steps, either before or after the steps described specifically herein, to add or remove suitable protecting groups in order to ultimately allow synthesis of the compounds herein. In addition, various synthetic steps may be performed in an alternate sequence or order to give the desired compounds. Synthetic chemistry transformations and protecting group methodologies (protection and deprotection) useful in synthesizing the applicable compounds are known in the art and include, for example, those described in R. Larock, *Comprehensive Organic Transformations*, VCH Publishers (1989); T. W. Greene and P. G. M. Wuts, *Protective Groups in Organic Synthesis*, $3^{rd}$ Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

The compounds herein may contain one or more asymmetric centers and thus occur as racemates and racemic mixtures, single enantiomers, individual diastereomers and diastereomeric mixtures. All such isomeric forms of these compounds are expressly included in the present invention. The compounds herein may also contain linkages (e.g., carbon-carbon bonds) wherein bond rotation is restricted about that particular linkage, e.g., restriction resulting from the presence of a ring or double bond. Accordingly, all cis/trans and E/Z isomers are expressly included in the present invention. The compounds herein may also be represented in multiple tautomeric forms, in such instances, the invention expressly includes all tautomeric forms of the compounds described herein, even though only a single tautomeric form may be represented. All such isomeric forms of such compounds herein are expressly included in the present invention. All crystal forms and polymorphs of the compounds described herein are expressly included in the present invention. The term "N-oxides" refers to one or more nitrogen atoms, when present in an aromatic ring nitrogen-containing compound, that are in N-oxide oxidation form, i.e., N→O.

The compounds of this invention include the compounds themselves, as well as their salts, solvate, hydrate, polymorph, or prodrugs, if applicable. As used herein, the term "pharmaceutically acceptable salt," is a salt formed from, for example, an acid and a basic group of a compound of any one of the formulae disclosed herein. Illustrative salts include, but are not limited, to sulfate, citrate, acetate, chloride, bromide, iodide, nitrate, bisulfate, phosphate, acid phosphate, lactate, salicylate, acid citrate, tartrate, oleate, tannate, pantothenate, bitartrate, ascorbate, succinate, maleate, besylate, fumarate, gluconate, glucuronate, saccharate, formate, benzoate, glutamate, methanesulfonate, ethanesulfonate, benzenesulfonate, and p-toluenesulfonate salts. The term "pharmaceutically acceptable salt" also refers to a salt prepared from a compound of any one of the formulae disclosed herein having an acidic functional group, such as a carboxylic acid functional group, and a pharmaceutically acceptable inorganic or organic base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methyl,N-ethylamine; diethylamine; triethylamine; mono-, bis-, or tris-(2-hydroxy-lower alkyl amines), such as mono-, bis-, or tris-(2-hydroxyethyl)amine, 2-hydroxy-tert-butylamine, or tris-(hydroxymethyl)methylamine, N,N,-di-lower alkyl-N-(hydroxy lower alkyl)-amines, such as N,N-dimethyl-N-(2-hydroxyethyl)amine, or tri-(2-hydroxyethyl)amine; N-methyl-D-glucamine; and amino acids such as arginine, lysine, and the like. The term "pharmaceutically acceptable salt" also refers to a salt prepared from a compound of any one of the formulae disclosed herein having a basic functional group, such as an amino functional group, and a pharmaceutically acceptable inorganic or organic acid. Suitable acids include hydrogen sulfate, citric acid, acetic acid, hydrochloric acid (HCl), hydrogen bromide (HBr), hydrogen iodide (HI), nitric acid, phosphoric acid, lactic acid, salicylic acid, tartaric acid, ascorbic acid, succinic acid, maleic acid, besylic acid, fumaric acid, gluconic acid, glucaronic acid, formic acid, oxalic acid, benzoic acid, glutamic acid, methanesulfonic acid, ethanesulfonic acid, benzenesulfonic acid, and p-toluenesulfonic acid.

As used herein, the term "hydrate" means a compound of the present invention or a salt thereof, which further includes a stoichiometric or non-stoichiometric amount of water bound by non-covalent intermolecular forces.

Methods of the Invention

As demonstrated in the accompanying figures (FIGS. 5, 6, 10 and 12), the invention demonstrates that it is possible to 'mix-and-match' combined SCFA-sugar biological activities from hybrid molecules by, amongst other factors, maintaining a SCFA at the C6 position of ManNAc. For example, these factors, such as enhanced growth inhibition and toxicity as well as altered patterns of gene expression that reduce the metastatic potential of malignant cells, offer improvements over the current generation of SCFA-sugar compounds under consideration as cancer drugs. A. Improvements include the following: The ability to enhance the toxicity of SCFA-hexosamine hybrid molecules improves the ability of the compounds of the invention to be used as cancer drugs; B. Anti-metastatic cancer drugs. An added dimension reported in this invention is the anti-invasive properties of SCFA-ManNAc hybrid molecules through suppression of MUC1 and MMP9 to acts as anti-metastatic cancer drugs; these activities depend on the presence of a SCFA group at the C6 position of a ManNAc scaffold; C. A set of analogs have been designed to present bioorthogonal chemical functional groups on the cell surface as part on non-natural sialic acids to acts as a chemical handle on cancer drugs; D. the analogs can be designed to have 'cancer vaccine' properties of stimulating the immune system against the cancer cells.

The combination of the biological activities SCFA- and sugar activities of compounds (such as $Bu_4$ManNAc or 1(OH)But$_3$ManNAc is useful for cancer treatment because each of the biological activities of the hybrid molecule have been designed to work in concert against a particular characteristic of cancer. An equally valuable aspect of the current invention, however, is ability to separate the various biological activities of the hybrid molecules—for example it is now possible to maintain flux through a glycosylation pathway and to simultaneously avoid or minimize SCFA effects such as toxicity or changes to gene expression that affect the cellular phenotype under investigation (see FIG. 10). This ability opens the door to the many scenarios where an SCFA is attached to a core sugar towards the sole purpose of increasing the metabolic efficiency of the sugar without triggering biological activities of the SCFA moiety. In this case, non-natural monosaccharide analogs would transit the glycosylation pathways without eliciting unrelated changes to proliferation, apoptosis, or gene expression that would either confound interpretation of the experiment under way or actually lead to deleterious cellular outcomes. Representative applications include: A. Metabolic labeling: When undertaking metabolic labeling experiments as a research instrument to uncover biological function, it is critical not to grossly perturb either related or unrelated cellular systems. For example, O-GlcNAc protein modification has been linked to cell stress and apoptosis, therefore if GlcNAc analogs used for detection of these proteins induce apoptosis themselves, it would be difficult to deconvolute the effects of the biological stimulus under investigation from the effects of the probe; B. Tissue engineering and control of stem cell fate: installation of thiol groups in sialic acids (via the thiolated ManNAc analogs) allowed novel modes of attachment of cells to complementary surfaces. This technique is of value for achieving cell adhesion to tissue engineering scaffolds. Moreover, human stem cells subject to this novel carbohydrate-based adhesion uniquely differentiated into neurons through activation of Wnt signaling (and possibly other signaling pathways as well). C. Regenerative medicine: At least two regenerative medicine applications already have been reported for non-natural monosaccharides used in MOE that would benefit from this invention. The first is the incorporation of 'glycolyl' sialic acid, which has potential applications for spinal cord regeneration through the use of $Ac_5ManNGc$. Similar to $Ac_5ManNTGc$, this compound has considerable toxicity that inhibits use; consequently the methods described in this invention that allow toxicity to be separated from the desired biological activity will make this approach viable. A second example of MOE used in regenerative medicine has been described where the glucosamine analog "GlcNBut" has shown to increase extracellular matrix production that could be of potential benefit to patients with arthritis. By using the methods described in this invention, the 'drug-like' character of this compound can be dramatically improved without toxicity or overt off-target effects; D. Treatment of inborn errors of metabolism: There are several examples of inborn errors of metabolism included congenital disorders of glycosylation (CDGs) and the degenerative muscle disorder hereditary inclusion body myopathy (HIBM) that are potentially treatable through dietary supplementation with the deficient sugar. In some cases the sugars needed to treat these disorders are considerably expensive, including fucose that is effective against certain forms of the CDG leukocyte adhesion deficiency (LAD) and ManNAc that is needed for HIBM therapy.

The above two sections described potential products and applications of the compounds described in this invention where all of the activities of an analog were devoted to a common cause (i.e., treatment of cancer) or where one of the activities was maintained (the sugar-based effects) while the other effects were minimized or negated. For example, there are a third set of application that also depend on a minimization of toxicity but would also benefit from other SCFA effects either in combination or separately from the sugar-based activities of the compound. Tissue engineering and control of stem cell fate: As described in the preceding section, the relevance of MOE to tissue engineering (by creating engineered binding interfaces) and control of stem cell fate (by inducing the differentiation of stem cells to neurons) was established. At present it remains unclear whether this response is entirely glycosylation-related (as discussed above) or also involves an SCFA component. The latter possibility arises from reports of the effects of butyrate on stem cell differentiation. If confirmed, the methods described in this invention to further dissect the biological activities of MOE analogs will be valuable in gaining additional control over the developmental fates of stem cells.

Recombinant glycoprotein production: The production of recombinant glycoproteins has previously (in separate endeavors) utilized both components of a SCFA-sugar hybrid molecule—specifically, butyrate (to block cell growth to maximize the biosynthesis of the recombinant glycoproteins) and ManNAc (to improve the uniformity and product quality of the oligosaccharide portion of a glycoprotein). The ability of the current invention, by avoiding toxicity by use of compounds such as $6(OH)But_3ManNAc$, allows both functionalities to be delivered efficiently to cells in such a manner that is appropriate for recombinant glycoprotein production (a \$4 billion annual market projected to increase to \$20 billion over the next decade).

Diseases treated by butyrate: In addition to cancer, butyrate has shown favorable properties in cell-based studies to confront a diverse set of diseases including amelioration of antibiotic-associated diarrhea, treatment of ulcerative colitis, correction of the ion transport defect in cystic fibrosis, increased SMN (survival motor neuron protein) gene expression in spinal muscular atrophy patients, neuroprotective effects in Huntington's and Parkinson diseases, and control of the lytic cycle of Kaposi's sarcoma-associated herpevirus. At present, it is not clear if an 'SCFA-alone' response is desired for these conditions (which could be achieved with the current analogs) or whether a combined SCFA-sugar response would be preferred (which could also be achieved with the current invention). The latter possibility arises due to the implication of glycosylation abnormalities in several of these conditions that could, in theory, be ameliorated by an MOE approach.

Owing to the relative infancy of MOE technology, the intellectual property rights for mannosamine or monosaccharide-based biosynthetic precursors have been relatively few and narrowly defined. Although several patents have been issued in the past decade each one of them is (i) unique in their defined chemical structures and derivatives, and (iii) are related to non-overlapping specific applications in biomedicine or disease.

To illustrate briefly, Reutter et al have patented the applications of ManNProp (N-propanoyl mannosamine) in the free sugar form for use as medical treatment for demyelinating diseases [DE 197 38 484 A 1 (1999)]. This was followed by a patent for peracylated ManN-alkyl for stimulation of neurite outgrowth, mainly utilizing the peracetylated ManProp ($Ac_4ManNProp$) derivative [US 2005/0107333 A1, (2005)].

Figure 2:
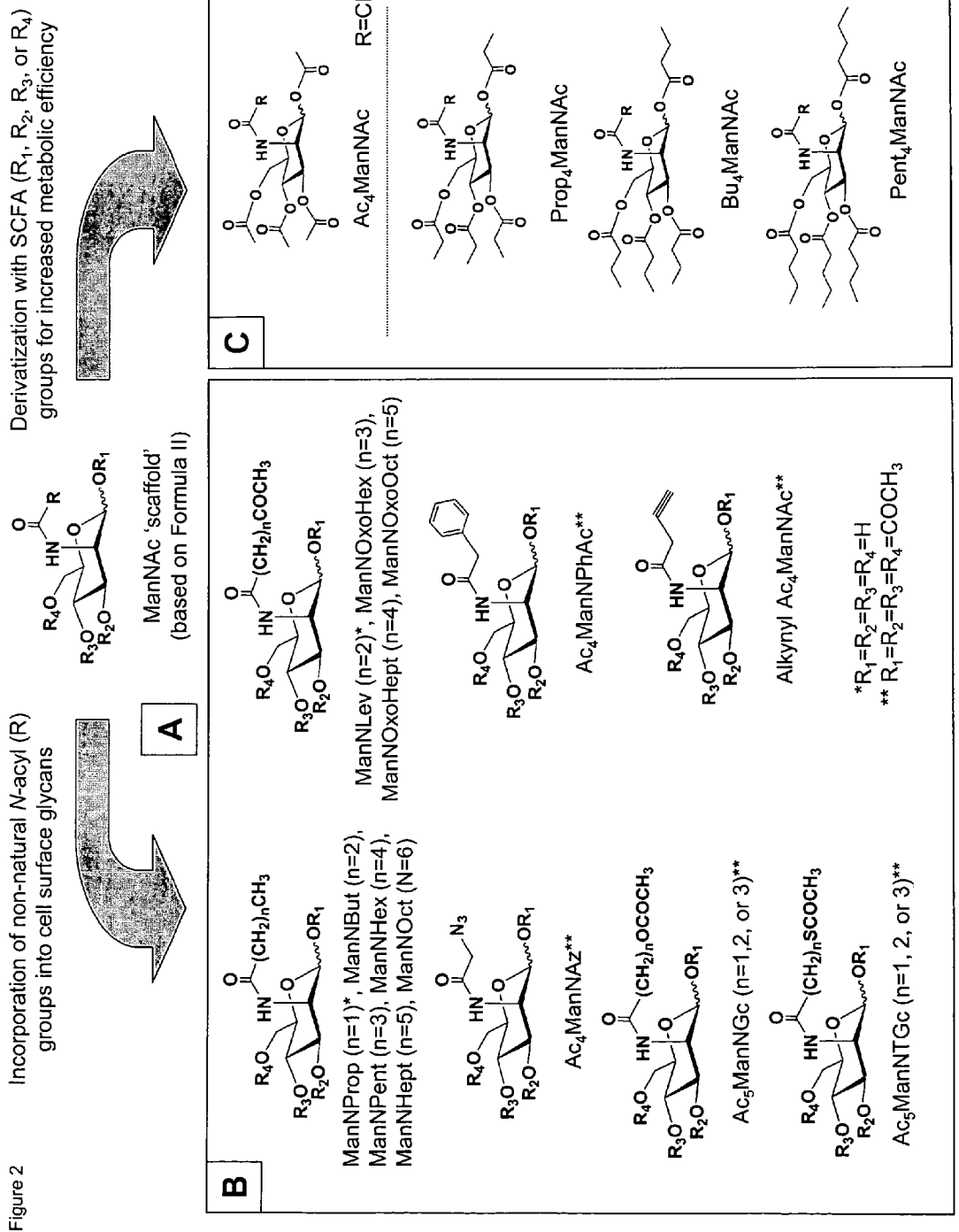
FIG. 2. ManNAc-based Analogs used in MOE. (A) The general chemical structure of N-acetyl-α/β-D-mannosamine (ManNAc) analogs is shown along with the 'R' and '$R_1$-$R_4$' positions where non-natural modifications have been reported previously. (B) A representative compilation of modifications at the N-acyl (the 'R' position) is shown; these modifications are maintained throughout the biosynthetic process and appear as part of the final glycan structure and are displayed on the cell surface. In the past, the '$R_1$-$R_4$' groups have been uniformly either "H" or acetate (Ac). (C) '$R_1$-$R_4$' groups at the O-hydroxyl positions have also been demonstrated for the additional range of short chain fatty acids (SCFA) shown.
Figure 3:
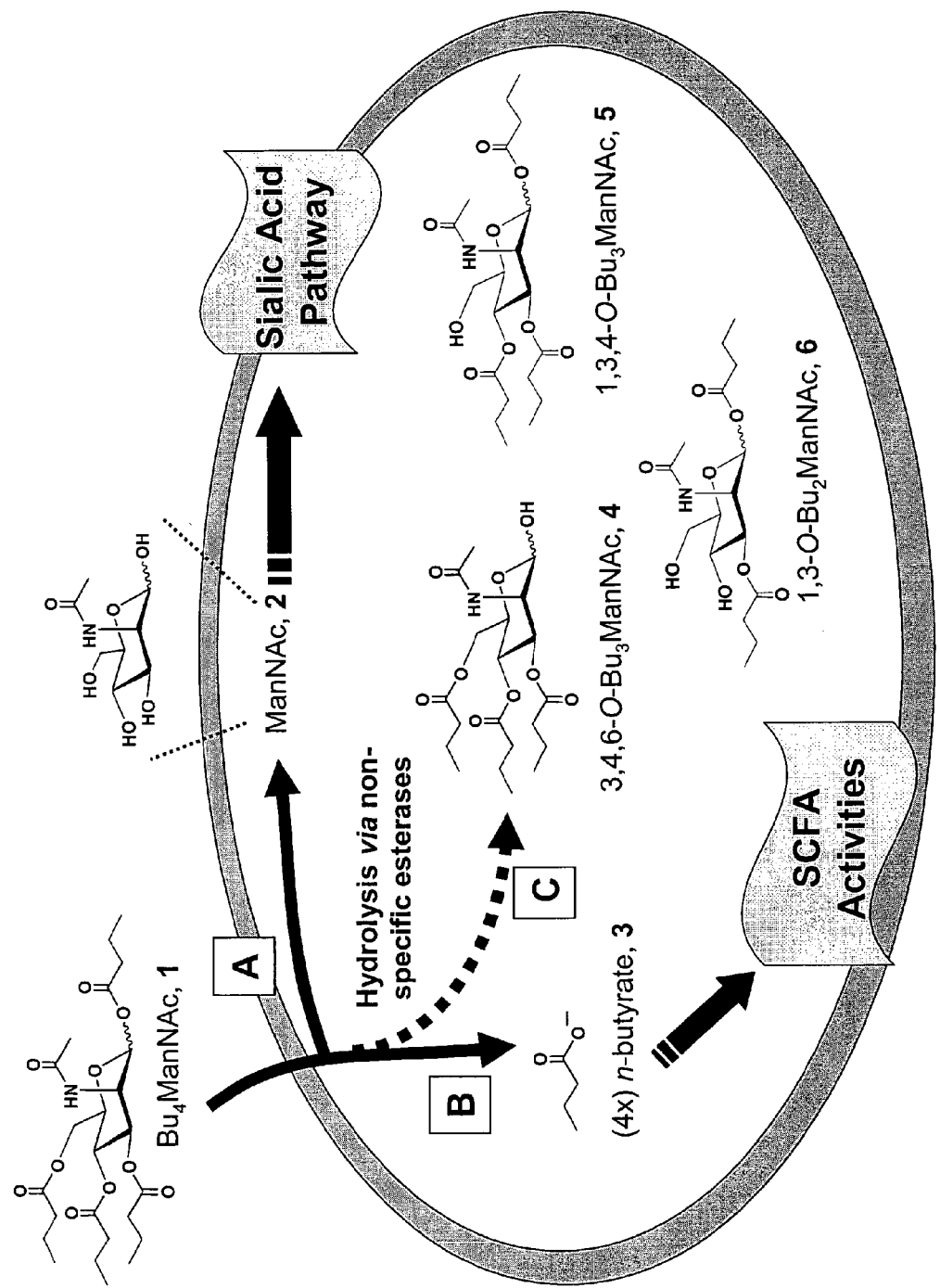
FIG. 3. Metabolic Processing of SCFA-ManNAc Hybrid Molecules Generates Compounds with New Biological Activity. (A) SCFA-carbohydrate prodrugs, exemplified by Bu$_4$ManNAc 1, readily cross the plasma membrane. Nonspecific esterases within a cell hydrolyze 1 into ManNAc 2, thereby increasing flux into the sialic acid biosynthetic pathway. At the same time n-butyrate 3 is released (B), supporting SCFA activities such as growth inhibition and induction of cell cycle checkpoint proteins such as p21. (C) In addition to 2 and 3, which have well-characterized biological activities, 'active' compounds responsible for the biological responses to 1 may result from partial hydrolysis where one (e.g., cpd 4 or 5), two (e.g., cpd 6), or three butyrate moieties are absent from the monosaccharide core (note that 14 such compounds exist for each of the α and (3 conformers, as shown in FIG. 4). Data from pilot studies establishing the unique biological activities of the partially-acylated compounds is shown in FIGS. 5 and 6.
Figure 4:
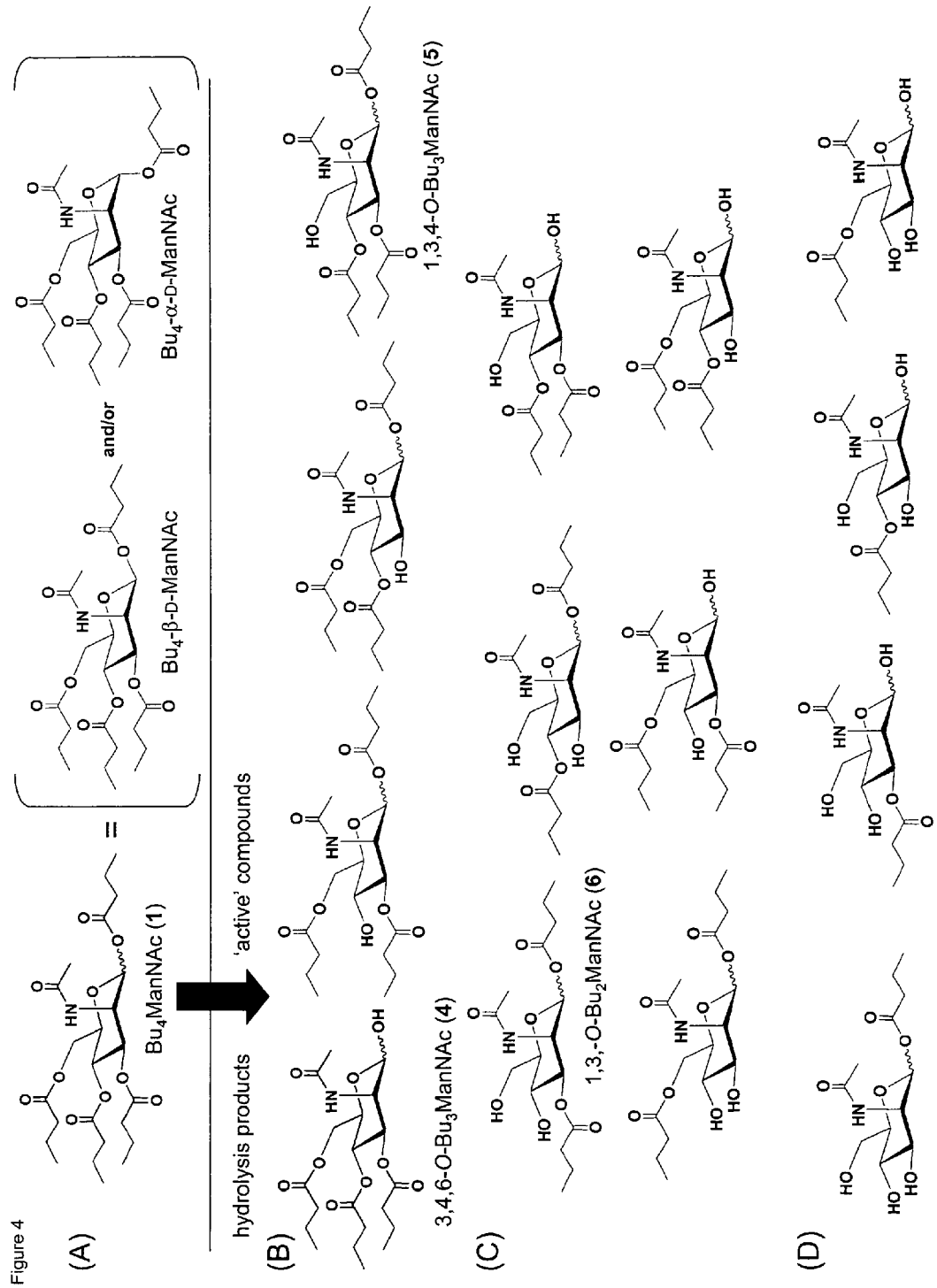
FIG. 4. Illustration of Partially-acylated Compounds derived From $Bu_4ManNAc$. The 14 α- and β-derivatives of $Bu_4ManNAc$ are shown to illustrate the compounds derived from hydrolysis of the parent compound. A similar set of compounds derives from propionate and valerate (FIG. 2C) as well as for the various 'R' modified forms of ManNAc (FIG. 2B). Similar sets of compounds can be based on other 'core' sugars (see Formula I-VII) and addition '$R_1$-$R_4$' groups that include an expanded range of SCFA.
Figure 5:
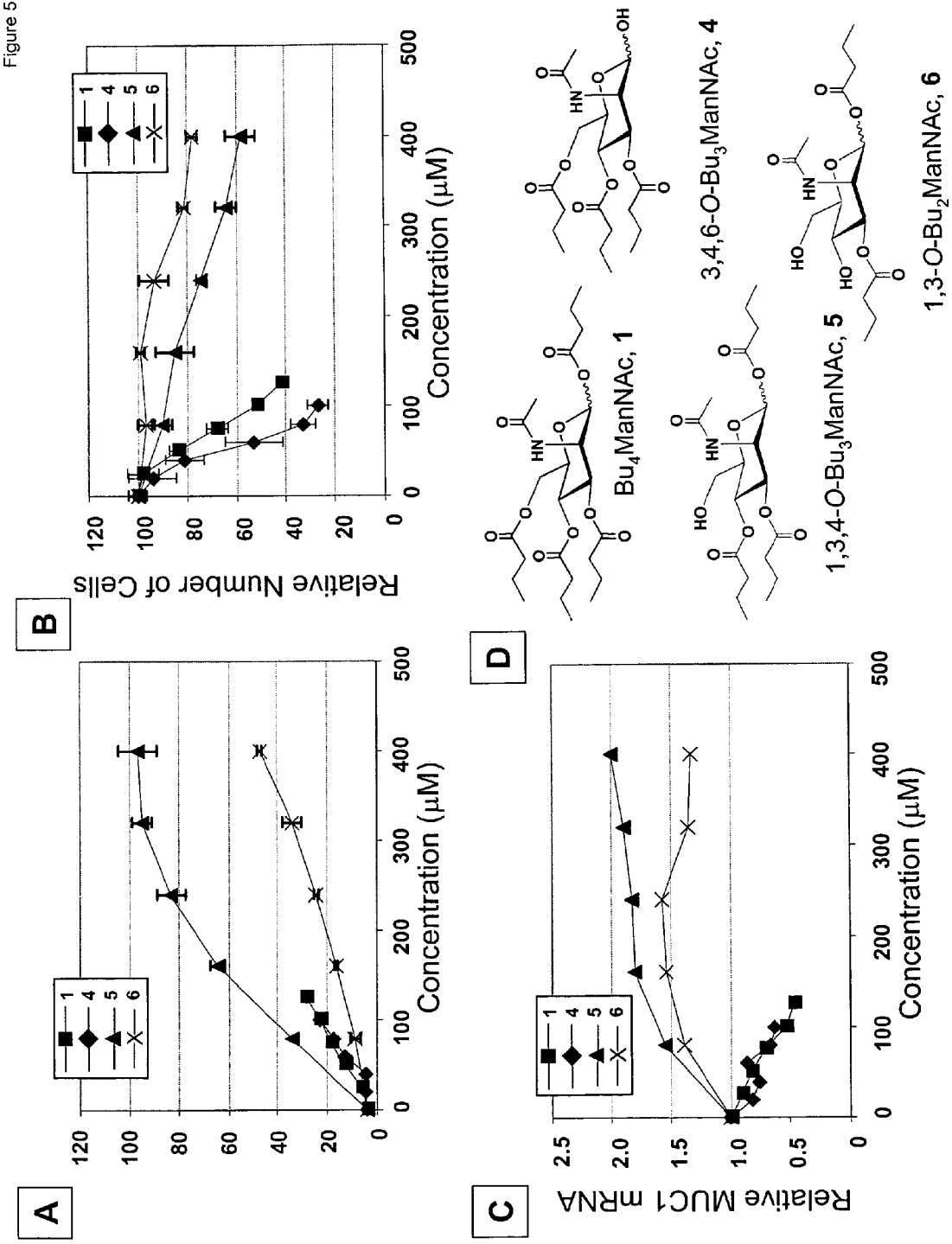
FIG. 5. Response of MDA-MB-231 cells to 3,4,6-O-$Bu_3ManNAc$ (4), 1,3,4-O-$Bu_3ManNAc$ (5) and 1,3-O-$But_2ManNAc$ (6) demonstrates the unique biological responses to analogs derivatized with a mixed population of hydroxyl and SCFA substituents. (A) Sialic acid production, (B) growth inhibition, and (C) MUC1 mRNA in cells exposed to 1, 4, 5, and 6 were monitored by the periodate resorcinol assay, cell counts, and qRT-PCR, respectively. (D) The chemical structures of to 1, 4, 5, and 6 are shown.
Figure 6:
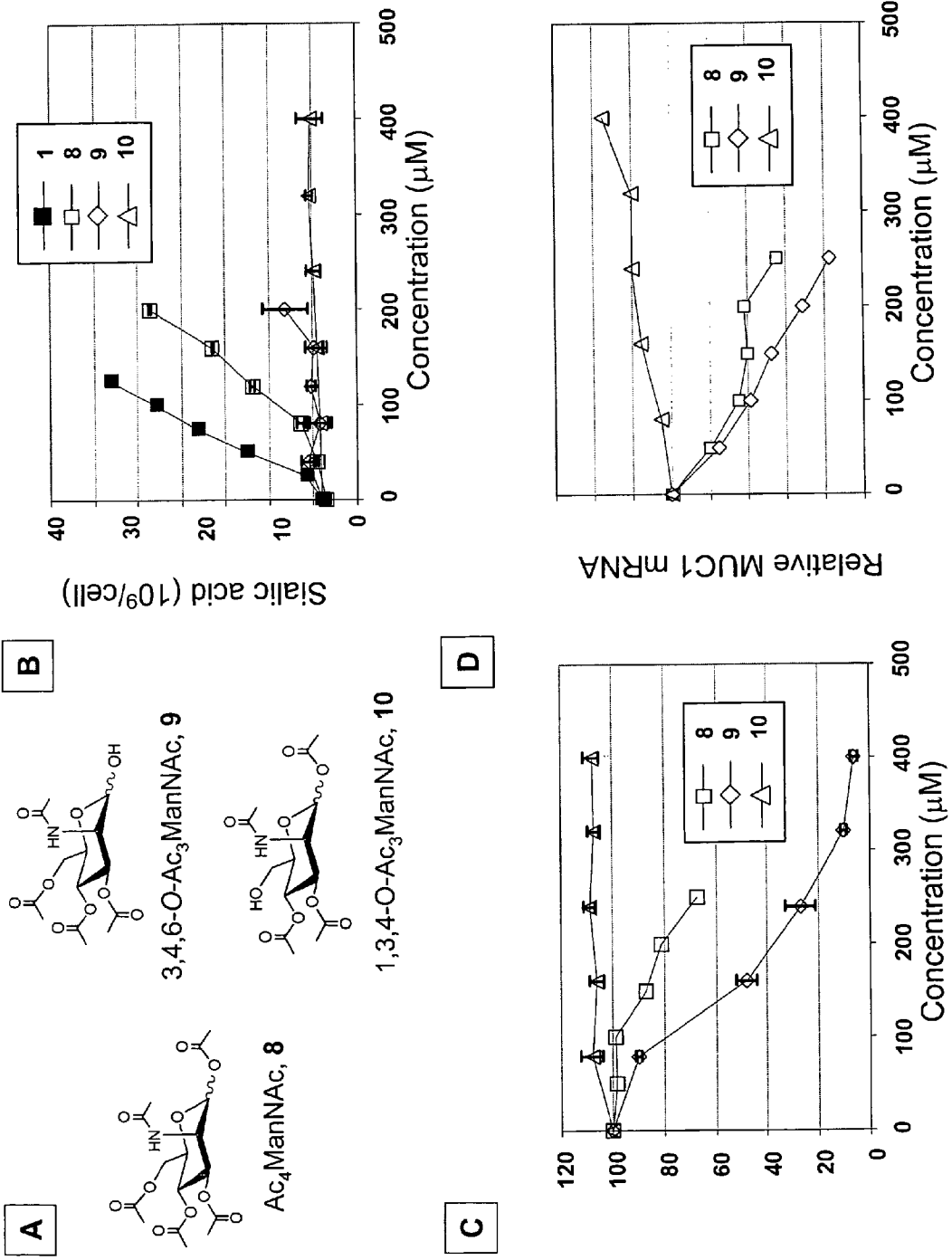
FIG. 6. Response of MDA-MB-231 cells to $Ac_4ManNAc$ (8), 3,4,6-O—$Ac_3ManNAc$ (9), and 1,3,4-O—$Ac_3ManNAc$ (10) demonstrates the unique biological responses to analogs derivatize with a mixed population of hydroxyl and SCFA substituents does not just apply to n-butyrate derivatizes but is a general phenomenon for SCFA. (A) The structures of these compounds are shown along with sialic acid production (B), growth inhibition (C), and MUC1 mRNA levels (D) that were monitored by the periodate resorcinol assay, cell counts, and qRT-PCR, respectively.
Figure 7:
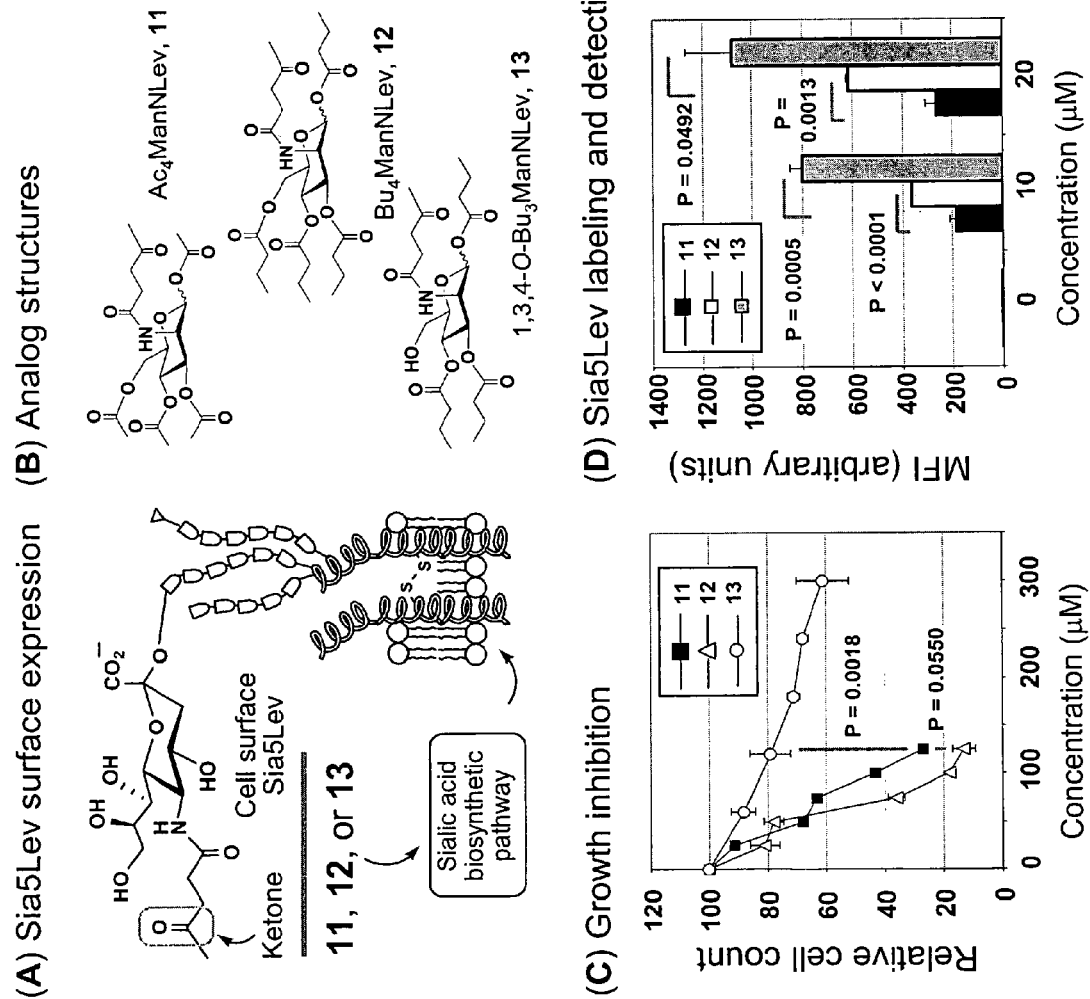
FIG. 7. Partial Acylation Structure-activity Relationships (SAR) Apply to 'Core' Sugars other than ManNAc as demonstrated by surface expression of Sia5Lev in Jurkat cells. (A) Sia5Lev is displayed in surface glycans upon biosynthetic incorporation of 11, 12, or 13 (structures are shown in Panel B). (C) Growth inhibition after 3 days showed that the peracetyl-11 and perbutanoyl-12 ManNLev analogs have equivalent effects, whereas the tributanolylated analog 13 is significantly less inhibitory. (D) Surface detection of ketone-bearing sialosides by conjugation with biotin hydrazide, staining with FITC-avidin, and quantification by flow cytometry showed that perbutanolylated ManNLev (12) was more effective than the peracetylated analog 11, and in turn, the tributanolylated analog 13 was even more efficient at providing cell surface ketone labeling.
Figure 8:
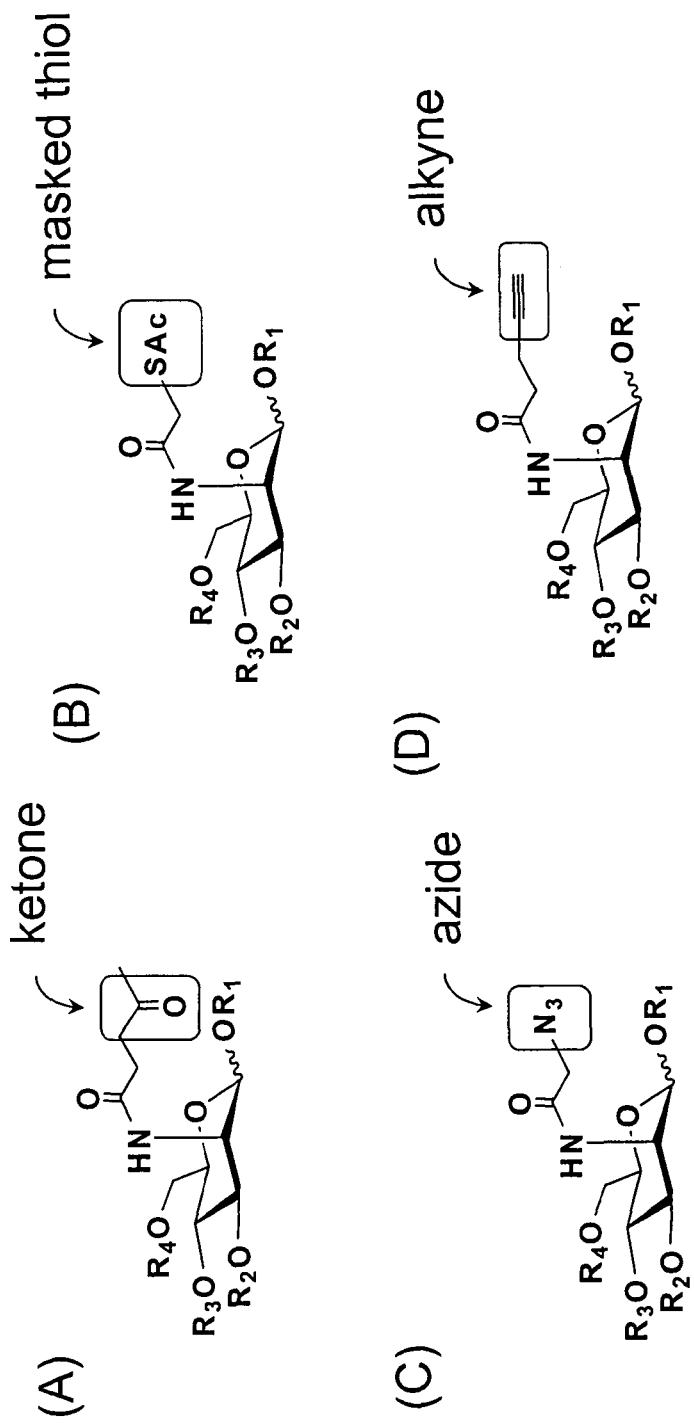
FIG. 8. Illustration of chemical functional groups not usually found in carbohydrates that can be used metabolic labeling applications by exploiting chemoselective ligation reactions. These groups include (A) the ketone of "Lev" analogs (such as those depicted in Drawing 7) that under selective reaction with hydrazide or aminooxy functionalities, (B) thiol groups that under reaction with maleimide and gold (as well as other) functionalities, (C) azide groups that under reaction with modified phosphines or alkynes in the "click reaction" and (D) alkynes that react with azide functional groups. In all cases, the biological activity of the analogs can be modulated by the SAR of the '$R_1$-$R_4$' groups shown in Drawings 5, 6, 7, and 10; specific examples of '$R_1$-$R_4$' groups combined with ketone and azide "R" functionalities are provided in Drawings 10 and 11.
Figure 11:
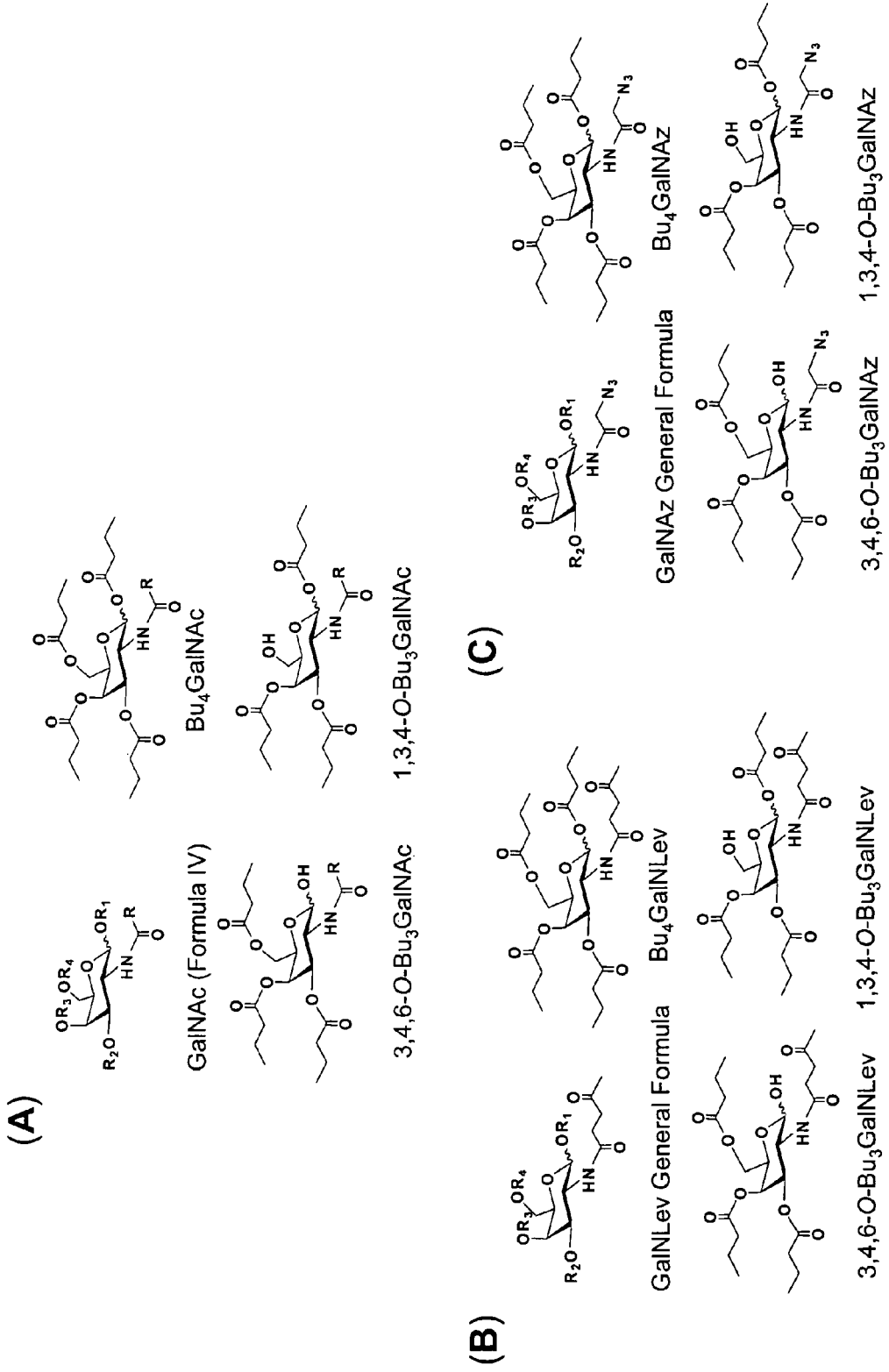
FIG. 11. GalNAc analgogs for mucin protein glycosylation. Based on the GlcNAc precedent set in Drawing 10, similar sets of analogs can be specified for GalNAc that include (A) the natural "NAc" R group or (B) the ketone containing "Lev" R group or the (C) corresponding azide-substituted analogs. Additional structural variations are specified in the text (See Formula IV and related discussion).
Figure 12:
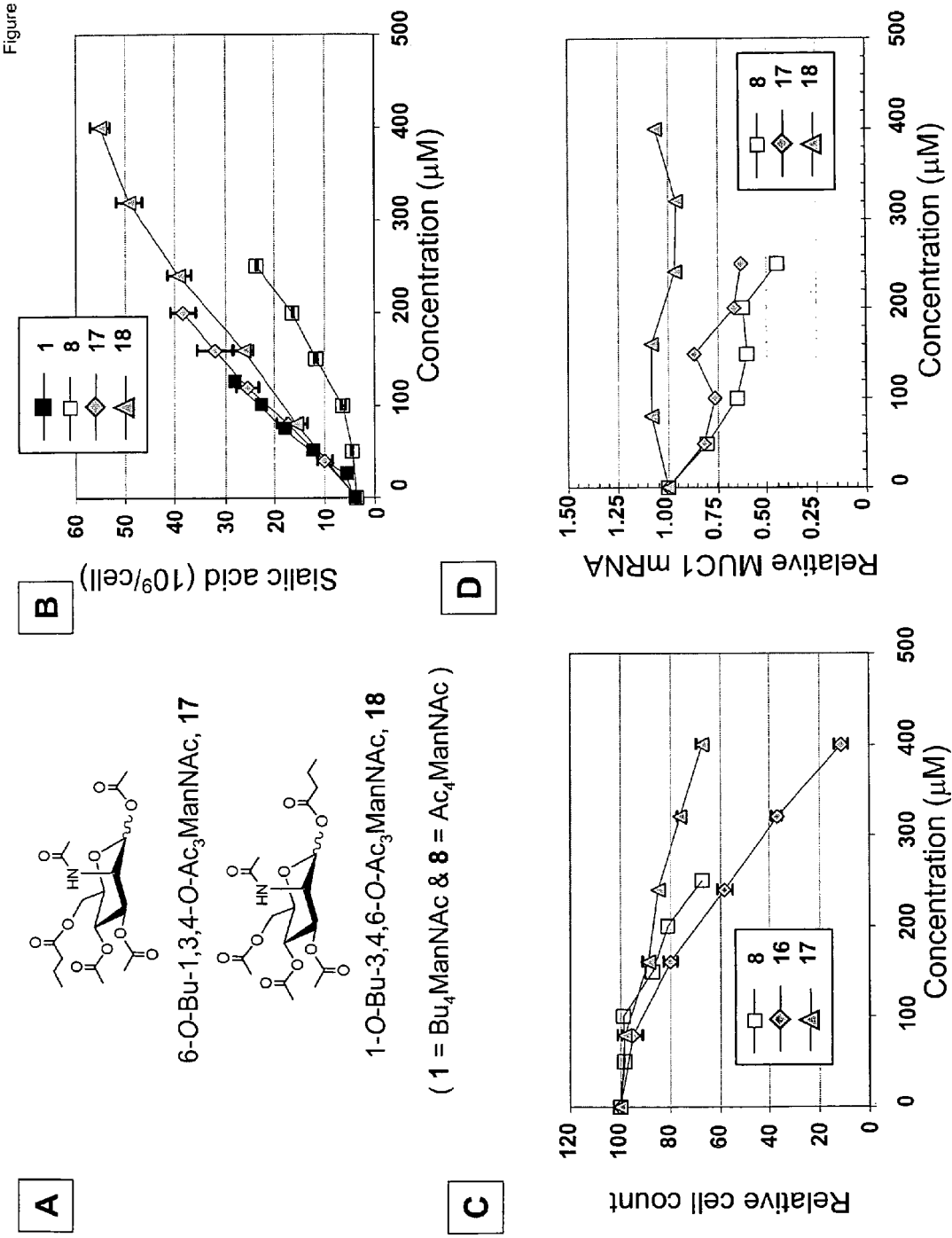
FIG. 12. Biological responses can be tuned by 'mix-and-matching' the SCFA groups attached to a ManNAc (2). (A) Butyrate groups were substituted for acetate at either the C1 (16) or C6 (17) positions of $Ac_4ManNAc$ (8) and these three compounds were compared with 1 for sialic acid production in the periodate resorcinol assay (B). Growth inhibition (C) and MUC1 mRNA levels (D) were also measured for 8, 16, and 17 showing that biological responses differed based on the relative position of the longer chain n-butyrate group.
Figure 14:
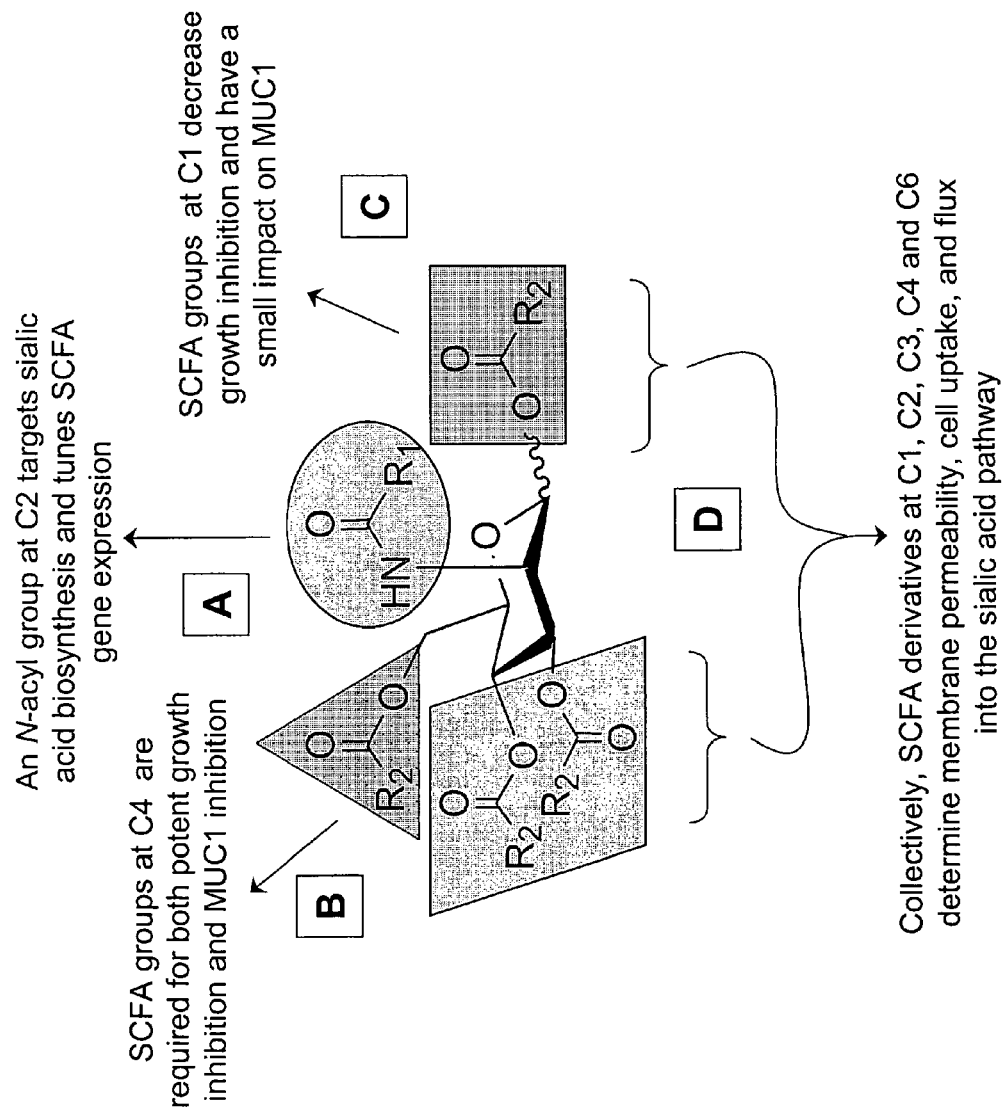
FIG. 14. SCFA-ManNAc hybrid molecules constitute a versatile development platform for modulating biological activity. Structure activity relationships for the (A) N-acyl (C2) position, (B) C6 position, (C) anomeric (C1) position, and (D) the collective effects of SCFA esters are summarized.

Metabolic oligosaccharide engineering (MOE) is an established technology where non-natural sugars intercept glycosylation pathways in the place of their natural counterparts and are incorporated in to cellular glycans (FIG. 1). Several dozen sugar analogs used in MOE have been reported (FIG. 2). Moreover, MOE has many potential applications in research, medicine, and biotechnology (as described in the referenced cited in this paragraph). Despite the attractive features of MOE, development of MOE-based technologies have been hindered by two significant issues. First, mono- and disaccharide analogs used in MOE are not 'drug-like' leading to efforts to improve their cellular uptake and pharmacologic properties by appending the short chain fatty acid (SCFA) acetate via ester linkages to the hydroxyl groups of the sugar. This strategy has in turn led to the problem that the SCFA groups elicit biological responses of their own that can confound the intended effects on glycosylation (for example, by changing the expression of the enzymes involved in glycosylation) and have wide ranging effects on a cells (for example, growth inhibition and toxicity that hinders many potential applications of MOE).

Pharmaceutical Compositions and Kits

As used herein, the terms "treat," "treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

As used herein, the terms "prevent," "preventing," "prevention," "prophylactic treatment" and the like refer to reducing the probability of developing a disorder or condition in a subject, who does not have, but is at risk of or susceptible to developing a disorder or condition.

The preferred therapeutic methods of the invention (which include prophylactic treatment) in general comprise administration of a therapeutically effective amount of the compounds herein, such as a compound of the formulae herein to a subject (e.g., animal, human) in need thereof, including a mammal, particularly a human. Such treatment will be suitably administered to subjects, particularly humans, suffering from, having, susceptible to, or at risk for a cancer or proliferative disease, disorder, or symptom thereof. Determination of those subjects "at risk" can be made by any objective or subjective determination by a diagnostic test or opinion of a subject or health care provider (e.g., genetic test, enzyme or protein marker, Marker (as defined herein), family history, and the like). The compounds herein may be also used in the treatment of any other disorders in which cell proliferation and migration may be implicated.

For therapeutic applications, the compounds of the formulae herein may be suitably administered to a subject such as a mammal, particularly a human, alone or as part of a pharmaceutical composition, comprising the formulae herein together with one or more acceptable carriers thereof and optionally other therapeutic ingredients. The carrier(s) must be "acceptable" in the sense of being compatible with the other ingredients of the formulation and not deleterious to the recipient thereof.

The pharmaceutical compositions of the invention include those suitable for oral, rectal, nasal, topical (including buccal and sublingual), vaginal or parenteral (including subcutaneous, intramuscular, intravenous and intradermal) administration. In certain embodiments, the compound of the formulae herein is administered transdermally (e.g., using a transdermal patch or iontophoretic techniques). Other formulations may conveniently be presented in unit dosage form, e.g., tablets and sustained release capsules, and in liposomes, and may be prepared by any methods well known in the art of pharmacy. See, for example, Remington's Pharmaceutical Sciences, Mack Publishing Company, Philadelphia, Pa. (17th ed. 1985).

Such preparative methods include the step of bringing into association with the molecule to be administered ingredients such as the carrier which constitutes one or more accessory ingredients. In general, the compositions are prepared by uniformly and intimately bringing into association the active ingredients with liquid carriers, liposomes or finely divided solid carriers or both, and then if necessary shaping the product.

In certain preferred embodiments, the compound is administered orally. Compositions of the present invention suitable for oral administration may be presented as discrete units such as capsules, sachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion, or packed in liposomes and as a bolus, etc.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface-active or dispersing agent. Molded tablets may be made by molding in a suitable machine a mixture of the powdered compound moistened with an inert liquid diluent. The tablets optionally may be coated or scored and may be formulated so as to provide slow or controlled release of the active ingredient therein. Methods of formulating such slow or controlled release compositions of pharmaceutically active ingredients, such as those herein and other compounds known in the art, are known in the art and described in several issued US patents, some of which include, but are not limited to, U.S. Pat. Nos. 4,369,172; and 4,842,866, and references cited therein. Coatings can be used for delivery of compounds to the intestine (see, e.g., U.S. Pat. Nos. 6,638,534, 5,217,720, and 6,569,457, and references cited therein).

A skilled artisan will recognize that in addition to tablets, other dosage forms can be formulated to provide slow or controlled release of the active ingredient. Such dosage forms include, but are not limited to, capsules, granulations and gel-caps.

Compositions suitable for topical administration include lozenges comprising the ingredients in a flavored basis, usually sucrose and acacia or tragacanth; and pastilles comprising the active ingredient in an inert basis such as gelatin and glycerin, or sucrose and acacia.

Compositions suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets.

Application of the subject therapeutics may be local, so as to be administered at the site of interest. Various techniques can be used for providing the subject compositions at the site of interest, such as injection, use of catheters, trocars, projectiles, pluronic gel, stents, sustained drug release polymers or other device which provides for internal access. Where an organ or tissue is accessible because of removal from the patient, such organ or tissue may be bathed in a medium containing the subject compositions, the subject compositions may be painted onto the organ, or may be applied in any convenient way.

Other applications of compounds of the formulae herein are for treatment of stem cells in vitro to induced directed and controlled differentiation and subsequent applications in regenerative medicine and cell transplantation therapy etc. The compound and compositions herein are administered (e.g., introduced to, contacted) with stem cells in a therapeutically effective amount in order to induce the desired effect. See, e.g., Sampathkumar et al., *Nature Chemical Biology*, vol. 2, No. 3, pp. 149-152 (March 2006). In particular, the compounds are useful for cellular response processes including for example, in modulating neuronal differentiation, inducing β-catenin expression, and modulating glycosylation pathways.

As used herein, the terms "HDAC inhibitor compound derivative" and "HDAC inhibitor prodrug" are those based on compounds (including those of the formulae delineated herein) and include pharmaceutically acceptable derivatives or prodrugs thereof, respectively. A "pharmaceutically acceptable derivative or prodrug" means any pharmaceutically acceptable salt, ester, salt of an ester, or other derivative of a compound of this invention which, upon administration to a recipient, is capable of providing (directly or indirectly) an active compound of this invention. Particularly favored derivatives and prodrugs are those that increase the bioavailability of the compounds of this invention when such compounds are administered to a mammal (e.g., by allowing an orally administered compound to be more readily absorbed into the blood) or which enhance delivery of the parent compound to a biological compartment (e.g., the brain or central nervous system) relative to the parent species. Preferred prodrugs include derivatives where a group which enhances aqueous solubility or active transport through the gut membrane is appended to the structure of formulae described herein. See, e.g., Alexander, J. et al. *Journal of Medicinal Chemistry* 1988, 31, 318-322; Bundgaard, H. *Design of Prodrugs*; Elsevier: Amsterdam, 1985; pp 1-92; Bundgaard, H.; Nielsen, N. M. *Journal of Medicinal Chemistry* 1987, 30, 451-454; Bundgaard, H. *A Textbook of Drug Design and Development*; Harwood Academic Publ.: Switzerland, 1991; pp 113-191; Digenis, G. A. et al. *Handbook of Experimental Pharmacology* 1975, 28, 86-112; Friis, G. J.; Bundgaard, H. *A Textbook of Drug Design and Development*; 2 ed.; Overseas Publ.: Amsterdam, 1996; pp 351-385; Pitman, I. H. *Medicinal Research Reviews* 1981, 1, 189-214; Testa, B. and Mayer, J. M. *Hydrolysis in Drug and Prodrug Metabolism, Chemistry, Biochemistry and Enzymology*, VHCA, Zürich and Wiley-VCH GmbH & Co. KGaA, Weihnheim, 2003.

The compounds of this invention may be modified by appending appropriate functionalities to enhance selective biological properties. Such modifications are known in the art and include those which increase biological penetration into a given biological compartment (e.g., central nervous system), increase oral availability, increase solubility to allow administration by injection, alter metabolism and alter rate of excretion. It will be appreciated that actual preferred amounts of a given compound herein used in a given therapy will vary according to the particular active compound being utilized, the particular compositions formulated, the mode of application, the particular site of administration, the patient's weight, general health, sex, etc., the particular indication being treated, etc. and other such factors that are recognized by those skilled in the art including the attendant physician or veterinarian. Optimal administration rates for a given protocol of administration can be readily determined by those skilled in the art using conventional dosage determination tests, or by any method known in the art or disclosed herein.

Therefore, in certain embodiments, compounds of the invention, such as those of the formulae herein, are administered at dosage levels of about 0.0001 to 4.0 grams once per day (or multiple doses per day in divided doses) for adults. Thus, in certain embodiments of this invention, a compound herein is administered at a dosage of any dosage range in which the low end of the range is any amount between 0.1 mg/day and 400 mg/day and the upper end of the range is any amount between 1 mg/day and 4000 mg/day (e.g., 5 mg/day and 100 mg/day, 150 mg/day and 500 mg/day). In other embodiments, a compound herein, is administered at a dosage of any dosage range in which the low end of the range is any amount between 0.01 mg/kg/day and 90 mg/kg/day and the upper end of the range is any amount between 1 mg/kg/day and 100 mg/kg/day (e.g., 0.5 mg/kg/day and 2 mg/kg/day, 5 mg/kg/day and 20 mg/kg/day, 50-150 mg/kg/day). The dosing interval can be adjusted according to the needs of individual patients. For longer intervals of administration, extended release or depot formulations can be used.

The methods herein include administering to the subject (including a subject identified as in need of such treatment) an effective amount of a compound described herein, or a composition described herein to produce such effect. Identifying a subject in need of such treatment can be in the judgment of a subject or a health care professional and can be subjective (e.g. opinion) or objective (e.g. measurable by a test or diagnostic method).

Another aspect is a composition including a compound of any of the formulae herein and a pharmaceutically acceptable carrier. The composition can also include an additional therapeutic agent (e.g., anticancer agents). Additional anticancer agents include, for example, an antiangiogenesis agent, selective estrogen-receptor modulator (SERM), breast cancer therapeutic agent, aromatase inhibitor, biologic response modifiers, hormonal therapies agent, anthracycline, taxane, alkylating agent, taxol, cis-platin, arabinofuranosyl cytosine (ara-C), 5-fluorouracil (5-FU), altretamine, busulfan, chlorambucil, cyclophosphamide, ifosfamide, mechlorethamine, melphalan, thiotepa, cladribine, fluorouracil, floxuridine, gemcitabine, thioguanine, pentostatin, methotrexate, 6-mercaptopurine, cytarabine, carmustine, lomustine, streptozotocin, carboplatin, oxaliplatin, iproplatin, tetraplatin, lobaplatin, JM216, JM335, fludarabine, aminoglutethimide, flutamide, goserelin, leuprolide, megestrol acetate, cyproterone acetate, tamoxifen, anastrozole, bicalutamide, dexamethasone, diethylstilbestrol, prednisone, bleomycin, dactinomycin, daunorubicin, doxirubicin, idarubicin, mitoxantrone, losoxantrone, mitomycin-c, plicamycin, paclitaxel, docetaxel, CPI-11, epothilones, topotecan, irinotecan, 9-amino camptothecan, 9-nitro camptothecan, GS-211, etoposide, teniposide, vinblastine, vincristine, vinorelbine, procarbazine, asparaginase, pegaspargase, methoxtrexate, octreotide, estramustine, hydroxyurea, tamoxifen, raloxifene, toremifene, exemestane, letrozole, anastrozole, megestrol, trastuzumab, goserelin acetate, fulvestrant, doxorubicin, epirubicin, or cyclophosphonamide and the like.

Another aspect is a method of making a pharmaceutical composition delineated herein, including the step of combining a compound herein (e.g., a compound of any of the formulae herein) with a pharmaceutically acceptable carrier. The method can further include combining an additional therapeutic agent with the compound and/or carrier.

The invention also provides kits for treatment or prevention of a disease or disorder (or symptoms) thereof, including cancer, or proliferative disorder or symptom thereof. In one embodiment, the kit includes an effective amount of a compound herein in unit dosage form, together with instructions for administering the compound to a subject suffering from or susceptible to a disease or disorder or symptoms thereof. In other embodiments, the kit comprises a sterile container which contains the compound; such containers can be boxes, ampules, bottles, vials, tubes, bags, pouches, blister-packs, or other suitable container form known in the art. Such containers can be made of plastic, glass, laminated paper, metal foil, or other materials suitable for holding medicaments. The instructions will generally include information about the use of the compound of the formulae herein for treatment of a disease or disorder or symptoms thereof, including those of a cardiovascular nature. In other embodiments, the instructions include at least one of the following: description of the compound; dosage schedule and administration for treatment of a disease or disorder or symptoms thereof, including those of a cardiovascular nature; precautions; warnings; indications; counter-indications; overdosage information; adverse reactions; animal pharmacology; clinical studies; and/or references. The instructions may be printed directly on the container (when present), or as a label applied to the container, or as a separate sheet, pamphlet, card, or folder supplied in or with the container.

In another aspect, an embodiment provides kits for treatment of a disease(s) or disorder(s) or symptoms thereof, including those of a proliferative disorder nature. In one embodiment, the kit includes an effective amount of a compound of the formulae herein in unit dosage form, together with instructions for administering the compound of the formulae hereinto a subject suffering from or susceptible to a disease or disorder or symptoms thereof, including those of a proliferative disorder nature and metastatic cancer. In preferred embodiments, the compound of the formulae herein is any of the specific compounds delineated herein.

This is the first report evaluating the effects of the compounds herein on several stages of cancer development and treatment. The prevention and treatment methods are contemplated to reduce apoptosis of normal (e.g., non-cancerous cells or tissue) or to sensitize cancerous cells or tissue to be more vulnerable to the compounds themselves or when co-administered with additional anticancer agents.

Combinations of substituents and variables envisioned by this invention are only those that result in the formation of stable compounds. The term "stable", as used herein, refers to compounds which possess stability sufficient to allow manufacture and which maintain the integrity of the compound for a sufficient period of time to be useful for the purposes detailed herein (e.g., formulation into therapeutic products, intermediates for use in production of therapeutic compounds, isolatable or storable intermediate compounds, treating a disease or condition that has been linked to proliferation, cell cycle inhibition (e.g., HDAC inhibition) and/or abnormal glycosylation modulation (e.g., sialic acid biosynthesis).

The invention will be further described in the following examples. It should be understood that these examples are for illustrative purposes only and are not to be construed as limiting this invention in any manner.

EXAMPLES

General Remarks

All commercially purchased reagents were used without further purification. Thin layer chromatography (TLC) was performed on silica gel coated glass plates (Cat. No. 47521, Analtech, NJ). Column chromatography was performed using silica gel 60 Å. $^1$H and $^{13}$C NMR were obtained using a 400 MHz Bruker instrument at 22° C.; the chemical shifts values are reported in 'δ' and coupling constants (J) in Hz.

Mass spectrometry was performed using either ESI-MS, High resolution FAB-MS or MALDI-TOF (Voyager DE-STR, Applied Biosystems, Foster City, Calif.). Elemental analysis was performed by Atlantic Microlabs Inc., Atlanta, Ga. The starting material 2 was purchased from Pfanstiehl (Waukegan, Ill.); Molecular sieves 4 Å (Sigma-Aldrich, St. Louis, Mo.) was activated at 150° C. overnight, cooled in a desiccator and powdered freshly before use. Synthetic schemes (Scheme 1-6) are included in the respective experimental portions provides a list of substituents for the compounds reported herein.

Example 1

2-Acetamido-2-deoxy-1,3,4,6-tetra-O-pentanoyl-α, β-D-mannopyranose

To a stirred suspension of 2 (1.05 g, 4.4 mmol) and valeric anhydride (5 mL, 25.4 mmol) in pyridine (2.5 mL, 30.9 mmol) at 22° C. was added DMAP (cat.). After ~16 h, the mixture was concentrated and co-concentrated with toluene (25 mL). The residue was dissolved in dichloromethane (100 mL) and washed successively with ice-cold 5% aqueous hydrochloric acid (100 mL), water (100 mL) and aqueous saturated sodium bicarbonate (100 mL). The organic layer was filtered and concentrated. Column chromatography of the residue (hexanes:AcOEt) gave pure β (82%, semi-solid) followed by pure α (11%, semi-solid).

2-Acetamido-2-deoxy-1,3,4,6-tetra-O-pentanoyl-β-D-mannopyranose (20)

$^1$H-NMR (400 MHz, CDCl$_3$): δ 5.86 (d, 1H, J=1.8), 5.74 (d, 1H, J=9.1), 5.12 (t, 1H, J=9.7), 5.06 (dd, 1H, J=10.0, J=4.0), 4.75 (ddd, 1H, J=9.2, J=5.4, J=1.8), 4.26 (dd, 1H, J=12.5, J=5.5), 4.09 (dd, 1H, J=12.4, J=2.7), 3.78 (ddd, 1H, J=9.4, J=5.5, J=2.4), 2.36-2.16 (m, 8H), 2.07 (s, 3H), 1.64-1.49 (m, 8H), 1.37-1.25 (m, 8H), 0.96-0.84 (m, 12H); $^{13}$C-NMR (100 MHz): δ 173.2, 172.7, 172.4, 171.1, 170.3, 90.6 ($^1J_{C1-H1}$=166), 73.5, 71.1, 65.1, 61.7, 49.6, 33.7 (2C), 33.6, 33.5, 26.8, 26.7, 26.5, 26.4, 23.3, 22.2, 22.1 (2C), 22.0, 13.7, 13.6 (3C); FAB-MS m/z 580.3 [(M+Na)$^+$]; anal. calcd. For C$_{28}$H$_{47}$NO$_{10}$: C, 60.30; H, 8.49. Found: C, 60.40; H, 8.64.

2-Acetamido-2-deoxy-1,3,4,6-tetra-O-pentanoyl-α-D-mannopyranose $^1$H-NMR (400 MHz, CDCl$_3$): δ 6.03 (d, 1H, J=2.2), 5.67 (d, 1H, J=9.1), 5.33 (dd, 1H, J=10.4, J=4.6), 5.17 (t, 1H, J=10.1), 4.62 (ddd, 1H, J=9.3, J=4.6, J=1.7), 4.22 (dd, 1H, J=12.4, J=5.2), 4.05 (dd, 1H, J=12.2, J=2.3), 4.01 (dd, 1H, J=10.2, J=5.2, J=2.3), 2.42-2.16 (m, 8H), 2.05 (s, 3H), 1.67-1.49 (m, 8H), 1.41-1.23 (m, 8H), 0.96-0.83 (m, 12H); $^{13}$C-NMR (100 MHz) δ 173.2, 172.7, 172.5, 170.9, 169.9, 91.5

($^1J_{C1-H1}$=177), 70.3, 68.6, 65.1, 61.8, 49.4, 33.7 (2C), 33.6 (2C), 26.9, 26.8, 26.7, 26.6, 23.3, 22.2, 22.1 (3C), 13.7 (2C), 13.6 (2C).

Example 2

General Procedure for the Synthesis of 2-acetamido-3,4,6-tri-O-acyl-2-deoxy-α,β-D-manno/glucopyraose Scheme 1. Scheme for the synthesis of the 2-acetamido-3,4,6-tri-O-butanoyl-2-deoxy-α,β-D-mannopyranose (4), 2-acetamido-3,4,6-tri-O-acetyl-2-deoxy-α,β-D-mannopyranose (9) and 2-acetamido-3,4,5-tri-O-butanoyl-2-deoxy-α,β-D-glucopyranose (15) Conditions: (a) (RCO)$_2$O, pyridine, DMAP, 22 °C., 24 h; (b) Molecular sieves 4 A, MeOH, 22 °C., 7-12 h.

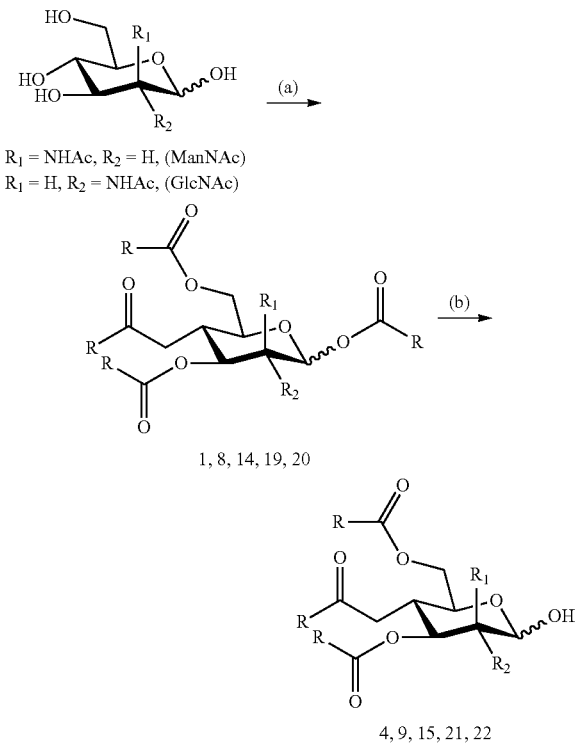

A mixture of 2-acetamido-1,3,4,6-tetra-O-acyl-2-deoxy-α,β-D-mannopyranose (1, 8, 14, 19 or 20, 2.0 mmol) and activated and powdered molecular sieves 4 Å (4.0 g) in methanol (100 mL) was stirred at 22° C. The reaction mixture was monitored by TLC (hexanes:ethyl acetate (AcOEt) 1:1) for maximum conversion to the hemi-acetal at the same time minimizing over de-acylation. After ~2-8 h, the reaction mixture was filtered through a pad of celite, washed twice with methanol (10 mL) and the combined filtrate was concentrated. Column chromatography of the residue (hexanes:ethyl acetate (AcOEt)) gave unreacted stating material (1, 8, 19 or 20), followed by the hemiacetal (4, 9, 15, 21 or 22).

2-Acetamido-3,4,6-tri-O-acetyl-2-deoxy-D-mannopyranose (9)

Crystalline solid, Yield: 90% (mixture of anomers; major: minor=88:12). $^1$H-NMR (400 MHz, CDCl$_3$): δ 6.15 (d, 0.12H, J=8.4 Hz, NH), δ 5.98 (d, 0.88H, J=8.8 Hz, NH), 5.42 (dd, 1H, J=4.4 & 10.4 Hz, H-3), 5.35 (s, 0.12H), 5.20-5.03 (m, 2.12H, H-1), 4.70 (bs, 0.88H), 4.65 (m, 0.12H, H-2), 4.60 (m, 0.88H, H-2), 4.35-4.05 (m, 2.88H), 3.75 (m, 0.12H, H-5), 2.12, 2.11, 2.07, 2.07 (4s, 6H), 2.06 (s, 2.64H, NHAc), 2.06 (s, 0.36H, NHAc), 2.03 (s, 0.36H, COCH$_3$), 2.00 (s, 2.64H, COCH$_3$); $^{13}$C-NMR (100 MHz, CDCl$_3$): δ 172.5, 170.9, 170.8, 170.7, 170.7, 170.2, 170.2, 170.2 (NHCO), 170.1 (NHCO), 93.9 (C-1), 93.5 (C-1), 72.5, 71.6, 69.0, 67.9, 66.2, 65.8, 62.7 (C-6), 62.6 (C-6), 52.0 (C-2), 51.1 (C-2), 23.4, 23.3, 21.1, 20.8, 20.8, 20.7, 20.7; FAB-MS: Calcd for C$_{14}$H$_{22}$NO$_9$ ([M+H]$^+$): 348.1295. found: 348.1294.

2-Acetamido-3,4,6-tri-O-propanoyl-2-deoxy-D-mannopyranose (21)

Crystalline solid, Yield: 76% (mixture of anomers, major: minor=80:20): $^1$H-NMR (400 MHz, CDCl$_3$): δ 5.85 (d, 0.20H, J=8.4 Hz, NH), 5.72 (d, 0.80H, J=8.4 Hz, NH), 5.43 (dd, 0.80H, J=4.4 and 10.0 Hz), 5.22-5.02 (m, 2.00H), 5.00 (s, 0.20H), 4.78 (m, 0.20H), 4.70-4.55 (m, 1H), 4.32-4.05 (m, 2.80H), 3.72 (m, 0.20H, H-5), 3.55 (m, 0.80H), 2.50-2.15 (m, 6H), 2.12 (s, 0.60H, NHAc), 2.07 (s, 2.40H, NHAc), 1.20-0.90 (m, 9H); $^{13}$C-NMR (100 MHz, CDCl$_3$): δ 173.9, 173.9, 173.2, 173.2, 173.1, 172.1, 170.3 (NHCO), 170.3 (NHCO), 93.6 (C-1), 93.2 (C-1), 72.4, 71.2, 68.6, 67.8, 65.7, 65.4, 62.2 (C-6), 60.2 (C-6), 51.9 (C-2), 51.0 (C-2), 27.2, 27.2, 27.1, 27.0, 27.1, 27.0, 23.0, 20.1, 8.8, 8.8, 8.7, 8.6, 8.5, 8.5.

2-Acetamido-3,4,6-tri-O-butanoyl-2-deoxy-D-mannopyranose (4)

Crystalline solid, Yield: 80% (mixture of anomers, major: minor=88:12): $^1$H-NMR (400 MHz, CDCl$_3$): δ 6.04 (d, 0.12H, J=8.4 Hz, NH), 5.88 (d, 0.88H, J=8.8 Hz, NH), 5.42 (dd, 0.88H, J=4.4 and 10.0 Hz), 5.22-5.02 (m, 2.12H), 5.00 (s, 0.12H), 4.65 (m, 0.12H, H-2), 4.58 (m, 0.88H, H-2), 4.43 (m, 0.88H), 4.32-4.05 (m, 2.88H), 3.70 (m, 0.12H, H-5), 2.45-2.13 (m, 6H), 2.10 (s, 0.36H, NHAc), 2.05 (s, 2.64H, NHAc), 1.90-1.50 (m, 6H), 1.10-0.80 (m, 9H); $^{13}$C-NMR (100 MHz, CDCl$_3$): δ 173.6, 173.2, 173.0, 173.0, 172.9, 172.8, 171.2 (NHCO), 171.2 (NHCO), 94.1 (C-1), 93.8 (C-1), 73.0, 72.0, 69.3, 68.4, 66.8, 66.0, 62.8 (C-6), 62.8 (C-6), 52.4 (C-2), 51.8 (C-2), 36.4, 36.4, 36.3, 23.6, 18.7, 18.7, 18.5, 14.0, 14.0, 14.0; FAB-MS: Calcd for C$_{20}$H$_{34}$NO$_9$ ([M+H]$^+$): 432.2234. found: 432.2234.

2-Acetamido-3,4,6-tri-O-pentanoyl-2-deoxy-D-mannopyranose (22)

Crystalline solid, Yield: 76% (mixture of anomers, major: minor=80:20): $^1$H-NMR (400 MHz, CDCl$_3$): δ 5.87 (d, 0.16H, J=8.6 Hz, NH), 5.75 (d, 0.84H, J=8.6 Hz, NH), 5.42 (dd, 0.84H, J=4.4 and 10.0 Hz), 5.22-5.02 (m, 2.00H), 5.00 (s, 0.16H), 4.90 (m, 0.20H), 4.70-4.55 (m, 1H), 4.32-4.05 (m, 2.84H), 3.84 (m, 0.84H), 3.72 (m, 0.16H, H-5), 2.50-2.15 (m, 6H), 2.11 (s, 0.48H, NHAc), 2.07 (s, 2.52H, NHAc), 1.70-1.1.40 (m, 6H), 1.40-1.20 (m, 6H), 1.10-0.78 (m, 9H); $^{13}$C-NMR (100 MHz, CDCl$_3$): δ 173.5, 173.5, 172.8, 172.8, 172.7, 172.6, 172.3 (NHCO), 170.5 (NHCO), 93.9 (C-1), 93.4 (C-1), 72.6, 71.3, 68.8, 68.0, 65.9, 65.5, 62.4 (C-6), 60.5 (C-6), 52.2 (C-2), 51.3 (C-2), 33.7, 33.7, 33.7, 33.7, 33.7, 33.7, 26.8, 26.8, 26.8, 26.8, 26.6, 26.6, 23.3, 23.3, 23.3, 23.3, 22.6, 22.6, 22.2, 22.2, 14.3, 14.3, 14.3, 13.6, 13.6, 13.6.

2-Acetamido-3,4,6-tri-O-butanoyl-2-deoxy-α,β-D-glucopyranose (15)

Crystalline solid, Yield: 80% (major:minor=95:5): $^1$H-NMR (400 MHz, CDCl$_3$): δ 6.35 (d, 0.05H, NH), 5.95 (d, 0.95H, J=9.2 Hz, NH), 5.40-4.95 (m, 3H), 4.60 (m, 0.05H, H-2), 4.30 (m, 0.95H, H-2), 4.27-3.95 (m, 3.95H), 3.70 (m, 0.05H, H-5), 2.43-2.13 (m, 6H), 2.05 (s, 0.15H, NHAc), 1.96 (s, 2.85H, NHAc), 1.74-1.52 (m, 6H), 1.10-0.86 (m, 9H); $^{13}$C-NMR (100 MHz, CDCl$_3$): δ 175.0, 174.5, 174.2, 173.7, 173.6, 172.0, 170.5 (NHCO), 170.4 (NHCO), 95.0 (C-1), 91.7 (C-1), 72.2, 72.0, 70.6, 68.0, 67.8, 67.8, 66.0, 61.9 (C-6), 58.0, 52.5 (C-2 major), 36.2, 36.2, 36.0, 36.0, 36.0, 36.0, 23.2, 23.0, 18.5, 18.5, 18.4, 18.4, 18.4, 18.3, 13.7, 13.7, 13.6, 13.6, 13.6, 13.6; MALDI-MS: Calcd for C$_{20}$H$_{33}$NO$_9$Na ([M+Na]$^+$): 454.2053. found: 454.3054.

Example 3

General Procedure of the Synthesis of 2-Acetamido-1,3,4-tri-O-acyl-2-deoxy-6-O-triphenylmethyl-α,β-D-manno/glucopyranose

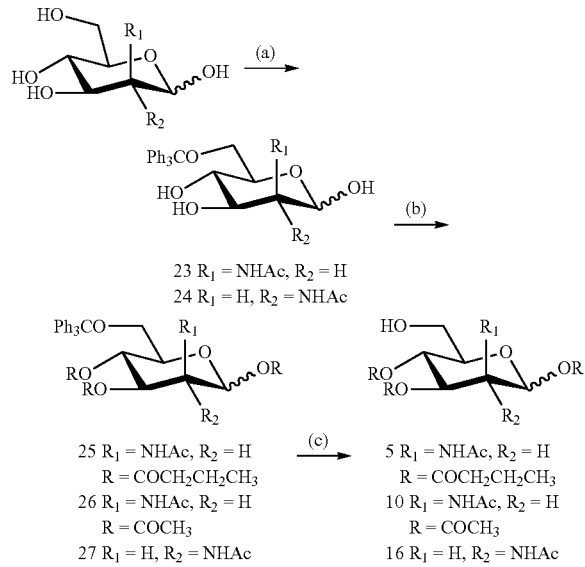

2-Acetamido-2-deoxy-6-O-triphenylmethyl-α,β-D-manno/glucopyranose (23 or 24)

To a stirred mixture of 2 or 7 (2 g, 0.835 mmol) in pyridine (2.7 mL) was added triphenylmethyl chloride (3 g, 1.07 mmol) at 22° C. After 48 h, the reaction mixture was heated at 60° C. for 2 h and monitored by TLC (AcOEt). The reaction mixture was concentrated and co-concentrated with toluene (3×20 mL). The residue was dissolved in AcOEt and washed with water. The organic layers was collected, dried over anh. Na$_2$SO$_4$, filtered and concentrated to obtain 23 or 24 as a crude product which was taken to the next step without further purification.

To a stirred solution of 23 or 24 (1 g, 2.16 mmol) in pyridine (1.46 mL, 18 mmol) at 0° C. (ice-water bath), the respective acid anhydride (either acetic anhydride or butyric anhydride) (12 mmol) was added. The reaction mixture was allowed to warm up to 22° C. and monitored by TLC (hexanes:AcOEt 3:1). After 24 h, the mixture was concentrated under reduced pressure, co-concentrated with toluene (3×10 mL) and extracted using a mixture of dichloromethane (100 mL) and water (50 mL). The organic layers were collected, dried over anh. Na$_2$SO$_4$, filtered and concentrated. Column chromatography of the residue (hexanes:AcOEt) gave products 25-27 as a mixture of anomers.

2-Acetamido-1,3,4-tri-O-acetyl-2-deoxy-6-O-triphenylmethyl-α,β-D-mannopyranose (25)

Syrup, Yield: 70% (2 steps) (mixture of anomers; major:minor=55:45) from ManNAc.: $^1$H-NMR (400 MHz, CDCl$_3$): δ 7.50-7.15 (m, 15H, 3×Ph), 6.13 (d, 0.55H, J=2.0 Hz, H-1), 5.88 (d, 0.45H, J=2.0 Hz, H-1), 5.86 (d, 0.45H, J=9.6 Hz, NH), 5.78 (d, 0.55H, J=9.2 Hz, NH), 5.36 (t, 0.55H, J=10.0), 5.32 (t, 0.45H, J=10.0 Hz), 5.31 (dd, 0.55H, J=4.4 and 10.0 Hz), 5.00 (dd, 0.45H, J=3.6 & 10.0 Hz), 4.78 (m, 0.45H, H-2), 4.65 (m, 0.55H, H-2), 3.93 (m, 0.55H, H-5), 3.68 (m, 0.45H, H-5), 3.36 (dd, 0.55H, J=2.4 & 10.8 Hz), 3.32 (dd, 0.45H, J=2.4 & 10.0 Hz), 3.12 (dd, 0.55H, J=4.0 & 10.0 Hz), 3.08 (dd, 1H, J=4.8 & 10.0 Hz), 2.18, 2.17, 2.14, 2.12, 2.11, 2.06, 2.03 (s, 1.35H, NHAc), 2.02 (s, 1.65H, NHAc); $^{13}$C-NMR (100 MHz, CDCl$_3$): δ 171.1, 170.3, 170.2, 169.9, 169.9, 168.7, 168.2 (NHCO), 168.0 (NHCO), 143.4, 143.0, 128.9, 128.7, 128.2, 127.9, 127.3, 127.2, 126.6, 91.8 (C-1), 90.2 (C-1), 86.8, 86.3, 73.4, 71.7, 71.5, 69.3, 69.3, 65.8, 61.5 (C-6), 61.3 (C-6), 49.4 (C-2), 49.3 (C-2), 23.4, 23.1, 20.9, 20.8, 20.5, 20.4, 20.4, 20.2. MALDI-MS: Calcd for C$_{33}$H$_{35}$NO$_9$Na ([M+Na]$^+$): 612.2209. found: 612.3708.

2-Acetamido-1,3,4-tri-O-butanoyl-2-deoxy-6-O-triphenylmethyl-α,β-D-mannopyranose (26)

Syrup. Yield: 67% (2 steps) (mixture of anomers; major:minor=60:40) from ManNAc. $^1$H-NMR (400 MHz, CDCl$_3$): δ 7.50-7.15 (m, 15H, 3×Ph), 6.15 (d, 0.6H, J=2.0 Hz, H-1), 5.92 (d, 0.4H, J=1.6 Hz, H-1), 5.83 (d, 0.4H, J=9.6 Hz, NH), 5.76 (d, 0.6H, J=9.6 Hz, NH), 5.40-5.25 (m, 1.6H), 5.03 (dd, 0.4H, J=4.0 & 10.0 Hz), 4.78 (m, 0.4H, H-2), 4.68 (m, 1H, H-2), 4.00 (m, 0.6H, H-5), 3.70 (m, 0.4H, H-5), 3.38 (dd, 0.4H, J=2.4 & 10.4 Hz), 3.30 (dd, 0.6H, J=2.4 & 10.8 Hz), 3.13-3.10 (m, 1H), 2.50-2.17 (m, 6H), 2.12 (s, 1.2H, NHAc), 2.10 (s, 1.8H, NHAc), 1.80-1.35 (m, 6H), 1.08-0.79 (m, 9H); $^{13}$C-NMR (100 MHz, CDCl$_3$): δ 172.7, 172.7, 171.9, 171.8, 171.0, 170.9, 170.4 (NHCO), 170.0 (NHCO), 143.8, 143.4, 129.1, 128.4, 128.3, 128.0, 127.3, 127.1, 91.6 (C-1), 90.5 (C-1), 86.8, 86.7, 74.8, 71.9, 71.6, 69.1, 65.4, 65.3, 61.8 (C-6), 61.7 (C-6), 49.9 (C-2), 49.5 (C-2), 36.0, 35.9, 35.8, 35.7, 23.4, 23.3, 18.3, 18.3, 18.2, 18.1, 18.0, 18.0, 14.2, 13.7, 13.6, 13.6, 13.5, 13.5; MALDI-MS: Calcd for C$_{39}$H$_{47}$NO$_9$Na ([M+Na]$^+$): 696.3149. found: 696.3350.

Example 4

General Procedure for the Synthesis of 2-acetamido-1,3,4-tri-O-acyl-2-deoxy-α,β-D-mannopyraose (5, 10 or 16)

A stirred mixture of 25, 26 or 27 (0.743 mmol) in 80% aqueous acetic acid (10 mL) was heated at 60° C. and monitored by TLC (hexanes:AcOEt). After ~4-7 h the reaction mixture was concentrated under reduced pressure and co-concentrated with toluene (10 mL×3). Column chromatography of the residue (hexanes:AcOEt) gave the products 6, 10 or 16.

2-acetamido-1,3,4-tri-O-acetyl-2-deoxy-D-mannopyraose (5)

Yield: 50%. $^1$H-NMR (400 MHz, CDCl$_3$): δ 6.14 (d, 1H, J=9.2 Hz, NH), 6.05 (d, 1H, J=1.6 Hz, H-1), 5.42 (dd, 1H, J=4.0 & 10.4 Hz, H-3), 5.19 (t, 1H, J=10.4 Hz, H-4), 4.64 (m, 1H, H-2), 3.82 (m, 1H, H-5), 3.73 (m, 1H, J=2.0 & 13.3 Hz, H-6a), 3.60 (m, 1H, J=3.6 & 13.3 Hz, H-6b), 2.72 (m, 1H, C6-OH), 2.18, 2.13, 2.06, 2.04 (s, 3H, NHAc); $^{13}$C-NMR (100 MHz, CDCl$_3$): δ 172.1, 170.9, 170.2, 170.2, 168.4 (NH$\underline{C}$O), 91.9 (C-1), 72.4, 68.7, 65.7, 60.7 (C-6), 49.3 (C-2), 23.2, 20.9, 20.8, 20.7; MALDI-MS: Calcd for $C_{14}H_{21}NO_9Na$ ([M+Na]$^+$): 370.1113. found 370.0904

2-acetamido-1,3,4-tri-O-butanoyl-2-deoxy-D-mannopyraose (10)

Semi-solid. Yield: 70% yield. $^1$H-NMR (400 MHz, CDCl$_3$): δ 6.11 (d, 1H, J=9.6 Hz, NH), 6.07 (d, 1H, J=2.0 Hz, H-1), 5.43 (dd, 1H, J=4.8 & 10.4 Hz, H-3), 5.19 (t, 1H, J=10.4 Hz, H-4), 4.68 (m, 1H, H-2), 3.82 (m, 1H, H-5), 3.75 (m, 1H, H-6a), 3.60 (m, 1H, H-6b), 2.75 (m, 1H, C6-O$\underline{H}$), 2.50-2.15 (m, 6H, 3×CH$_2$), 2.08 (s, 3H, NHAc), 1.80-1.50 (m, 6H, 3×CH$_2$), 1.08-0.80 (m, 9H, 3×CH$_3$); $^{13}$C-NMR (100 MHz, CDCl$_3$): δ 173.8, 172.6, 171.0, 170.2 (NH$\underline{C}$O), 91.8 (C-1), 72.5, 68.4, 65.5, 60.8 (C-6), 49.4 (C-2), 36.0, 36.0, 35.9, 23.2, 18.4, 18.2, 18.1, 13.6, 13.6, 13.6. MALDI-MS: Calcd for $C_{20}H_{33}NO_9Na$ ([M+Na]$^+$): 454.2053. found: 454.2036.

Example 5

General Procedure for the Synthesis of 2-Acetamido-1,3-di-O-acyl-2-deoxy-α,β-D-mannopyranose (9)

Scheme 3. Scheme for the synthesis of 2-acetamido-1,3-di-O-butanoyl-2-deoxy-D-mannopyranose; Condition: (a) 2,2-dimethoxypropane, P-TsOH, MeOH, 22° C. (b) butyric anhydride, pyridine, DMAP, 22° C.; (c) Acetic acid: water (5 : 1), 60° C.

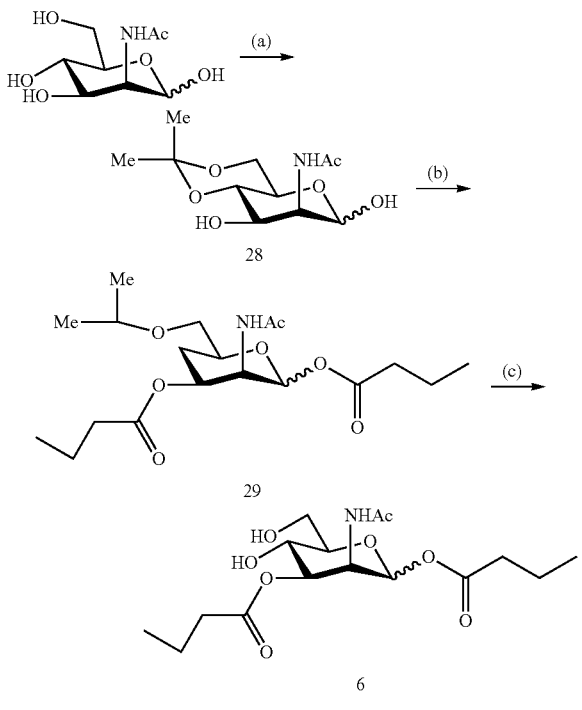

2-Acetamido-1,3-di-O-butanoyl-2-deoxy-4,6-O-isopropylidene-D-mannopyranose (6)

To a stirred mixture of 2 (2 g, 8.36 mmol) in anhydrous dimethyl formamide (DMF) (30 mL) at 22° C. was added 2,2-dimethoxypropane (3.98 mL, 32.5 mmol) followed by p-tolounesulfonic acid (p-TsOH, 20 mg). The reaction was monitored by TLC (dichloromethane:methanol 9:1) for completion. After ~6 h, the reaction mixture was neutralized with IR-40 (hydroxide) ion exchange resin (500 mg), filtered and concentrated under reduced pressure to obtain 28, which was taken to the next step without further purification.

To a stirred mixture of crude 28 and butyric anhydride (5.33 mL, 32.5 mmol) in pyridine (3.92 mL, 48.8 mmol) at 0° C. (ice-water bath) was added DMAP (cat.) and allowed to warm up to 22° C. After ~24 h, the reaction mixture was concentrated and co-concentrated with toluene (3×20 mL). Column chromatography of the residue (hexanes:AcOEt) gave pure 29 in 63% yields.

2-Acetamido-1,3-di-O-butanoyl-2-deoxy-4,6-O-isopropylidene-α,β-D-mannopyranose

Syrup, $^1$H-NMR (400 MHz, CDCl$_3$) (Major): δ 5.87 (d, 1H, J=1.6 Hz, H-1), 5.68 (d, 1H, J=9.2 Hz, NH), 5.00 (m, 1H, H-3), 4.78 (m, 1H, H-2), 4.05-3.45 (m, 4H, H-4, H-5, H-6a & H-6b), 2.40-2.19 (m, 4H, 2×CH$_2$), 2.07 (s, 3H, NHAc), 1.80-1.52 (m, 4H, 2×CH$_2$), 1.47 (s, 3H, CH$_3$), 1.40 (s, 3H, CH$_3$) 1.00-0.80 (m, 6H, 2×CH$_3$); $^{13}$C-NMR (100 MHz, CDCl$_3$): δ 172.6, 170.8, 170.5 (NHCOCH$_3$), 100.2, 91.3 (C-1), 70.3, 69.3, 68.7, 61.7, 49.8, 35.4, 21.0, 17.8, 17.7, 12.7, 12.6; FAB-MS: Calcd for $C_{19}H_{32}NO_8$ ([M+H]$^+$): 402.2127. found: 402.2127.

$^1$H-NMR (400 MHz, CDCl$_3$) (Minor): δ 5.98 (d, 1H, J=2.0 Hz, H-1), 5.71 (d, 1H, J=9.2 Hz), 5.26 (m, 1H, H-3), 4.65 (m, 1H, H-2), 3.90-3.65 (m, 4H, H-4, H-5, H-6a & H-6b), 2.52-2.25 (m, 4H, 2×CH$_2$), 2.02 (s, 3H, NHAc), 1.80-1.60 (m, 4H, 2×CH$_2$), 1.50 (s, 3H, CH$_3$), 1.40 (s, 3H, CH$_3$) 1.08-0.83 (m, 6H, 2×CH$_3$); $^{13}$C-NMR (100 MHz, CDCl$_3$): δ 172.6, 171.1, 169.8, 100.3, 92.5 (C-1), 69.0, 67.9, 66.6, 62.0, 50.0, 36.0, 29.0, 23.3, 19.3, 18.2, 13.6, 13.5; FAB-HR-MS: Calcd for $C_{19}H_{32}NO_8$ ([M+H]$^+$): 402.2127. found: 402.2127.

2-Acetamido-1,3-di-O-butanoyl-2-deoxy-D-mannopyranose

A suspension of either 29 (either anomer) (200 mg, 0.5 mmol) in 50% aqueous acetic acid (5 mL) was heated at 60° C. and monitored by TLC (AcOEt:methanol 95:5). After ~4 h the reaction mixture was concentrated under reduced pressure, co-concentrated with toluene (3×10 mL). Column chromatography of the residue (AcOEt:methanol 95:5) gave either major, 6 (85%) or minor (80%) respectively.

2-Acetamido-1,3-di-O-butanoyl-2-deoxy-D-mannopyranose (major, 6)

Crystalline solid. $^1$H-NMR (400 MHz, MeOD): δ 5.79 (s, 1H, J=2.0 Hz, H-1), 4.83 (dd, 1H, J=4.0 & 9.6 Hz, H-3), 4.60 (m, 1H, H-2), 4.72-3.65 (m, 3H, H-4, H-6a & H-6b), 3.49 (m, 1H, H-5), 2.30-2.15 (m, 4H, 2×CH$_2$), 1.91 (s, 3H, NHAc), 1.62-1.49 (m, 4H, 2×CH$_2$), 0.93-0.78 (m, 6H, 2×CH$_3$); $^{13}$C-NMR (100 MHz, MeOD): δ173.3, 172.6, 171.4 (NH$\underline{C}$O), 91.1 (C-1), 78.3, 74.0, 63.5, 60.1 (C-6), 49.9 (C-2), 35.6, 35.4, 21.3, 17.8, 17.7, 12.7, 12.6. MALDI-TOF-MS: Calcd for $C_{16}H_{37}NO_8Na$ [(M+Na)$^+$]: 384.1637. found: 384.1610.

2-Acetamido-1,3-di-O-butanoyl-2-deoxy-D-mannopyranose (Minor)

$^1$H-NMR (400 MHz, MeOD): δ 5.98 (s, 1H, H-1), 5.15 (m, 1H, H-3), 4.56 (m, 1H, H-2), 4.00-3.60 (m, 4H, H-4, H-5,

H-6a & H-6b), 2.52-2.25 (m, 4H, 2×CH$_2$), 2.02 (s, 3H, NHAc), 1.80-1.60 (m, 4H, 2×CH$_2$), 1.08-0.92 (m, 6H, 2×CH$_3$); $^{13}$C-NMR (100 MHz, MeOD): δ173.3, 172.2, 171.4 (NH$\underline{C}$O), 92.1 (C-1), 75.0, 71.8, 63.5, 60.1 (C-6), 49.6 (C-2), 36.0, 36.0, 21.5, 18.2, 18.1, 12.5, 12.3. MALDI-TOF-MS: Calcd for C$_{16}$H$_{37}$NO$_8$Na [(M+Na)$^+$]: 384.1637. found: 384.1679

Example 6

General Procedure for the Synthesis of Mix & Match Synthesis of Peracyl ManNAc Analogs with Different Acyl Chain Lengths CH$_3$); $^{13}$C-NMR (100 MHz, CDCl$_3$): δ171.0, 170.7, 170.6, 170.5, 170.1, 170.1, 170.0, 170.0, 169.7 (NH$\underline{C}$O), 169.6 (NH$\underline{C}$O), 91.5 (C-1), 90.6 (C-1), 73.4, 71.3, 70.2, 68.9, 65.6, 65.4, 62.1 (C-6), 62.0 (C-6), 49.6 (C-2), 49.4 (C-2), 35.9, 35.7, 23.3, 23.3, 20.7, 20.6, 20.6, 18.3, 17.9, 13.5, 13.4; FAB-MS: Calcd for C$_{18}$H$_{28}$NO$_{10}$ ([M+H]$^+$): 418.1716. found: 418.1713.

2-Acetamido-1,3,4-tri-O-acetyl-6-O-butanoyl-2-deoxy-α,β-D-mannopyranose (18)

To a stirred mixture of 10 (1 g, 2.88 mmol) and butyric anhydride (1 mL, 6.11 mmol) in pyridine (0.72 mL, 9.16 mmol) at 0° C. (ice-water bath) was added DMAP (cat.) and Scheme 4: Scheme for the synthesis of peracyl ManNAc analogs with different acyl chain lengths; conditions : (a) Butyric anhydride, pyridine, DMAP, 22° C.

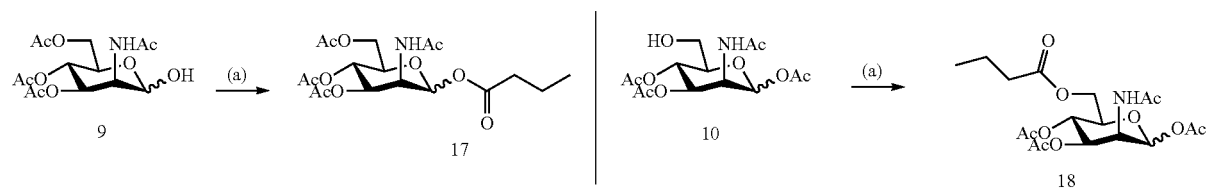

2-Acetamido-3,4,6-tri-O-acetyl-1-O-butanoyl-2-deoxy-α,β-D-mannopyranose (17)

To a stirred solution of 9 (1 g, 2.88 mmol) and butyric anhydride (1 mL, 6.11 mmol) in pyridine (0.72 mL, 9.15 mmol) at 0° C. (ice water bath) was added DMAP (cat.) and allowed to warm up to 22° C. After ~24 h, the reaction mixture was concentrated, co-concentrated with toluene (3×10 mL) and the residue was extracted with a mixture of dichloromethane (100 mL) and water (50 mL). The combined organic layers were dried over anh. Na$_2$SO$_4$, filtered and concentrated. Column chromatography of the residue (hexanes:AcOEt) gave 10 (75%) as a mixture of anomers.

Characterization of 2-Acetamido-3,4,6-tri-O-acetyl-1-O-butanoyl-2-deoxy-α,β-D-mannopyranose (17)

Crystalline solid. Mixture of anomers; major:minor=90:10: $^1$H-NMR (400 MHz, CDCl$_3$): δ 6.07 (d, 0.9H, J=1.6 Hz, H-1), δ 5.89 (d, 0.1H, J=1.6 Hz, H-1), 5.76 (d, 0.1H, J=9.2 Hz, NH), 5.74 (d, 0.9H, J=9.2 Hz, NH), 5.35 (dd, 0.9H, J=4.4 & 10.4 Hz), 5.18 (t, 0.9H, J=10.4 Hz), 5.10 (t, 0.1H, J=9.6 Hz), 5.08 (dd, 0.1H, J=3.6 & 9.6 Hz), 4.78 (m, 0.1H, H-2), 4.66 (m, 0.9H, H-2), 4.33 (dd, 0.1H), 4.30 (dd, 0.9H, J=5.4 & 12.3 Hz), 4.10-4.00 (m, 1.9H), 3.82 (m, 0.1H, H-5), 2.40 (t, 1.8H, CH$_2$), 2.36 (t, 0.2H, CH$_2$), 2.16, 2.11, 2.10, 2.09, 2.08, 2.08 (6s, 9H), 2.04 (s, 0.3H, NHAc), 2.02 (s, 2.7H, NHAc), 1.74 (q, 1.8H, CH$_2$), 1.67 (q, 0.2H, CH$_2$), 1.00 (t, 2.7H, CH$_3$), 0.80 (t, 0.3H, allowed to warm up to 22° C. After ~24 h, the reaction mixture was concentrated, co-concentrated with toluene (3×20 mL) and extracted with a mixture of dichloromethane and water. The combined organic layers were dried over anh. Na$_2$SO$_4$, filtered and concentrated. Column chromatography of the residue (hexanes:AcOEt 2:3) gave pure 18 in 85% yields 2-Acetamido-1,3,4-tri-O-acetyl-6-O-butanoyl-2-deoxy-α,β-D-mannopyranose (18)

Syrup, (Major:minor=8:2), $^1$H-NMR (400 MHz, CDCl$_3$): δ 6.03 (d, 0.80H, J=2.0 Hz, H-1), 5.88 (d, 0.20H, J=2.0 Hz, H-1), 5.87 (d, 0.80H, J=9.2 Hz, NH), 5.83 (d, 0.20H, J=9.2 Hz, NH), 5.34 (dd, 0.80H, J=4.4 & 10.0 Hz, H-3), 5.17 (t, 0.80H, J=10.0 Hz, H-4), 5.13 (t, 0.20H, J=10.0 Hz, H-4), 5.04 (dd, 0.20H, J=4.0 & 10.0 Hz, H-3), 4.79 (m, 0.20H, H-2), 4.64 (m, 1H, H-2), 4.30-4.00 (m, 2.8H), 3.80 (m, 0.20H, H-5), 2.35 (t, 2H, CH$_2$), 2.18, 2.12, 2.11, 2.09, 2.07, 2.05 (6s, 9H, 3×COCH$_3$), 2.02 (s, 0.6H, NHAc), 1.99 (s, 2.4H, NHAc), 1.70 (q, 1.6H, CH$_2$), 1.68 (q, 0.42H, CH$_2$), 0.98 (t, 0.6H, CH$_3$) 0.97 (t, 2.4H, CH$_3$); $^{13}$C-NMR (100 MHz, CDCl$_3$): δ 173.1, 173.1, 170.6, 170.1, 170.1, 170.0, 169.7, 169.7, 168.3 (NH$\underline{C}$O), 168.1 (NH$\underline{C}$O), 91.7 (C-1), 90.6 (C-1), 73.5, 71.4, 70.2, 68.8, 65.6, 65.3, 61.9 (C-6), 61.7 (C-6), 49.5 (C-2), 49.3 (C-2), 35.9, 35.8, 26.9, 23.3, 23.3, 20.8, 20.7, 20.7, 20.7, 20.6, 20.6, 20.6, 18.4, 18.2, 13.6, 13.6 FAB-MS: Calcd for C$_{18}$H$_{28}$NO$_{10}$ ([M+H]$^+$): 418.1716. found: 418.1711.

Example 7

Sialic Acid Analogs

General Procedure for the Synthesis of methyl 5-acetamido-2,4,7,8,9-penta-O-acyl-2,5-dideoxy-α,β-D-glycero-D-galactononulosonate Scheme 5: Scheme for the synthesis 5-Acetamido-2,4,7,8,9-penta-O-acyl-3,5-dideoxy-1-methyl ester-D-glycero-D-galacto-2-Nonulopyranosonic acid; Conditions: (a) Dowex-50 W-X2, dry MeOH, rt, under Ar, 24 h (92%); (b) (RCO)₂O, DMAP, dry pyridine, RT, under Ar, 24 h.

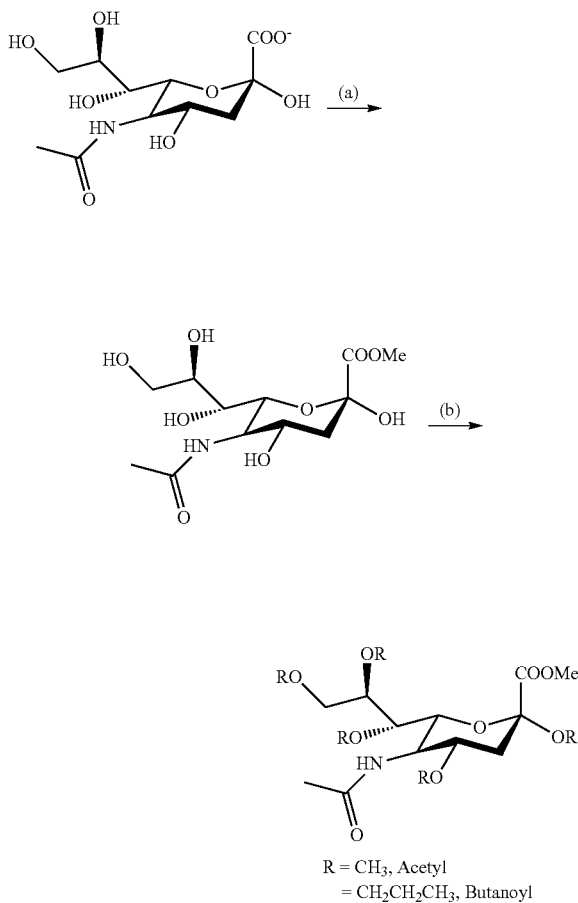

R = CH₃, Acetyl
= CH₂CH₂CH₃, Butanoyl

To a stirred solution of Neu5Ac (0.325 g) in anhydrous methanol (12 mL) in 21° C. was added Dowex-50 W-X2 (cat.) and stirred under argon atmosphere. After 24 h, the mixture was concentrated under vacuum and co-concentrated with toluene—the product of interest being Neu5AcOMe. To a stirred solution of Neu5AcOMe (0.5 g) in pyridine (2.0 mL) in 21° C. was added the corresponding anhydride (10 mmol) and 4-(dimethylamino)pyridine (cat.). After 24 h, the mixture was concentrated under vacuum and co-concentrated with toluene. The residue was dissolved in methylene chloride (100 ml), washed with cold aqueous HCl (0.5 N, 100 mL), water (100 mL), and saturated NaHCO3 (100 mL). The organic layer was filtered and concentrated. Column chromatography of the residue (hexanes/ethyl acetate) on silica gel provided the corresponding per-acyl compounds.

Methyl 5-acetamido-2,4,7,8,9-penta-O-butanoyl-2,5-dideoxy-α,β-D-glycero-D-galactononulosonate Semi-solid. Yield: 70% yield. $^1$H-NMR (400 MHz, CDCl$_3$): δ 5.36 (m, 1H), 5.29 (d, 1H, J=6.4 Hz, NH), 5.23 (m, 1H), 5.06 (m, 1H, H-5), 4.50 (dd, 1H, J=2.4 & 12.4 Hz, H-4), 4.18-4.00 (m, 3H, H-7, H-8, H-9), 3.79 (s, 3H, OMe), 2.55 (dd, 1H, H-3a), 2.45-2.20 (m, 10H), 2.10 (dd, 1H, H-3b), 1.92 (s, 3H, NHAc), 1.78-1.45 (m, 10H), 1.10-0.78 (m, 15H); $^{13}$C-NMR (100 MHz, CDCl$_3$): δ 173.6, 173.1, 172.9, 172.8, 171.0, 170.0, 166.43 (NH$\underline{C}$O), 97.5 (C-1), 73.1, 71.6, 68.0, 68.9, 62.0, 53.1, 49.5 (Me$\underline{O}$), 36.1, 36.0, 36.0, 35.9, 35.8, 23.2, 18.4, 18.3, 18.2, 18.2, 18.1, 13.6, 13.6, 13.6, 13.6, 13.5; ESI-MS: Calcd for C$_{32}$H$_{51}$NO$_{14}$Na ([M+Na]$^+$): 696.5. found: 696.5.

Synthesis of 1,3,4,6-tetra-O-butanoyl-2-deoxy-2-(4-oxopentanoyl)-amino-α,β-D-mannopyranose (12) and 1,3,4-tri-O-butanoyl-2-deoxy-2-(4-oxopentanoyl)amino-α,β-D-mannopyranose (13)

The N-4-oxo-pentanoyl-α,β-D-mannosamine analogs 12 and 13 were synthesized as shown in Scheme 3 (the conditions for the synthesis and characterization of 12, 30 and 13 are provided below).

Scheme 6: Conditions: (a) Ph$_3$C-Cl, pyridine, RT-60° C., 48 h; (b) Butyric anhydride, pyridine, DMAP, 0-22° C., 24 h (c) Acetic acid:water (3:1), 60° C., 3-4 h.

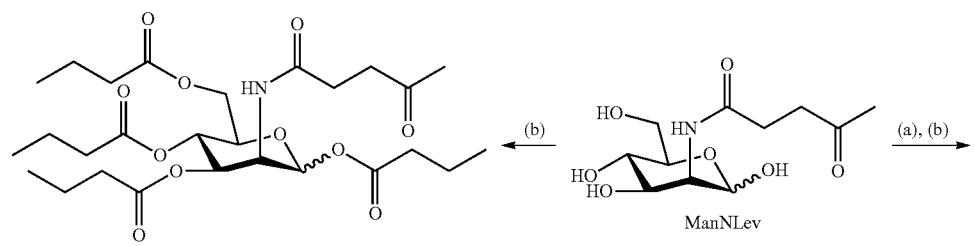

12

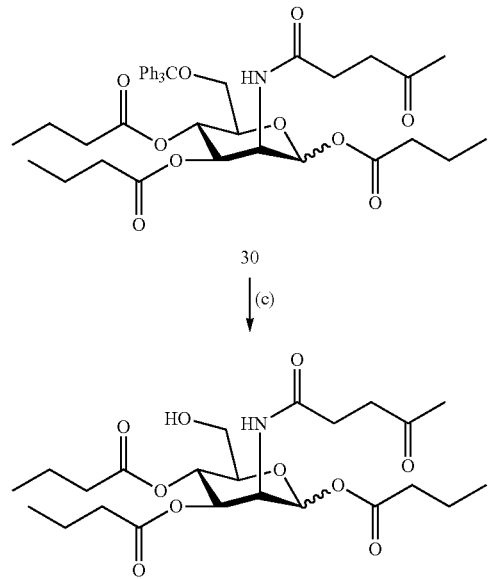

30

↓(c)

13

Synthesis of 1,3,4,6-tetra-O-butanoyl-2-deoxy-2-(4-oxopentanoyl)-amino-α,β-D-mannopyranose (12)

To a stirred solution of ManNLev (2.16 mmol) in pyridine (1.46 ml, 18 mmol) at 0° C. (ice-water bath), butyric anhydride (12 mmol) was added. The reaction mixture was allowed to warm up to 22° C. and monitored by TLC (hexanes:AcOEt 1:1). After 24 h, the mixture was concentrated with toluene (3×10 ml), and extracted using a mixture of dichloromethane (100 ml) and water (50 ml). The organic layers were collected, dried over anh. $Na_2SO_4$, filtered, and concentrated. Column chromatography of the residue (hexanes:AcOEt) gave the titled compound 12 as a mixture of anomers.

Characterization of 1,3,4,6-tetra-O-butanoyl-2-deoxy-2-(4-oxo-pentanoyl)amino-α,β-D-mannopyranose (12)

Syrup, Yield: 80% (2 steps) (mixture of anomers; major:minor 78:22) from ManNAc: $^1$H-NMR (400 MHz, $CDCl_3$): δ 6.25 (d, 0.78H, J=9.2 Hz, NH), 6.15 (d, 0.22H, J=9.2 Hz, NH), 6.07 (s, 0.78H, J=2.0 Hz, H-1), 5.90 (s, 0.22H, J=1.6 Hz, H-1), 5.32 (dd, 0.78H, J=4.4 & 10.4 Hz, H-3 major), 5.25-5.09 (m, 1H), 5.05 (dd, 0.22H, J=4.4 & 10.4 Hz, H-3 minor), 4.75 (m, 0.22H, H-2), 4.60 (m, 0.78H, H-2), 4.37-3.98 (m, 2.78H), 3.82 (m, 0.22H, H-5 minor), 2.85-2.10 (m, 12H, 4×$CH_2$, 2×$CH_2$), 1.80-1.50 (m, 8H, 4×$CH_2$), 1.10-0.80 (m, 12H, 4×$CH_3$); $^{13}$C-NMR (100 MHz, $CDCl_3$): δ 207.6, 207.4 {2×(—CO—)}, 173.3, 173.2, 172.5, 172.5, 172.5, 172.5, 172.2, 172.1, 171.1, 170.8, 91.6 (C-1), 90.5 (C-1), 73.4, 71.0, 70.4, 68.9, 65.1, 65.1, 61.8 (C-6), 61.7 (C-6), 49.3 (C-2), 49.3 (C-2), 38.7, 38.7, 35.9, 35.9, 35.8, 35.7, 30.0, 30.0, 30.0, 30.0, 29.9, 29.8, 29.8, 29.8, 18.4, 18.3, 18.0, 18.0, 18.0, 18.0, 18.0, 17.9, 13.6, 13.6, 13.6, 13.5, 13.5, 13.5, 13.5, 13.5; MALDI-MS: Calcd for $C_{27}H_{43}NO_{11}Na$ ([M+Na]$^+$): 580.6202. found: 580.5537.

Synthesis of 1,3,4-tri-O-butanoyl-6-O-triphenylmethyl-2-deoxy-2-(4-oxopentanoyl)amino-α,β-D-mannopyranose (30)

ManNLev (2.0 g), pyridine (15 ml), and trityl chloride (2.0 g) were combined in a RB flask and stirred for 48 h at rt. The mixture was then stirred for one more hour at 65° C. After completion of the reaction, as monitored by TLC in 100% EtOAc, the reaction mixture was extracted with water/EtOAc. The organic layer was collected, coevaporated with toluene and taken directly to next step. The crude reaction mixture was combined with butyric anhydride (12 ml) and pyridine (10 ml) and then stirred for 24 h at rt. After completion of the reaction, as monitored by TLC (EtOAc:hexane=1:4), the reaction mixture was coevaporated with toluene and extracted with water. The organic layer was collected, concentrated, and purified by column chromatography to obtain 30 with 60% in overall yield.

Characterization of 1,3,4-tri-O-butanoyl-6-O-triphenylmethyl-2-deoxy-2-(4-oxopentanoyl)amino-α,β-D-mannopyranose (30)

Syrup, Yield: 60% (2 steps) (mixture of anomers; major:minor 53:47) from ManNLev. $^1$H-NMR (400 MHz, $CDCl_3$): δ 7.52-7.15 (m, 15H, 3×Ph), 6.20-6.07 (d, 1.53H, H-1 major, NH-major and NH-minor), 5.89 (s, 0.47H, H-1-minor), 5.35-5.21 (m, 1.53H), 5.01 (m, 0.47H, H-3 minor), 4.74 (m, 0.53H, H-2 major), 4.61 (m, 0.47H, H-2 minor), 3.98 (m, 0.53H, H-5), 3.71 (m, 0.47H, H-5), 3.40-3.10 (m, 2H), 2.85-2.75 (m, 2H), 2.69-2.50 (m, 2H), 2.45-1.90 (m, 9H), 1.81-1.38 (m, 6H), 1.10-0.78 (m, 6H); $^{13}$C-NMR (100 MHz, $CDCl_3$): δ 207.2, 207.0 {2×(—CO—)}, 172.7, 172.7, 172.4, 172.1, 171.8, 171.8, 171.2, 170.8, 143.5, 143.5, 128.8, 128.8, 128.6, 128.6, 127.2, 127.2, 127.1, 91.6 (C-1), 90.5 (C-1), 86.8, 86.7, 74.8, 72.0, 71.5, 69.8, 69.3, 65.5, 62.1 (C-6), 62.0 (C-6), 49.5 (C-2), 49.5 (C-2), 38.6, 38.5, 36.0, 35.9, 35.8, 35.7, 30.0, 30.0, 30.0, 30.0, 29.8, 18.3, 18.2, 18.2, 18.1, 18.0, 18.0, 13.6, 13.6, 13.6, 13.6, 13.5, 13.5; MALDI-MS: Calcd for $C_{42}H_{51}NO_{10}Na$ ([M+Na]$^+$): 752.3411. found: 752.6177.

Synthesis of 1,3,4-tri-O-butanoyl-2-deoxy-2-(4-oxo-pentanoyl)-amino-α,β-D-mannopyranose (13) from 30

A stirred mixture of 1,3,4-tri-O-butanoyl-6-O-trityl-2-deoxy-N-levulinoyl-α,β-D-mannosamine (0.743 mmol) in 80% aqueous acetic acid (10 ml) was heated at 60° C. and monitored by TLC (hexanes:AcOEt). After ~4 h, the reaction mixture was concentrated with toluene (3×10 ml). Column chromatography of the residue (hexanes:AcOEt) gave the tri-butyrate 13 (as a mixture of anomers) in a 75% yield.

Characterization of 1,3,4-tri-O-butanoyl-2-deoxy-2-(4-oxopentan-oyl)-amino-α,β-D-mannopyranose (13)

Syrup, Yield: 75% (2 steps) (mixture of anomers; major:minor 53:47) from ManNAc: $^1$H-NMR (400 MHz, CDCl$_3$): δ 6.62 (d, 0.44H, J=9.2 Hz, NH), 6.46 (d, 0.56H, J=9.2 Hz, NH), 6.14 (s, 0.44H, H-1), 5.89 (s, 0.56H, H-1), 5.50-5.02 (m, 2H), 4.78 (m, 0.56H, H-2), 4.62 (m, 0.44H, H-2), 3.00-2.10 (m, 11.68H, 3×CH$_2$, 2×CH$_2$, NHAc), 1.88 (s, 1.32H, NHAc), 1.70-1.40 (m, 6H, 3×CH$_2$), 1.10-0.76 (m, 9H, 3×CH$_3$); $^{13}$C-NMR (100 MHz, CDCl$_3$): δ 207.8, 207.5, 173.6, 173.5, 172.6, 172.6, 172.6, 172.2, 171.3, 171.0, 143.5, 91.7 (C-1), 90.6 (C-1), 75.5, 71.1, 68.6, 65.4, 65.4, 60.8 (C-6), 60.8 (C-6), 49.7 (C-2), 49.3 (C-2), 38.6, 38.5, 36.0, 35.9, 35.8, 35.7, 29.9, 29.9, 29.8, 29.8, 18.4, 18.3, 18.2, 18.1, 18.0, 18.0, 13.6, 13.6, 13.6, 13.6, 13.5, 13.5; MALDI-MS: Calcd for C$_{23}$H$_{37}$NO$_{10}$Na ([M+Na]$^+$): 510.5304. found 510.5321.

Example 8

Cell Culture Methods and Supplementation

For cell culture studies, the compounds of the invention are used as a mixture of anomers, as pure α-anomer and as pure β-anomer Stock solutions of the sugar analogs are made in ethanol at concentrations of 10 mM and 50 mM. Unless otherwise noted, throughout this study Jurkat cells (Clone E-6, ATCC, Manassas, Va.) are cultured in RPMI 1640 medium supplemented with 300 mg/L glutamine, 5.0% fetal bovine serum (HyClone, Logan, Utah) and 1.0% of a 100× dilution of a pen/strep stock solution containing penicillin (100 units/mL) and streptomycin (100 μg/mL); HL-60 cells (ATCC, Manassas, Va.) are cultured in RPMI 1640 medium supplemented with 10% FBS and pen/strep; and AD293 (HEK) cells (Stratagene, La Jolla, Calif.) are grown in DMEM medium with 10% FBS and pen/strep. In all cases, cells are incubated in a standard 37° C. in a 5.0% CO$_2$, water-saturated environment. Cell counting is performed with a Beckman-Coulter Z2 particle counter and hemacytometer.

Toxicity and Growth Inhibition Assays

Solutions of the analogs in EtOH (10 mM stock) are coated onto 24-well plates at a range of concentrations from 0-320 μM and ethanol is allowed to evaporate. Jurkat cells (1.0×10$^5$ cells) in 0.5 mL of medium are plated in each well (day 0). On days 3 and 5, fresh medium (1.0 mL) is added to each well. Cell cultures are mixed by gentle pipetting and 100 μL of cell suspension are taken from each well and counted. On days 7, 9, 11, 13 and 15, 1.0 mL of cell suspension is removed from each well after thorough mixing and fresh medium (1.0 mL) is added. Cells are counted on day 15 and the cell density is plotted as a percentage of control.

Cell Viability Assays

Jurkat cells (2.0×10$^5$ cells/mL) are seeded with the compounds of the invention at 200 μM in 6-well T. C. plates. Aliquots of cell suspension (20 μL) are removed on a daily basis diluted with either PBS (20 μL) or trypan blue solution (20 μL) and cell viability is determined by using the standard trypan blue exclusion method; three replicate counts are taken for each condition.

Morphological Changes to HEK293 and HeLa Cells

The studies on morphological changes induced by sodium butyrate and compounds of the invention are performed following a reported procedure. Briefly, HeLa cells (200,000 cells per well in a 6-well plate) are plated and allowed to form monolayers. After 24 h, the supernatant is aspirated, fresh medium (4.0 mL) is added and treated with either ethanol (20 μL (0.5%), control), sodium butyrate, or a compound of the invention (250 μM). For the AD 293 (HEK) cells 2.0×10$^6$ cells in 10 mL of medium (100 mm tissue culture dishes) are plated and treated, immediately after plating, with either ethanol (50 μL, control), 5 (5.0 mM), or a compound of the invention. Images are acquired at various time intervals under bright field using a Nikon Eclipse TE200 inverted microscope equipped with a DXM 1200 digital camera.

Luc-p21$^{WAF1/cip1}$ Luciferase Reporter Gene Assays

The plasmid Luc-p21$^{Cip1/WAF1}$ (a gift from Vogelstein Laboratory, JHMI, Baltimore, Md.) is amplified and purified utilizing a plasmid maxi kit (Cat. No. 12163. Qiagen, Valencia, Calif.) following the manufacturer's protocol. HEK cells (2.5×10$^5$) are seeded in 3.0 mL medium and grown in 6-well T. C. plates. Transfection is performed using lipofectamine 2000 (Cat. No. 11668-019, Invitrogen, Carlsbad, Calif.) following the protocol supplier's protocol. Cells are trypsinized 24 h after transfection and seeded at 250,000 cells per well with concentrations of compounds of the invention. After 72 h, the cells are trypsinized, counted and lysed in 300 μL of luciferase cell culture lysis buffer and diluted five-fold in the same buffer. Luminometry is performed utilizing the 'Luciferase Assay System' (Cat. No. 1500, 4550, Promega, Madison, Wis.) following supplier's protocol. Luciferase Assay Reagent (100 μL) is added to the cell lysate (20 μL) in luminometer tubes (Cat. No. 55.476, Sarstedt, Newton, N.C.) and the luminescence is measured immediately using a Berthold Sirius Luminometer. The final values are normalized relative to ethanol-treated controls and are reported on a per cell basis.

Endogenous p21$^{WAF1}$ Assays

Endogenous expression of p21$^{WAF1}$ is detected following a reported procedure with minor modifications. Jurkat cells (5.0×10$^6$ cells in 10 mL medium) are incubated with either ethanol or sodium butyrate or a compound of the invention. On a daily basis, aliquots of cells (~1.0×10$^6$ per sample) are taken, washed with PBS (2×1.0 mL), fixed with Reagent A (Fix and Perm Kit, Caltag Laboratories, CA, Cat. No. GAS-003) for 10 min at room temperature, washed with washing buffer (PBS containing 5.0% FBS, 0.1% NaN$_3$), re-suspended in 95% v/v methanol and kept on ice. After 30 min, cells are again washed with washing buffer and incubated with FITC-conjugated anti-p21$^{WAF1}$ antibody (Calbiochem, San Diego, Calif., Cat. No. OP64F) at 2.0 μg/mL in Reagent B (100 μL) (Fix and Perm Kit, Caltag Laboratories) for 1.0 h at room temperature in the dark. Finally, cells are re-suspended in washing buffer (500 μL) and analyzed by flow cytometry. Three replicate samples are taken for each condition and 10,000 events are counted for each sample.

Flow Cytometry Analysis of Cell Cycle Status

The cell cycle arrest induced by butyrate analogs is studied following the standard protocol. Briefly, Jurkat cells (2.3×10$^5$ cells/mL) are incubated with various concentrations of a compound of the invention for five days. The cells are then harvested, counted, washed twice with PBS, re-suspended in PBS (500 µL), added to a cold solution of 78% aqueous ethanol (4.5 mL) using a glass Pasteur pipette and kept at 2.0° C. for at least 24 h. The fixed cells are centrifuged twice to remove the ethanol completely, re-suspended in propidium iodide (PI)/ribonuclease A (RNase A) staining buffer (BD Pharmingen, Catalog No. 550825, San Diego, Calif.) (500 µL for $1.0 \times 10^6$ cells), incubated at 37° C. for 15 min and analyzed by flow cytometry. The cellular aggregates are excluded from single cell populations using an area-width plot (FL2-PI fluorescence) for the cell cycle status determination.

Time Course of Cell Cycle Status

Jurkat cells ($2.5 \times 10^5$ cells/mL) are incubated with either ethanol (0.2%) or sodium butyrate or a compound of the invention. Aliquots of cell suspensions are taken on day 0 and days 2-6, washed with PBS (twice) and fixed in 75% ethanol at 2.0° C. for at least 48 h. The cells are stained with PI/RNase staining buffer and analyzed by flow cytometry as given above.

Assay for Total Sialic Acid Production

Jurkat cells ($5.0 \times 10^6$ cells in 10 mL medium) are incubated a compound of the invention at various concentrations. After three days, the cells ($1.0 \times 10^6$ cells per sample) are lysed by freeze-thaw cycles (three times). The cell lysates are analyzed by using an adapted version of the periodate-resorcinol assay with the periodic acid oxidation step performed on ice to allow quantification of total (i.e., free monosaccharide plus glycoconjugate-bound) sialic acid. For each assay, a standard curve is obtained using N-acetylneuraminic acid (Pfanstiehl, Waukegan, Ill.) for calibration.

Toxicity of Sodium Butyrate (5) Towards Cells Primed with ManNAc

Jurkat cells ($5.0 \times 10^5$ per mL) are incubated with PBS and a compound of the invention at 50 or 100 mM. After 48 h, the cells are counted, harvested, washed once in fresh medium and plated in a 24-well plate containing various concentrations of sodium butyrate (0-2.0 mM; a stock solution of 200 mM in PBS was used for dilutions and control samples). Cell cultures are maintained and growth is monitored for 15 days as described above under the toxicity and growth inhibition assays. Experimental procedures essentially similar to those know in the art are examined and data on caspase-3 activity assay in Jurkat cells for dose dependent apoptosis induced by a compound of the invention is collected.

Butyrate Induced Cell Death is Dependent on the Core Sugar Moiety

In initial assays, Jurkat (human T-lymphoma) cells are incubated with compounds of the invention and growth rates were monitored. The compounds reduce cell proliferation at early time points (days 3 & 5) in a dose dependent manner.

Next, based on seminal reports of the ability of butyrate to induce SCFA-characteristic differentiation of cancer cells, the compounds of the invention are expected to induce similar morphological changes in HeLa cells. Upon three days of incubation, the compounds of the invention induce differentiation of HeLa cells, as seen by increased spreading and long outgrowth of processes.

Hexosamine-Delivered Butyrate has Characteristic SCFA Activity

In this section, we present evidence for the first aspect of our model to describe the bioactivity of the compounds of the invention against cancer cells—namely that sugar-delivered butyrate acts as an HDACi—by a set of three complementary assays. Specifically, activation of gene expression characteristic of HDACi, as exemplified by $p21^{WAF1}$-up regulation, is demonstrated in a luciferase reporter assay, up regulation of endogenous levels $p21^{WAF1}$ is then tested upon exposure to the compounds of the invention or sodium n-butyrate, and analysis of cell cycle progression through propidium iodide/ribonuclease A assays is done. Together, these assays provide convincing proof that sugar-delivery n-butyrate retains its characteristic SCFA bioactivity.

All references cited herein, whether in print, electronic, computer readable storage media or other form, are expressly incorporated by reference in their entirety, including but not limited to, abstracts, articles, journals, publications, texts, treatises, technical data sheets, interne web sites, databases, patents, patent applications, and patent publications.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof.

A number of embodiments of the invention have been described. Nevertheless, it will be understood that various modifications may be made without departing from the spirit and scope of the invention. Accordingly, other embodiments are within the scope of the following claims.

What is claimed is:

1. A compound of formula I, or pharmaceutically acceptable salt thereof:

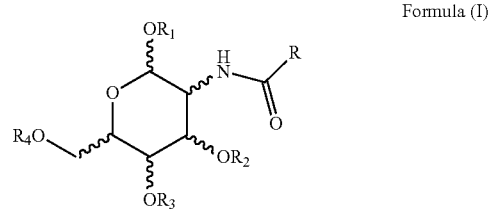

Formula (I)

wherein, $R_1$ is H and each of $R_2$, $R_3$ and $R_4$ is independently —C(O)(CH$_2$)$_n$CH$_3$ wherein each n is independently an integer from 1-18; and R is alkyl or alkenyl, each of which is optionally substituted with 1-4 substituents selected from acyl, oxo, azido, aryl, —OC(O)alkyl, or —SC(O)alkyl.

2. A compound of formula II or formula IV, or pharmaceutically acceptable salt thereof:

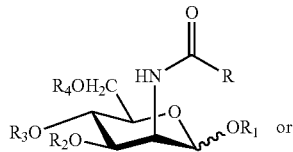

Formula (II)

or

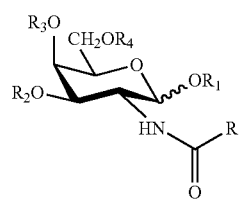

Formula (IV)

wherein,
R$_1$ is H and each of R$_2$, R$_3$ and R$_4$ is independently —C(O)(CH$_2$)$_n$CH$_3$ wherein each n is independently an integer from 1-18; and
R is alkyl or alkenyl, each of which is optionally substituted with 1-4 substituents selected from acyl, oxo, azido, aryl, halogen, —OC(O)alkyl, or —SC(O)alkyl.

3. The compound of claim 2, wherein each of R$_2$, R$_3$ and R$_4$ is —C(O)(CH$_2$)$_2$CH$_3$.

4. The compound of claim 2, wherein R is alkyl or a substituted alkyl which may be substituted by oxo, azido, aryl, halogen, —OC(O)alkyl, or —SC(O)alkyl.

5. The compound of claim 1, of formula III, or pharmaceutically acceptable salt thereof:

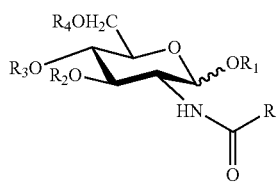

Formula (III)

wherein,
R$_1$ is H and each of R$_2$, R$_3$ and R$_4$ is independently —C(O)(CH$_2$)$_n$CH$_3$ wherein each n is independently an integer from 1-18; and
R is alkyl or alkenyl, each of which is optionally substituted with 1-4 substituents selected from acyl, oxo, azido, aryl, OC(O)alkyl, or —SC(O)alkyl.

6. A pharmaceutical composition comprising a compound of claim 1 and a pharmaceutically acceptable carrier.

7. The composition of claim 6, further comprising an additional therapeutic agent.

8. A kit comprising an effective amount of a compound of claim 1 in unit dosage form, together with instructions for administering the compound to a subject suffering from or susceptible to a cancer disease or disorder or symptoms thereof.

* * * * *